(12) United States Patent
Dey et al.

(10) Patent No.: US 7,399,786 B2
(45) Date of Patent: Jul. 15, 2008

(54) DERIVATIVES OF AMINO ACIDS FOR TREATMENT OF OBESITY AND RELATED DISORDERS

(75) Inventors: Debendranath Dey, Fremont, CA (US); Abjiheet Nag, Fremont, CA (US); Bindu Pandey, Fremont, CA (US); Preeti Balse, Fremont, CA (US); Partha Neogi, Fremont, CA (US); Bishwajit Nag, Union City, CA (US)

(73) Assignee: Bexel Pharmaceuticals, Inc., Union City, CA (US)

( * ) Notice: Subject to any disclaimer, the term of this patent is extended or adjusted under 35 U.S.C. 154(b) by 322 days.

(21) Appl. No.: 11/174,301

(22) Filed: Jun. 30, 2005

(65) Prior Publication Data

US 2007/0004725 A1 Jan. 4, 2007

(51) Int. Cl.
*A61K 31/19* (2006.01)
*C07C 63/00* (2006.01)

(52) U.S. Cl. ........................ 514/557; 562/405; 514/506; 514/557; 514/237.5; 514/255.01; 560/26

(58) Field of Classification Search ................... 560/26; 562/405; 544/162, 386; 514/237.5, 255.01, 514/506, 557
See application file for complete search history.

(56) References Cited

U.S. PATENT DOCUMENTS 7,087,576 B2  8/2006  Nag et al.

OTHER PUBLICATIONS

Kato et al., 2002, CAS: 137:63252.*
Horner et al., 1953, CAS 47:9185.*
Gustak et al., 1956, CAS: 50:56697.*
Jorgensen et al., 1963, CAS: 59: 35887.*
Asquith et al., 1967, CAS: 67: 100407.*
Lygo et al., 2004, CAS: 142: 219539.*
Nishiyama et al., 1995, CAS: 122:106494.*
Sonobe et al., Heterocycles, 1983, 20(3): 397-400.*
Genevieve Pilon, et al., "Inhibition of Inductible Nitric-oxide Synthase by Activators of AMP-activated Protein Kinase", *J. Biol. Chem.*, 279, 20 (2004) pp. 20767-20774.
Sonia Kapur, et al., "Expression of Nitric Oxide Synthase in Skeletal Muscle", *Diabetes*, 46 (1997) pp. 1691-1700.
Mylene Perreault, et al., "Targeted disruption of inducible nitric oxide synthase protects against obesity-linked insulin resistance in muscle", *Nature Medicine*, 7, No. 10 (2001), pp. 1138-1143
Daniel S. Fletecher, et al. "Therapeutic Administration of a Selective Inhibitor of Nitric Oxide Synthase Does Not Ameliorate the Chronic Inflammation and Tissue Damage Associated with Adjuvant-Induced Arthritis in Rats" *J. Pharm. Exp. Ther.*, 284, No. 2 (1998) pp. 714-721.
Gokhan S. Hotamisligil, et al., "Tumor Necrosis Factor α: A Key Component of the Obesity-Diabetes Link", *Diabetes*, 43 (1994) pp. 1271-1278.
Ranjan Mukherjee, et al., "A Selective Peroxisome Proliferator-Activated Receptor-γ (PPARγ) Modulator Blocks Adipocyte Differentiationn but Stimulates Glucose Uptake in 3T3-Li Adipocytes", *Mol. Endo.*, 14(9) (2000) pp. 1425-1433.
International Search Report, dated Feb. 16, 2007, from corresponding Internatinal Application No. PCT/US 06/25883, 2 pages.
Written Opinion of the International Searching Authority, dated Feb. 16, 2007, from corresponding International Application No. PCT/US06/25883.

* cited by examiner

*Primary Examiner*—Rei-Tsang Shiao
(74) *Attorney, Agent, or Firm*—Weaver Austin Villeneuve & Sampson LLP

(57) ABSTRACT

Novel amino acid derivatives are provided that are useful for management of disorders such as obesity and immunological diseases. The derivatives are also useful in lowering blood glucose levels in hyperglycemic disorders and for treating related disorders such as body weight gain, elevated free fatty acid, cholesterol and triglyceride levels and other disorder exacerbated by obesity.

24 Claims, 7 Drawing Sheets

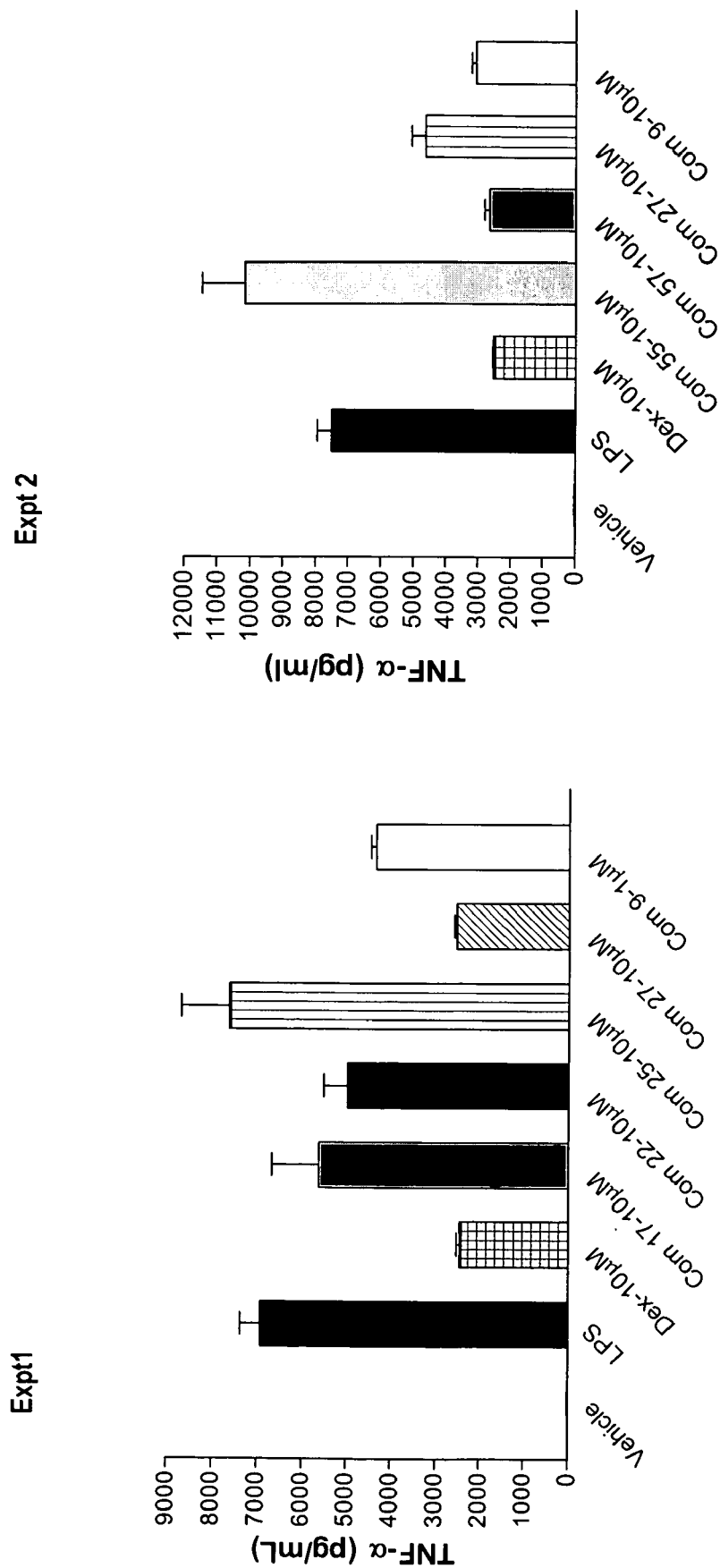
Fig 1. Inhibition of TNF-α by different compounds

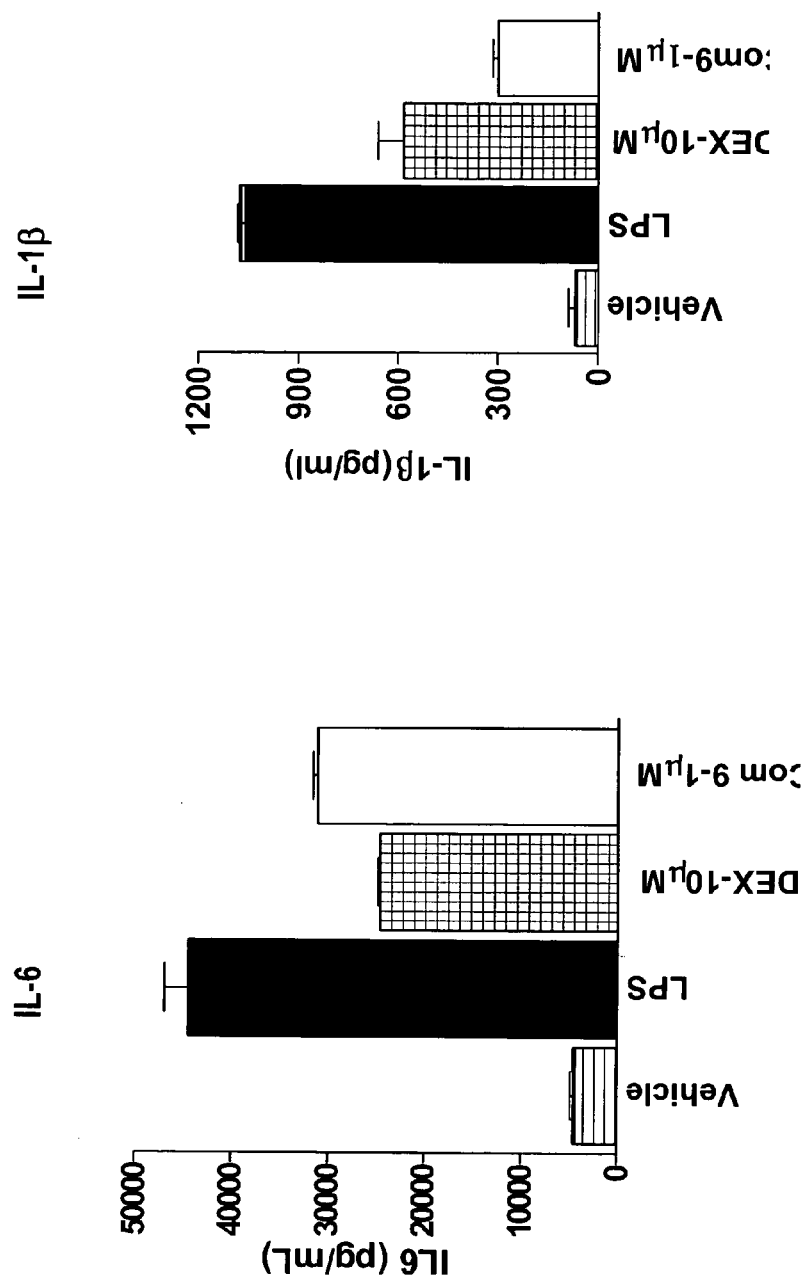
Fig 2. Inhibition of IL-6 and IL-1β by compound 9

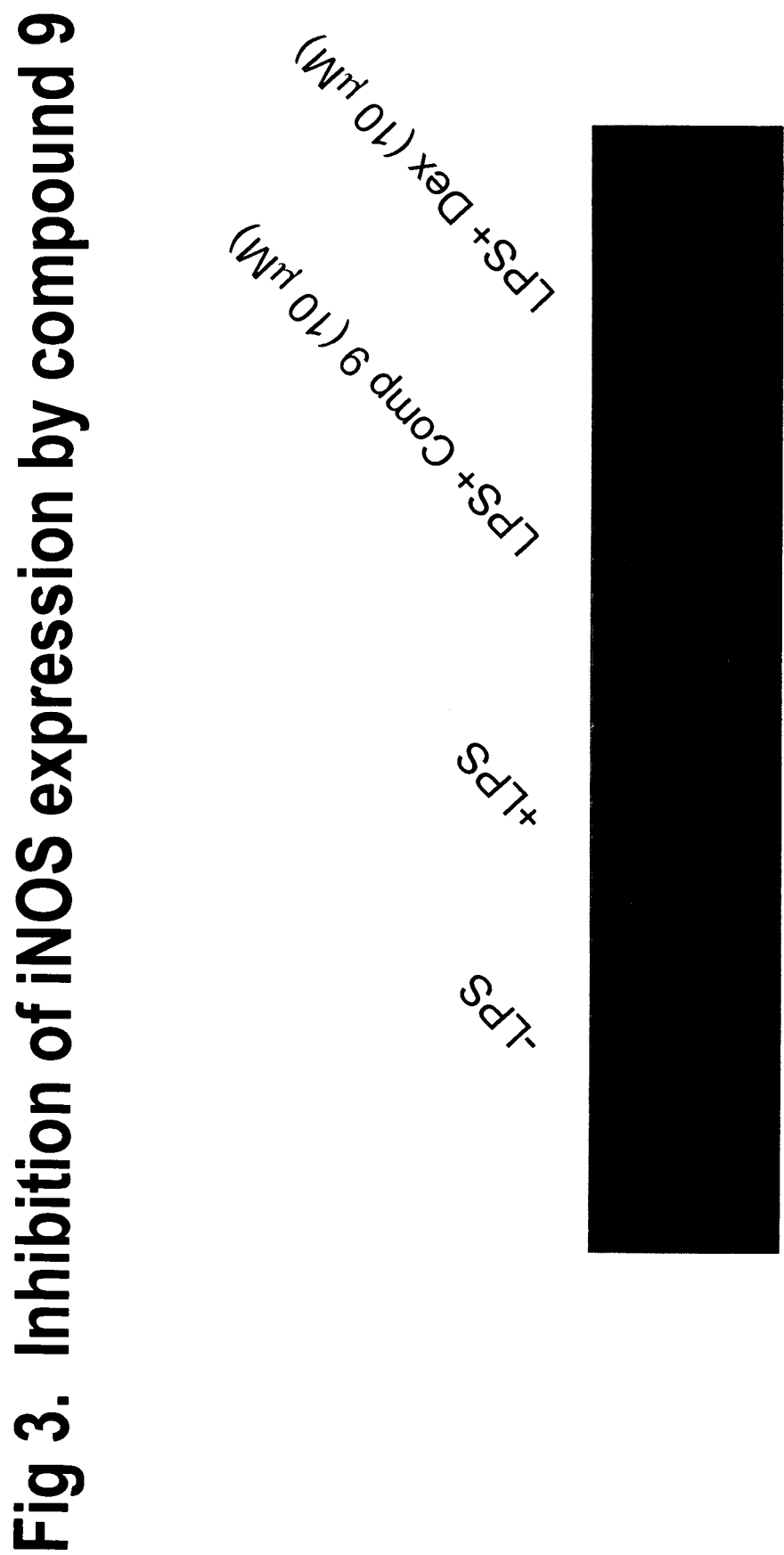
Fig 3. Inhibition of iNOS expression by compound 9

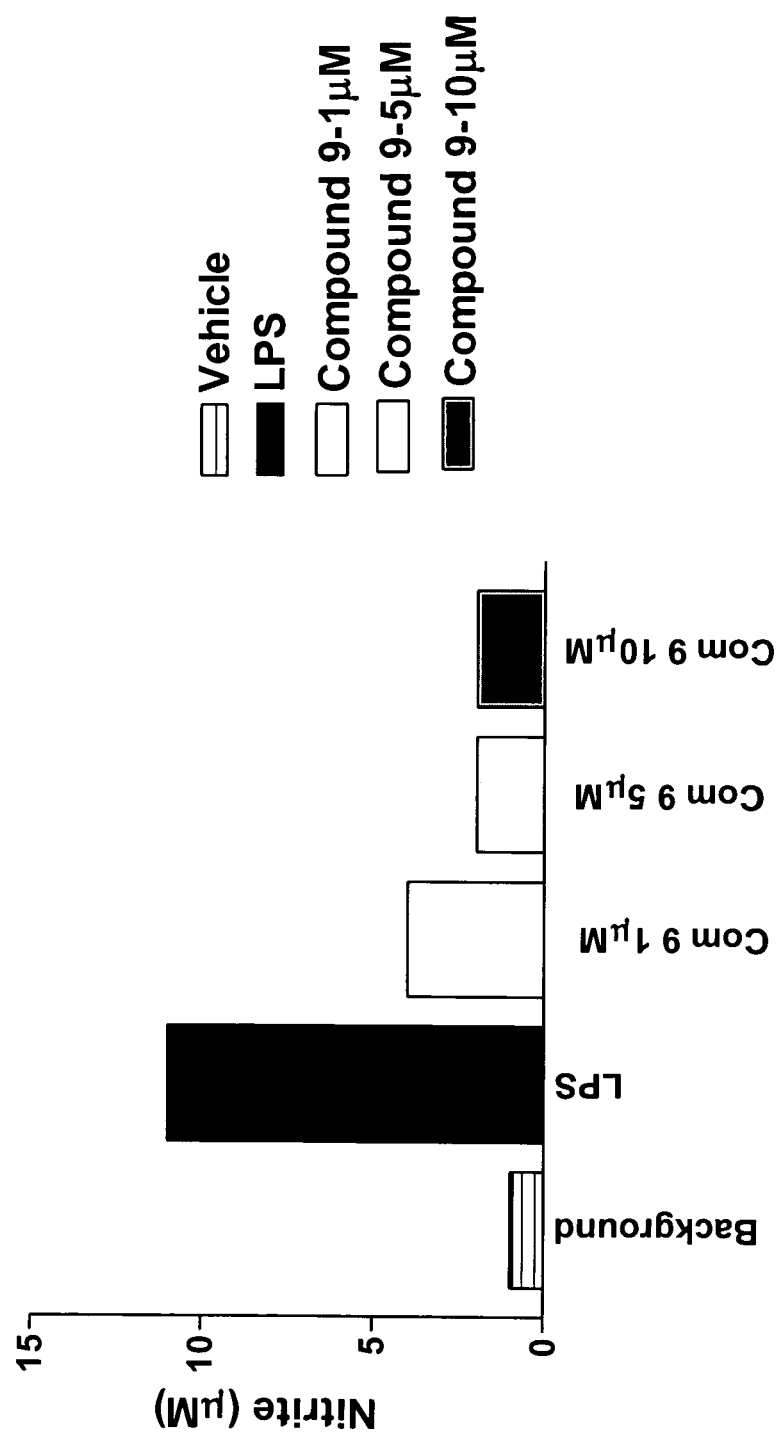
Fig 4. Inhibition of NO production by Compound 9

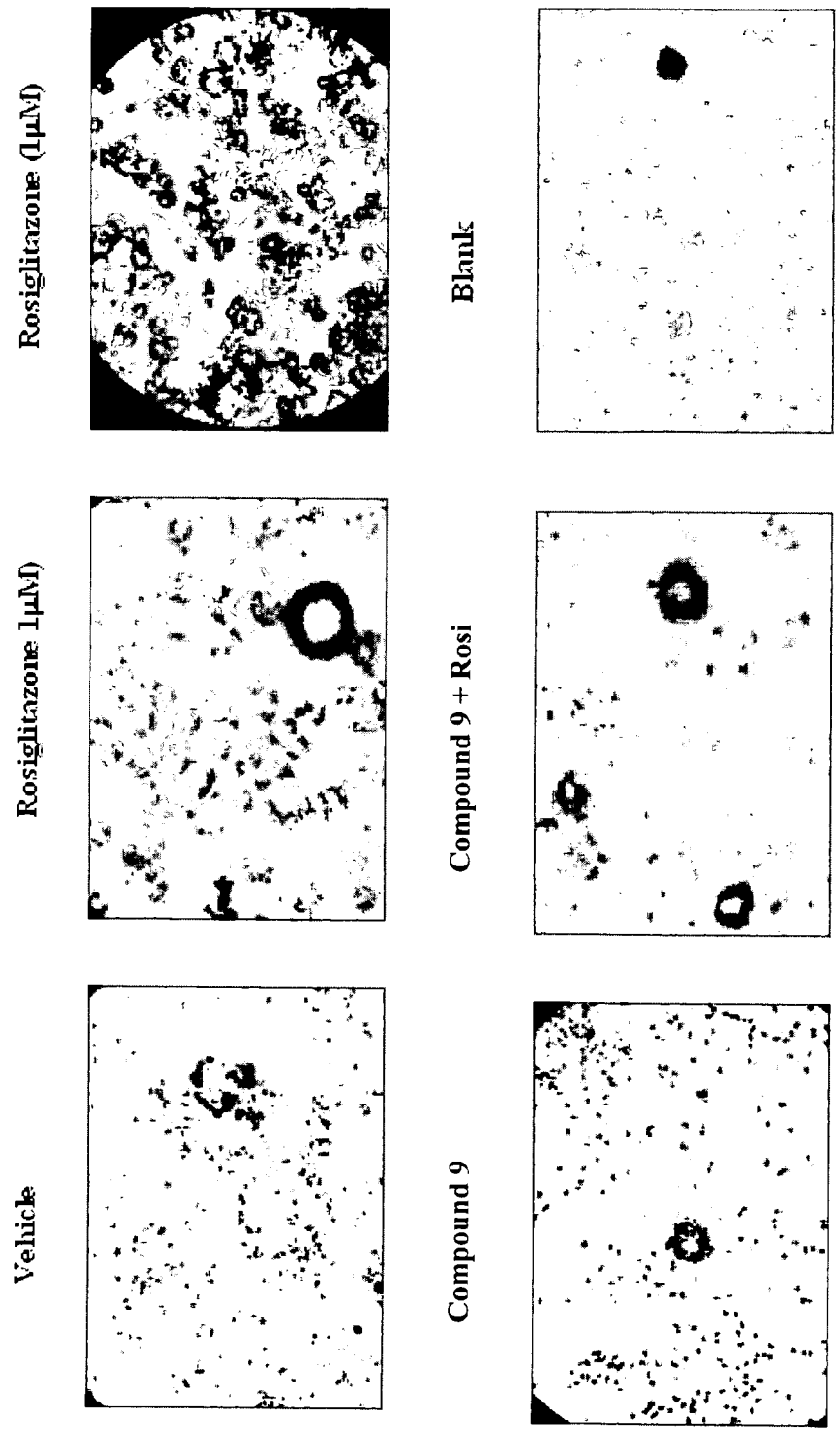
Fig 5. Inhibition of PPARγ induced adipogenesis

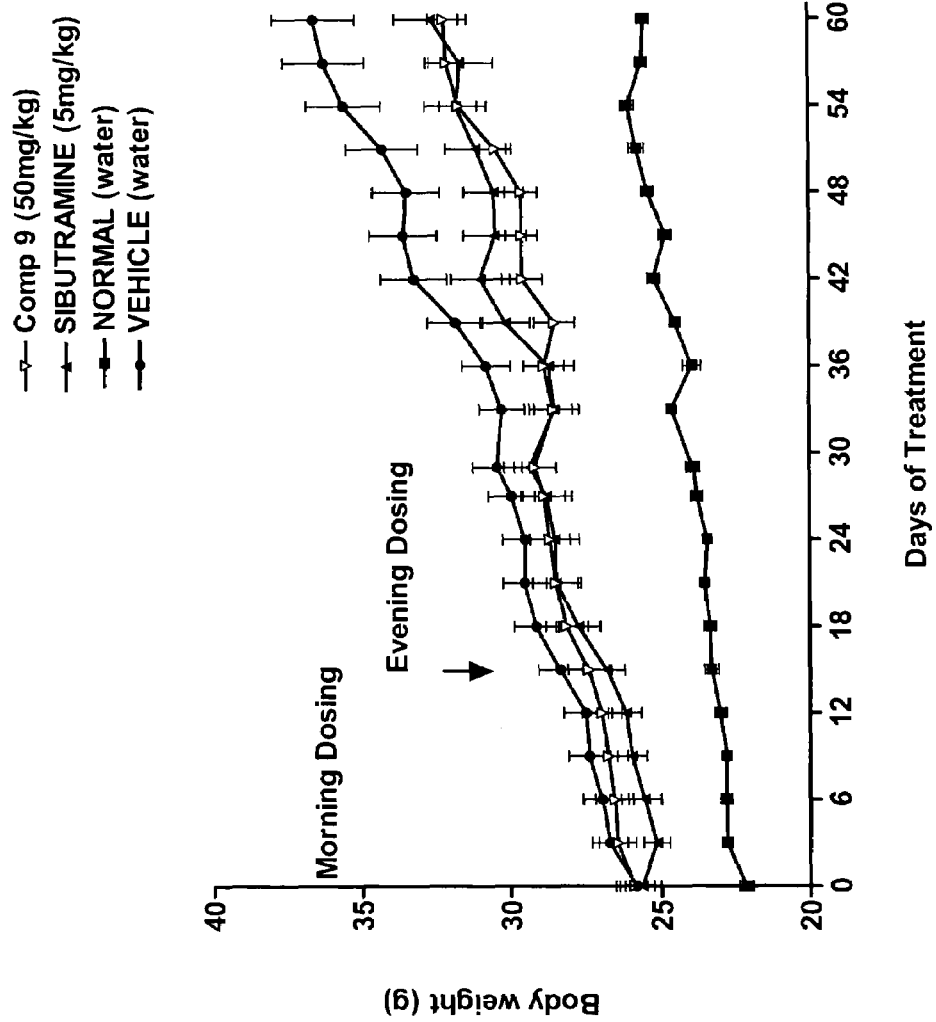
Fig 6. Comparison of body weight gain

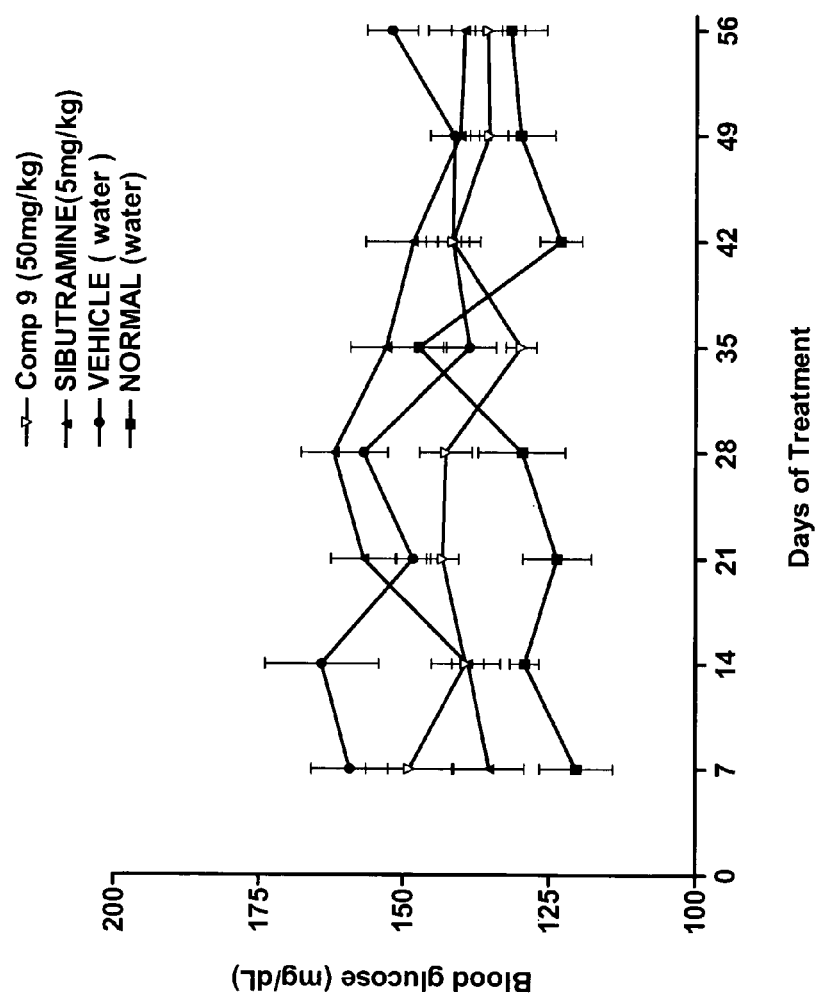
Fig 7. Hypoglycemic effect of compound 9 in DIO model

DERIVATIVES OF AMINO ACIDS FOR TREATMENT OF OBESITY AND RELATED DISORDERS

FIELD OF THE INVENTION

The present invention relates to novel amino acid derivatives, their stereoisomers, hydrates, and pharmaceutically acceptable salts and pharmaceutically acceptable compositions containing them.

BACKGROUND OF THE INVENTION

Human obesity is a recognized health problem with approximately eighty five million people considered clinically obese in the United States. Chronic imbalance between the amount of food intake and the energy expended by the body in its daily activities is the fundamental cause of obesity. The consequence of accumulation of surplus fat places overweight or obese individuals at increased risk of illness such as lipid disorders, type 2 diabetes, hypertension, migraine, coronary heart disease, stroke, osteoarthritis, respiratory problems such as chronic obstructivepulmonary disease (COPD) and asthma, sleep apnea and a wide variety of other metabolic diseases. Success in long-term treatment and/or prevention remains elusive. Obesity can be partially reversed or prevented by employing diet and behavior modification programs or by using pharmaceuticals. Among the most widely administered approved drugs are sibutramine and XENICAL®.

Sibutramine (MERIDIA®) is a CNS-active therapeutic for the treatment of obesity, which exerts its effects by acting as a norephinephime, serotonin and dopamine reuptake inhibitor. Sibutramine treatment is indicated for weight loss and is applied in combination with a reduced calorie diet. Sibutramine is contraindicated in patients with poorly controlled hypertension and patients with a history of cardiovascular heart disease.

Orlistat (XENICAL®) reduces the absorption of fatty acids by inhibition of triglyceride hydrolysis through its action as a gastric and pancreatic lipase inhibitor. Orlistat proved more effective than diet alone for weight loss, with improvements in total cholesterol, low density lipoprotein, the low density lipoprotein to high density lipoprotein ratio, and glycemic control. Side effects of Orlistat include malabsorption of fat-soluble vitamins and steatorrhea.

A variety of biological targets are under clinical evaluation for the reduction of obesity in humans. Cannabinoid receptor 1 (CB1), a G-protein coupled receptor, contributes to the control of appetite by affecting brain reward systems. Acomplia (rimonabant), a selective CB1 endocannabinoid receptor antagonist, is under development for the treatment of obesity. A selective serotonine ($5HT_{2C}$) agonist APD356 is under development for treatment of obesity.

Several selective $\beta_3$ agonists are being evaluated in clinical trials. The $\beta_3$-adrenergic receptor is found primarily in adipose tissue. It mediates a variety of metabolic functions such as lipolysis, thermogenesis and motility in the GI tract. The $\beta_3$ agonists raise cAMP levels in brown and white adipose tissue, thus leading to activation of hormone-sensitive lipase and resulting in increased fatty acid oxidation and increased thermogensis by activation of UCP in brown adipose tissue.

Research addressing the potential role of leptin in the treatment of human obesity is ongoing. Leptin is produced in adipocytes and secreted in concentration proportional to the amount of adipose tissue. Obesity in humans is generally associated with high leptin levels. Daily subcutaneous injections of recombinant leptin results in weight loss as fat mass in some obese individuals.

Receptor subunits for the neurocytokine ciliary neurotrophic factor (CNTF) share sequence similarity with the receptor for leptin. Axokine is a modified CNTF. CNTF had been shown to affect appetite and body weight in rodents otherwise resistant to leptin treatment. When subcutaneously administered to humans, CNTF significantly affected appetite and body weight. A potential concern with the use of CNTF relates to a dose-dependent activation of latent herpes simplex infection.

Inducible nitric oxide synthase (iNOS) mediated NO overproduction causes insulin resistance in obese diabetic mice (Pilon et al., *J. Biol. Chem.*, 2004, 279, 20767-74). Nitric oxide (NO) is a free radical that mediates several diverse biological events. Nitric oxide has a central role in the physiology and pathophysiology of the immune, central nervous and cardiovascular systems. The reactivity of NO toward molecular oxygen, thiols, transition metal centers and other biological targets enable it to act as a signal transduction molecule. Thus it controls diverse biological functions and is thought to be involved in the pathogenesis of autoimmune and inflammatory disease including septic, hemorrhagic shock, rheumatoid arthritis, osteoarthritis, inflammatory bowel disease, multiple sclerosis and disruption of the insulin signaling pathway (Kapur et al., *Diabetes*, 1997, 46, 1691).

Inducible NOS (iNOS) is induced by inflammatory cytokines in skeletal muscle and fat. The iNOS expression is increased in muscle and fat of genetic and dietary models of obesity. The iNOS induction in obese wild-type mice was associated with impairments in phosphatidylinositol 3-kinase and Akt activation by insulin in muscle. These defects were fully prevented in obese NOS-2$^+$ mice. These findings provide some evidence that iNOS is involved in the development of muscle insulin resistance in diet-induced obesity (Perreault and Marette, *Nature Med.*, 2001, 7, 1138). Interestingly it was observed that iNOS inhibitors do not block adjuvant arthritis in rats (Fletcher et al., *J. Pharm. Exp. Ther.*, 1998, 284, 714).

Obesity-linked diabetes is also associated with a cytokine-mediated acute-phase or stress response, as reflected by increased systemic and tissue concentrations of the pro-inflammatory cytokines tumor necrosis factor (TNF)-$\alpha$ and interleukin (IL)-6 in obese human subjects and several animal models of obesity (Hotamisligil and Spiegelman, *Diabetes*, 1994, 43, 1271). TNF-$\alpha$ might be a mediator of insulin resistance in obesity since it interferes with insulin action and signaling in both skeletal muscle and adipose tissue. Other inflammatory cytokines such as IL-1, -6 and interferon (IFN)-$\gamma$ have been also reported to inhibit insulin signaling in cultured adipose cells.

The agonists of the nuclear hormone receptor PPAR show strong bodyweight gain in obese diabetic model. These compounds cause fluid retention and adipogenesis (fat accumulation) in fibroblasts cells and result in fat laden adipocytes. It has been hypothesized that an antagonist of PPAR$\gamma$, which blocks specifically the PPAR$\gamma$ induced fat accumulation, can be useful for the treatment of obesity (Mukherjee et al., *Mol Endo*, 2000, 14, 1425)). It was observed that some of the agonist also blocks the PPAR$\gamma$ induced adipogenesis in 3T3-L1 fibroblasts.

SUMMARY OF THE DISCLOSURE

The present invention relates to novel amino acids derivatives of the general formula (1)

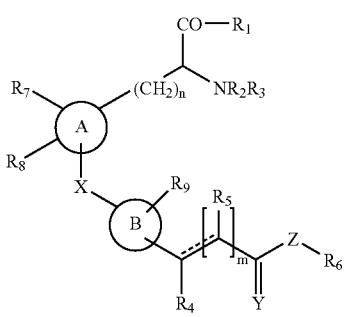

(I)

The present invention also relates to processes for the preparation of compounds of formula (I), their derivatives, stereoisomers, pharmaceutically acceptable salts and pharmaceutical compositions containing them wherein - - - represents, optionally, a bond or no bond;

A is selected from substituted or unsubstituted 5 to 18-membered aryl or heterocyclyl, including, but not limited to, phenyl, indolyl and imidazolyl;

B represents a ring system selected form substituted or unsubstituted 5 to 18-membered aryl, 5 to 6 membered saturated or unsaturated heterocyclyl having 1-4 hetero atoms selected from N, O and S;

$R_1$ represents —$OR^{10}$ where $R^{10}$ represents hydrogen, substituted or unsubstituted groups selected from alkyl, alkenyl, aryl, aralkyl, heteroaryl, or a counter ion; $NR^{11}R^{12}$, where $R^{11}$ and $R^{12}$ may be same or different and independently represent H, substituted or unsubstituted groups selected from alkyl, alkenyl or aryl; or $R^{11}$ and $R^{12}$ together with nitrogen may represent a substituted or unsubstituted mono or bicyclic saturated or unsaturated ring system which may contain one or more heteroatoms selected from O, S or N;

$R_2$ and $R_3$ may be same or different and independently represent H, $COR^{13}$, substituted or unsubstituted groups selected from alkyl, alkenyl, aryl, heteroaryl, alkylsufonyl, alkylsulfinyl, arylsulfonyl, arylsulfinyl, alkylthio, arylthio or heterocyclyl;

where $R^{13}$ represents H, substituted or unsubstituted groups selected from alkyl, aryl, alkenyloxy, aryloxy, alkoxy or aralkoxy;

$R_4$ represents hydrogen, substituted or unsubstituted groups selected from alkyl, aryl, heteroaryl, heterocyclyl or araalkyl;

$R_5$ represents H, halogen, nitro, cyano, formyl, amino, substituted or unsubstituted groups selected from alkyl, alkenyl, haloalkyl, alkoxy, aryl, heteroaryl, heterocyclyl, monoalkylamino, dialkylamino, alkanoyl, carboxylic acids or its derivatives;

Z represents O, S or $NR^{14}$, $R^{14}$ represents hydrogen or alkyl; when Z represents O or S, $R^6$ represents hydrogen or substituted or unsubstituted groups selected from alkyl, alkenyl, aryl, aralkyl, cycloalkyl, heteroaryl, heteroaralkyl, heterocyclyl; when Z represents $NR^{14}$, $R_6$ represents H, hydroxy, hydroxyl protecting groups, amino, substituted or unsubstituted groups selected from alkyl, haloalkyl, alkenyl, monoalkylamino, dialkylamino, alkoxy, aryloxy, aryl, aralkyl, cycloalkyl, heteroaryl, heteroaralkyl or heterocyclyl;

Y represents O, S or $NR^{14}$;

m is an integer from 0 to 8;

n is an integer in the range of 0 to 4;

$R_7$, $R_8$, and $R_9$ may be same or different and represent hydrogen, nitro, nitrile, hydroxy, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acids and their derivatives;

X represents a bond, O, S, SO or $SO_2$.

The compounds of the present invention are useful for management of disorders such as obesity and immunological diseases, particularly those mediated by inducible nitric oxide synthase (iNOS) and pro-inflammatory cytokines (such as TNF-α, IL-1β and IL-6). The compounds of the present invention are also useful in lowering of blood glucose levels in hyperglycemic disorders such as diabetes mellitus and for treating related disorders such as body weight gain; hyperlipidemia; abnoral serum insulin levels; elevated free fatty acid, cholesterol or triglyceride levels; and disorders exacerbated by obesity, such as migraine and respiratory problems, such as, chronic obstructive pulmonary disease and asthma.

BRIEF DESCRIPTION OF THE FIGURES

FIG. 1 is a group of two bar graphs showing the inhibition of TNF-α in human peripheral blood monocyte cells by seven different compounds of the invention.

FIG. 2 is a group of two bar graphs showing inhibition of IL-6 and IL-1β in human peripheral blood monocyte cells by a compound of the invention.

FIG. 3 is a Western blot showing inhibition of iNOS expression by a compound of the invention.

FIG. 4 is a bar graph showing the inhibition of LPS-induced NO by a compound of the invention in mouse peritoneal macrophages.

FIG. 5 is a group of six photographs showing inhibition of PPARγ agonist-induced adipocyte differentiation in fibroblast cells by a compound of the invention.

FIG. 6 is a graph showing the reduction of body weight gain in high fat-induced obesity in a mouse model by a compound of the invention.

FIG. 7 is a graph showing the hypoglycemic affect of a compound of the invention in normal lean mice.

DETAILED DESCRIPTION OF THE INVENTION

As used in the present specification, the following words and phrases are generally intended to have the meanings as set forth below, except to the extent that the context in which they are used indicates otherwise.

"Alkyl" is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like.

"Alkylene" is another subset of alkyl, referring to the same residues as alkyl, but having two points of attachment. Examples of alkylene include ethylene (—$CH_2CH_2$—), propylene (—CH$_2$CH$_2$CH$_2$—), dimethylpropylene (—CH$_2$C(CH$_3$)$_2$CH$_2$—) and cyclohexylpropylene (—CH$_2$CH$_2$CH(C$_6$H$_{13}$)—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 6 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "amino" refers to the group —NH$_2$. The term "substituted amino" refers to the mono- or di-substituted group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" and "heteroaryl" mean a 5 to 18-membered ring. Examples include a 5-, 6- or 7-membered aromatic or heteroaromatic ring containing 0-4 heteroatoms selected from O, N or S; a bicyclic 9- or 10-membered aromatic or heteroaromatic ring system containing 0-4 (or more) heteroatoms selected from O, N or S; or a tricyclic 12- to 14-membered aromatic or heteroaromatic ring system containing 0-4 (or more) heteroatoms selected from O, N or S. The aromatic carbocyclic rings include, e.g., phenyl, naphthalene, indane, tetralin, and fluorene and the aromatic heterocyclic rings include, e.g., imidazole, oxazole, isoxazole, oxadiazole, pyridine, indole, thiophene, benzopyranone, thiazole, furan, benzimidazole, quinoline, isoquinoline, quinoxaline, pyrimidine, pyrazine, tetrazole and pyrazole.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" means a cycloalkyl residue of 5 to 14 carbon atoms in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, oxadiazole, dioxane, tetrahydrofuran and the like.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carbalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. If a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" or "effective amount" refers to that amount of a compound that is sufficient to effect treatment, as defined below, when administered to a mammal including humans, in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease in a mammal, including:
a) preventing the disease, that is, causing the clinical symptoms of the disease not to develop;
b) inhibiting the disease, that is, slowing or arresting the development of clinical symptoms; and/or
c) relieving the disease, that is, causing the regression of clinical symptoms.

The term "analogs" refers to a set of compounds which differ from one another only by replacement of one or more heteroatoms, such as O, S, or N, with a different heteroatom.

The term "tautomer forms" refers to structural isomers in rapid equilibrium, such as keto and enol forms of acetylacetone. Tautomer forms are capable of reacting according to either form.

The term "polymorphs" refers to the forms of a polymorphic compound. A polymorphic compound is that which can exist in two or more forms, such as two or more crystalline forms.

The term "derivative" refers to a compound obtained from another compound by a simple chemical process; e.g., acetic acid is a derivative of ethanol by oxidation; N-acetyl ethylamine is a derivative of ethylamine by acetylation.

In formula (I), suitable groups represented by A include substituted or unsubstituted phenyl, pyridinyl, indolyl, diazinyl and imidazolyl.

Suitable groups represented by B include aryl, such as phenyl, naphthyl and the like, which may be further substituted by a substituted or unsubstituted 5 to 6 membered saturated or unsaturated heterocyclic ring is selected from pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, and the like. A useful class of compounds includes those in which B is phenyl, thiazolyl or pyridinyl.

A suitable class of compounds includes those in which $R_1$ is dialkylamino, amino, i-propoxyl, hydroxyl, benzyloxyl, N-acetyl-perhydro-1,4-dithiaindinyl or perhydro-1,4-oxazaindinyl.

Suitable groups represented by $R_2$ and $R_3$ include H, $COR^{13}$, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; substituted or unsubstituted aryl such as phenyl, naphthyl and the like; substituted or unsubstituted alkylsulfonyl group such as methylsulfonyl, ethylsulfonyl, n-propylsulfonyl, iso-propylsulfonyl and the like; substituted or unsubstituted arylsulfonyl group such as phenylsulfonyl, tolylsulfonyl, or naphthylsulfonyl; substituted or unsubstituted alkylsulfinyl group such as methylsulfinyl, ethylsulfinyl, n-propylsulfinyl, iso-propylsulfinyl and the like; substituted or unsubstituted arylsulfinyl group such as phenylsulfinyl or naphthylsulfinyl; substituted or unsubstituted alkylthio group such as methylthio, ethylthio, n-propylthio, iso-propylthio and the like; substituted or unsubstituted arylthio group such as phenylthio, or naphthylthio; substituted or unsubstituted heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like; substituted or unsubstituted heterocyclyl group such as pyrrolidinyl, morpholinyl, thiomorpholinyl, piperidinyl, piperazinyl, and the like, which may be substituted; heterocyclyl group such as pyrrolidinyl, morpholinyl, thiomorpholinyl, piperidinyl, piperazinyl, and the like. A suitable class of compounds includes those in which $R_3$ is hydrogen or p-toluenesulfonyl.

Suitable groups represented by $R_4$ include H; substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted aryl such as phenyl, naphthyl and the like; substituted or unsubstituted heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like; substituted or unsubstituted heterocyclyl group such as pyrrolidinyl, morpholinyl, thiomorpholinyl, piperidinyl, piperazinyl, and the like; and substituted or unsubstituted aralkyl group such as benzyl, phenyl ethyl, phenyl propyl and the like.

Suitable groups represented by $R_5$ include H, halogen atom such as fluorine, chlorine, bromine or iodine; hydroxy, nitro, cyano, formyl, amino, unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; substituted or unsubstituted haloalkyl such as chloromethyl, chloroethyl, trifluoromethyl, trifluoroethyl, dichloromethyl, dichloroethyl, trichloromethyl, difluoromethyl, and the like; substituted or unsubstituted alkoxy group such as methoxy, ethoxy, n-propoxy, isopropoxy and the like; substituted or unsubstituted monoalkylamino group such as —$NHCH_3$, —$NHC_2H_5$, —$NHC_3H_7$, —$NHC_6H_{13}$, and the like; substituted or unsubstituted dialkylamino group such as —$N(CH_3)_2$, —$NCH_3(C_2H_5)$, —$N(C_2H_5)_2$ and the like; substituted or unsubstituted alkanoyl group such as —$C(=O)CH_3$, —$C(=O)C_2H_5$, —$C(=O)C_3H_7$, —$C(=O)C_6H_{13}$, benzoyl, —$C(=S)CH_3$, —$C(=S)C_2H_5$, —$C(=S)C_3H_7$, —$C(=S)C_6H_{13}$ and the like; substituted or unsubstituted aryl such as phenyl, naphthyl and the like; substituted or unsubstituted heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like; substituted or unsubstituted heterocyclyl group such as pyrrolidinyl, morpholinyl, thiomorpholinyl, piperidinyl, piperazinyl, and the like; carboxylic acids or their derivatives such as esters or amides. A suitable class of compounds includes those in which $R_2$, $R_4$ and $R_5$ are hydrogen.

Suitable groups represented by $R_6$ include H, hydroxy, protected hydroxyl groups which may be ethers, esters substituted benzyl ethyl ethers and the like, amino, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; substituted or unsubstituted alkoxy group such as methoxy, ethoxy, n-propoxy, isopropoxy and the like; substituted or unsubstituted aryloxy such as phenoxy, naphthyloxy and the like; substituted or unsubstituted haloalkyl such as chloromethyl, chloroethyl, trifluoromethyl, trifluoroethyl, dichloromethyl, dichloroethyl, trichloromethyl, difluoromethyl, and the like; substituted or unsubstituted monoalkylamino group such as —$NHCH_3$, —NHC$_2$H$_5$, —NHC$_3$H$_7$, —NHC$_6$H$_{13}$, and the like; substituted or unsubstituted dialkylamino group such as —N(CH$_3$)$_2$, —NCH$_3$(C$_2$H$_5$), —N(C$_2$H$_5$)$_2$ and the like; substituted or unsubstituted aryl such as phenyl, naphthyl and the like; substituted or unsubstituted aralkyl group such as benzyl, phenyl ethyl, phenyl propyl and the like; substituted or unsubstituted cyclo (C$_3$-C$_6$) alkyl group such as cyclopropyl, cyclobutyl, cyclopentyl, cyclohexyl and the like; substituted or unsubstituted heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like; substituted or unsubstituted heterocyclyl group such as pyrrolidinyl, morpholinyl, thiomorpholinyl, piperidinyl, piperazinyl, and the like; heteroaralkyl, wherein the heteroaryl portion is as defined above. A suitable class of compounds includes those in which R$_6$ is hydroxyl, alkyl, hydrogen or dialkylmethyl.

Suitable groups represented by R$_7$, R$_8$, and R$_9$ include H, nitro, nitrile, hydroxy, formyl, azido, halogen atom such as fluorine, chlorine, bromine or iodine; substituted or unsubstituted linear or branched C$_1$-C$_{20}$ alkyl group such as methyl, ethyl, n-propyl, isopropyl, n-butyl, isobutyl, t-butyl, n-pentyl, isopentyl, hexyl and the like; substituted or unsubstituted alkoxy group, such as methoxy, ethoxy, n-propoxy, isopropoxy and the like; substituted or unsubstituted acyl group such as —C(=O)CH$_3$, —C(=O)C$_2$H$_5$, —C(=O)C$_3$H$_7$, —C(=O)C$_6$H$_{13}$, benzoyl, —C(=S)CH$_3$, —C(=S)C$_2$H$_5$, —C(=S)C$_3$H$_7$, —C(=S)C$_6$H$_{13}$ and the like; substituted or unsubstituted cyclo (C$_3$-C$_6$) alkyl group such as cyclopropyl, cyclobutyl, cyclopentyl, cyclohexyl and the like; substituted or unsubstituted haloalkyl such as chloromethyl, chloroethyl, trifluoromethyl, trifluoroethyl, dichloromethyl, dichloroethyl, trichloromethyl, difluoromethyl, and the like; substituted or unsubstittued amino, which may be substituted; hydrazine, monoalkylamino group such as —NHCH$_3$, —NHC$_2$H$_5$, —NHC$_3$H$_7$, —NHC$_6$H$_{13}$; substituted or unsubstittued dialkylamino group such as —N(CH$_3$)$_2$, —NCH$_3$(C$_2$H$_5$), —N(C$_2$H$_5$)$_2$ and the like; substituted or unsubstituted acylamino group such as —NHC(=O)CH$_3$, —NHC(=O)C$_2$H$_5$, —NHC(=O)C$_3$H$_7$, —NHC(=O)C$_6$H$_{13}$, and the like; substituted or unsubstittued alkylsulfonyl group such as methylsulfonyl, ethylsulfonyl, n-propylsulfonyl, iso-propylsulfonyl and the like; substituted or unsubstituted arylsulfonyl group such as phenylsulfonyl or naphthylsulfonyl; substituted or unsubstituted alkylsulfinyl group such as methylsulfinyl, ethylsulfinyl, n-propylsulfinyl, iso-propylsulfinyl and the like; arylsulfinyl group such as phenylsulfinyl or naphthylsulfinyl, the arylsulfinyl group may be substituted; substituted or unsubstituted alkylthio group such as methylthio, ethylthio, n-propylthio, iso-propylthio and the like; substituted or unsubstituted arylthio group such as phenylthio, or naphthylthio; substituted or unsubstituted alkoxycarbonyl group such as methoxycarbonyl, ethoxycarbonyl, n-propoxycarbonyl, isopropoxycarbonyl and the like; substituted or unsubstituted aryloxycarbonyl group such as phenoxycarbonyl, napthoxycarbonyl; substituted or unsubstituted alkoxyalkyl group such as methoxymethyl, ethoxymethyl, methoxyethyl, ethoxyethyl and the like; sulfamoyl, carboxylic acids or their derivatives. A suitable group of compounds includes those in which R$_7$, R$_8$ and R$_9$ are hydrogen.

Suitable groups represented by R$^{10}$ include H, substituted or unsubstituted linear or branched C$_1$-C$_{20}$ alkyl group such as methyl, ethyl, n-propyl, isopropyl, n-butyl, isobutyl, t-butyl, n-pentyl, isopentyl, hexyl and the like; substituted or unsubstituted linear or branched C$_2$-C$_{20}$ alkenyl such as ethenyl, propenyl, butenyl and the like; substituted or unsubstituted aryl such as phenyl, naphthyl and the like; substituted or unsubstituted aralkyl group such as benzyl, phenyl ethyl, phenyl propyl and the like; substituted or unsubstittued heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like; counter ions selected from alkali metals such as Li, Na, and K; alkaline earth metal such as Ca and Mg; salts of bases such as ammonium or substituted ammonium salts, diethanolamine, α-phenylethylamine, benzylamine, piperidine, morpholine, pyridine, hydroxyethylpyrrolidine, hydroxyethylpiperidine, choline and the like, aluminum, tromethamine and the like.

Suitable groups represented by R$^{11}$ and R$^{12}$ include H, substituted or unsubstituted linear or branched C$_1$-C$_{20}$ alkyl group such as methyl, ethyl, n-propyl, isopropyl, n-butyl, isobutyl, t-butyl, n-pentyl, isopentyl, hexyl and the like; substituted or unsubstituted linear or branched C$_2$-C$_{20}$ alkenyl such as ethenyl, propenyl, butenyl and the like; substituted or unsubstituted aryl such as phenyl, naphthyl and the like; C$_1$-C$_{20}$ alkanoyl group such as —C(=O)CH$_3$, —C(=O)C$_2$H$_5$, —C(=O)C$_3$H$_7$, —C(=O)C$_6$H$_{13}$, benzoyl, —C(=S)CH$_3$, —C(=S)C$_2$H$_5$, —C(=S)C$_3$H$_7$, —C(=S)C$_6$H$_{13}$ and the like; C$_1$-C$_{20}$ alkylamido; or R$^{11}$ and R$^{12}$ together with nitrogen may represent substituted or unsubstituted mono or bicyclic saturated or unsaturated ring system selected from substituted or unsubstituted pyridyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl, pyrrolidinyl, morpholinyl, thiomorpholinyl, piperidinyl, piperazinyl and the like. The substituents are selected from nitro, hydroxy, halo, formyl, azido, alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acids or their derivatives where R$^{13}$ represents H, substituted or unsubstituted groups selected from H, substituted or unsubstituted linear or branched alkyl, aryl, alkenyloxy, aryloxy, alkoxy or aralkoxy group. Suitable groups represented by R$^{13}$ include C$_1$-C$_{20}$ alkyl, such as methyl, ethyl, n-propyl, isopropyl, n-butyl, isobutyl, t-butyl, n-pentyl, isopentyl, hexyl and the like; substituted or unsubstituted aryl such as phenyl, naphthyl and the like; substituted or unsubstituted linear or branched C$_2$-C$_{20}$ alkenoxy such as ethenoxy, propenoxy, butenoxy and the like; substituted or unsubstituted aryloxy such as phenoxy, naphthoxy and the like; substituted or unsubstituted alkoxy group, such as methoxy, ethoxy, n-propoxy, isopropoxy and the like; substituted or unsubstituted aralkoxy group such as benzyloxy, phenyl ethoxy, phenyl propoxy and the like.

Suitable groups represented by R$^{13}$ include H; unsubstituted linear or branched C$_1$-C$_{20}$ alkyl group such as methyl, ethyl, n-propyl, isopropyl, n-butyl, isobutyl, t-butyl, n-pentyl, isopentyl, hexyl and the like; substituted or unsubstituted aryl such as phenyl, naphthyl and the like; substituted or unsubstituted linear or branched C$_2$-C$_{20}$ alkenyloxy such as ethenyoxyl, propenyloxy, butenyloxy and the like; substituted or unsubstituted alkoxy group such as methoxy, ethoxy, n-propoxy, isopropoxy and the like; substituted or unsubstituted aryloxy such as phenoxy, naphthyloxy and the like; or substituted or unsubstituted araloxy group such as benzoxy, phenyl ethoxy, phenyl propoxy and the like.

Suitable groups represented by $R^{14}$ include H and substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like.

Suitable groups represented by X include a bond, O, S, SO and $SO_2$. Suitable compounds include those in which X is a bond or O.

Suitable groups represented by Y include O, S and $NR^{14}$. Suitable compounds include those in which Y is O.

Suitable m is an integer of 0 to 8. Compounds in which m is 0 or 1 are particularly suitable.

Suitable n is an integer of 0 to 4. Compounds in which n is 0, 1 or 2 are particularly suitable.

Suitable groups represented by Z include O, S and NH. Compounds in which Z is NH or O are particularly suitable.

Pharmaceutically acceptable salts of the present invention include salts with counterions of an alkali metal such as Li, Na, and K, an alkaline earth metal such as Ca and Mg, salts of organic bases such as diethanolamine, α-phenylethylamine, benzylamine, piperidine, morpholine, pyridine, hydroxyethylpyrrolidine, hydroxyethylpiperidine, choline and the like, ammonium or substituted ammonium salts and aluminum salts. Salts also include those with counterion amino acid salts such as glycine, alanine, cystine, cysteine, lysine, arginine, phenylalanine, guanidine etc. Salts may include acid addition salts where appropriate such as sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprise other solvents of crystallization such as alcohols.

The following compounds are representative of the preferred compounds according to Formula (I):

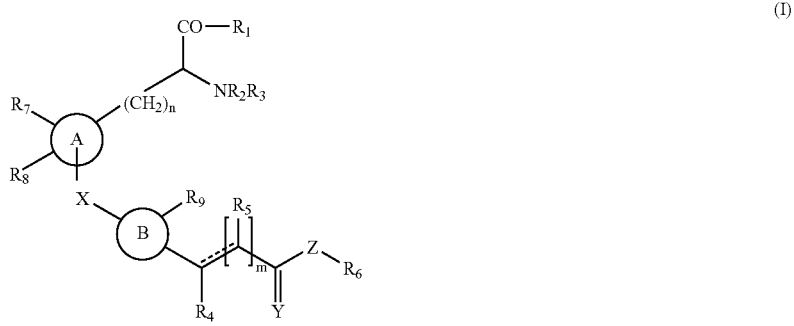

| $R^1$ | $R^2$ | $R^3$ | $R^4$ | $R^5$ | $R^6$ | $R^7$ | $R^8$ | $R^9$ | X | Y | m | Z | n | A | B |
|---|---|---|---|---|---|---|---|---|---|---|---|---|---|---|---|
| —N(CH$_3$)$_2$ | H | H | H | H | OH | H | H | H | Bond | O | 1 | NH | 1 | no bond | Ph | Ph |
| —NH$_2$— | H | H | H | H | OH | H | H | H | Bond | O | 1 | NH | 1 | no bond | Ph | Ph |
| —NH$_2$— | H | H | H | H | OH | H | H | H | O | O | 1 | NH | 1 | no bond | Ph | Ph |
| —N(CH$_3$)$_2$ | H | H | H | H | OH | H | H | H | O | O | 1 | NH | 1 | no bond | Ph | Ph |
| —N(CH$_3$)$_2$ | H | H | H | H | OH | H | H | H | Bond | O | 1 | NH | 1 | no bond | Ph | Py |
| —NH$_2$— | H | H | H | H | OH | H | H | H | Bond | O | 1 | NH | 1 | no bond | Ph | Py |
| —NH$_2$— | H | H | H | H | OH | H | H | H | O | O | 1 | NH | 1 | no bond | Py | Ph |
| —N(CH$_3$)$_2$ | H | H | H | H | OH | H | H | H | O | O | 1 | NH | 1 | no bond | Py | Ph |
| —N(CH$_3$)$_2$ | H | H | H | H | OH | H | H | H | Bond | O | 1 | NH | 1 | no bond | Ph | 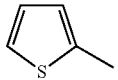 |
| —NH$_2$— | H | H | H | H | OH | H | H | H | Bond | O | 1 | NH | 2 | no bond | Ph | Ph |
| —NH$_2$— | H | H | H | H | OH | H | H | H | O | O | 1 | NH | 2 | no bond | Ph | Ph |
| —N(CH$_3$)$_2$ | H | H | H | H | OH | H | H | H | O | O | 1 | NH | 2 | no bond | Ph | Ph |
| —N(CH$_3$)$_2$ | H | H | H | H | OH | H | H | H | Bond | O | 1 | NH | 2 | no bond | Py | Ph |
| —NH$_2$— | H | H | H | H | OH | H | H | H | Bond | O | 1 | NH | 2 | no bond | Py | Ph |
| —NH$_2$— | H | H | H | H | OH | H | H | H | O | O | 1 | NH | 2 | no bond | Py | Ph |
| —N(CH$_3$)$_2$ | H | H | H | H | OH | H | H | H | O | O | 1 | NH | 2 | no bond | Py | Ph |
| —N(CH$_3$)$_2$ | H | H | H | H | OH | H | H | H | Bond | O | 1 | NH | 1 | bond | Ph | 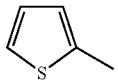 |
| —NH$_2$— | H | H | H | H | OH | H | H | H | Bond | O | 1 | NH | 1 | bond | Ph | Ph |
| —NH$_2$— | H | H | H | H | OH | H | H | H | O | O | 1 | NH | 1 | bond | Ph | Ph |
| —N(CH$_3$)$_2$ | H | H | H | H | OH | H | H | H | O | O | 1 | NH | 1 | bond | Ph | Ph |
| —N(CH$_3$)$_2$ | H | H | H | H | OH | H | H | H | Bond | O | 1 | NH | 1 | bond | Py | Ph |
| —NH$_2$— | H | H | H | H | OH | H | H | H | Bond | O | 1 | NH | 1 | bond | Py | Ph |
| —NH$_2$— | H | H | H | H | OH | H | H | H | O | O | 1 | NH | 1 | bond | Py | Ph |
| —N(CH$_3$)$_2$ | H | H | H | H | OH | H | H | H | O | O | 1 | NH | 1 | bond | Py | Ph |

-continued

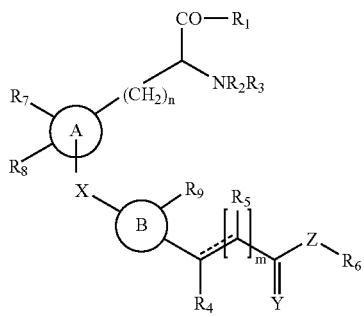
(I)

| R¹ | R² | R³ | R⁴ | R⁵ | R⁶ | R⁷ | R⁸ | R⁹ | X | Y | m | Z | n | ----- | A | B |
|---|---|---|---|---|---|---|---|---|---|---|---|---|---|---|---|---|
| —N(CH₃)₂ | H | H | H | H | CH₃ | H | H | H | Bond | O | 1 | NH | 1 | no bond | Ph | Ph |
| —NH₂— | H | H | H | H | CH₃ | H | H | H | Bond | O | 1 | NH | 1 | no bond | Ph | Ph |
| —N(CH₃)₂ | H | —SO₂-C₆H₄-CH₃ | H | H | OH | H | H | H | Bond | O | 1 | NH | 1 | no bond | Ph | Ph |
| —N(CH₃)₂ | H | —SO₂-C₆H₄-CH₃ | H | H | H | H | H | H | Bond | O | 1 | O | 1 | no bond | Ph | Ph |
| —N(CH₃)₂ | H | H | H | H | H | H | H | H | Bond | O | 0 | O | 1 | no bond | Ph | Ph |
| —N(CH₃)₂ | H | H | H | H | N(CH₃)₂ | H | H | H | O | O | 1 | NH | 0 | no bond | Ph | Ph |
| —N(CH₃)₂ | H | H | H | H | H | H | H | H | O | O | 1 | NH | 0 | no bond | Ph | Ph |
| —N(CH₃)₂ | H | H | H | H | H | H | H | H | O | O | 1 | O | 0 | no bond | Ph | Ph |
| —N(CH₃)₂ | H | H | H | H | OH | H | H | H | O | O | 1 | NH | 0 | no bond | Ph | Ph |
| —O-iPr | H | H | H | H | H | H | H | H | O | O | 0 | O | 1 | no bond | Ph | Ph |
| —O-iPr | H | H | H | H | OH | H | H | H | O | O | 0 | NH | 1 | no bond | Ph | Ph |
| —N(CH₃)₂ | H | —SO₂-C₆H₄-CH₃ | H | H | OH | H | H | H | Bond | O | 0 | NH | 1 | no bond | Ph | Ph |
| —N(CH₃)₂ | H | H | H | H | OH | H | H | H | O | O | 0 | NH | 1 | no bond | Ph | Ph |
| OH | H | H | H | H | OH | H | H | H | O | O | 0 | NH | 1 | no bond | Ph | Ph |
| —OCH₂Ph | H | H | H | H | OH | H | H | H | O | O | 0 | NH | 1 | no bond | Ph | Ph |

-continued

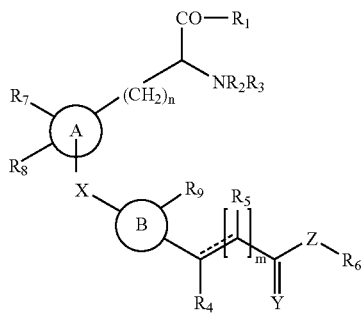

(I)

| R¹ | R² | R³ | R⁴ | R⁵ | R⁶ | R⁷ | R⁸ | R⁹ | X | Y | m | Z | n | ----- | A | B |
|---|---|---|---|---|---|---|---|---|---|---|---|---|---|---|---|---|
| —N(CH₃)₂ | H | ―SO₂―C₆H₄―CH₃ (p-tolylsulfonyl) | H | H | OH | H | H | H | O | O | 1 | NH | 1 | no bond | Ph | pyridyl |
| —N(CH₃)₂ | H | ―SO₂―C₆H₄―CH₃ (p-tolylsulfonyl) | H | H | H | H | H | H | O | O | 1 | O | 1 | no bond | Ph | pyridyl |
| piperazine-N-COCH₃ | H | H | H | H | OH | H | H | H | O | O | 1 | NH | 1 | no bond | Ph | Ph |
| morpholino | H | H | H | H | OH | H | H | H | O | O | 1 | NH | 1 | no bond | Ph | pyridyl |
| —N(CH₃)₂ | H | H | H | H | H | H | H | H | O | O | 1 | NH | 1 | no bond | Ph | pyridyl |
| —N(CH₃)₂ | H | H | H | H | H | H | H | H | O | O | 1 | O | 1 | no bond | Ph | pyridyl |
| —N(CH₃)₂ | H | H | H | H | H | H | H | H | Bond | O | 1 | NH | 1 | no bond | Ph | Ph |

-continued
(I)
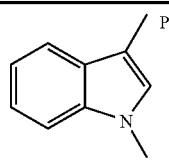
| $R^1$ | $R^2$ | $R^3$ | $R^4$ | $R^5$ | $R^6$ | $R^7$ | $R^8$ | $R^9$ | X | Y | m | Z | n | A | B |
|---|---|---|---|---|---|---|---|---|---|---|---|---|---|---|---|
| —N(CH$_3$)$_2$ | H | H | H | H | OH | H | H | H | O | O | 1 | NH | 1 | no bond | 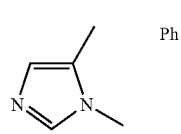 |
| —N(CH$_3$)$_2$ | H | H | H | H | OH | H | H | H | O | O | 1 | NH | 1 | no bond | 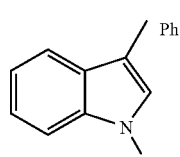 |
| —NH$_2$ | H | H | H | H | OH | H | H | H | O | O | 1 | NH | 1 | no bond | 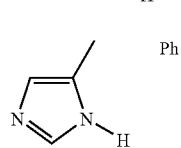 |
| —NH$_2$ | H | H | H | H | OH | H | H | H | O | O | 1 | NH | 1 | no bond | 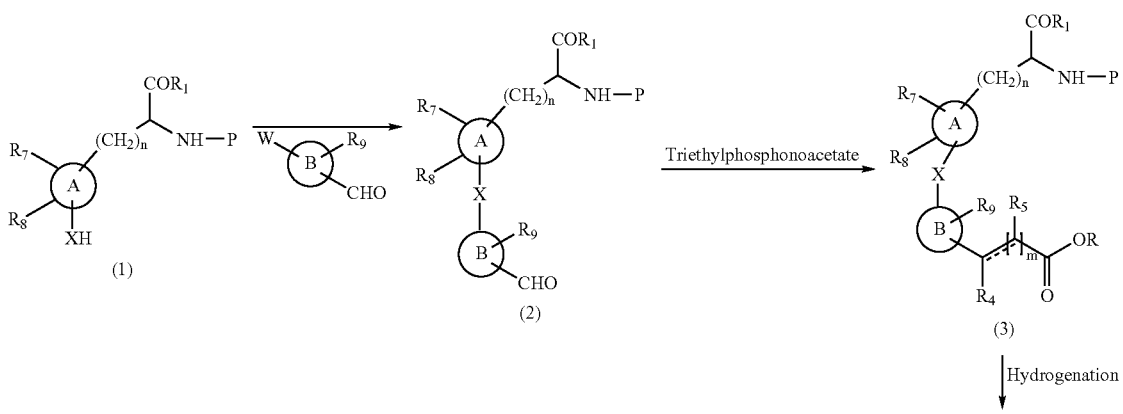 |
A process for the preparation of compounds of the general formula (I) is provided by the following scheme I.
Scheme I
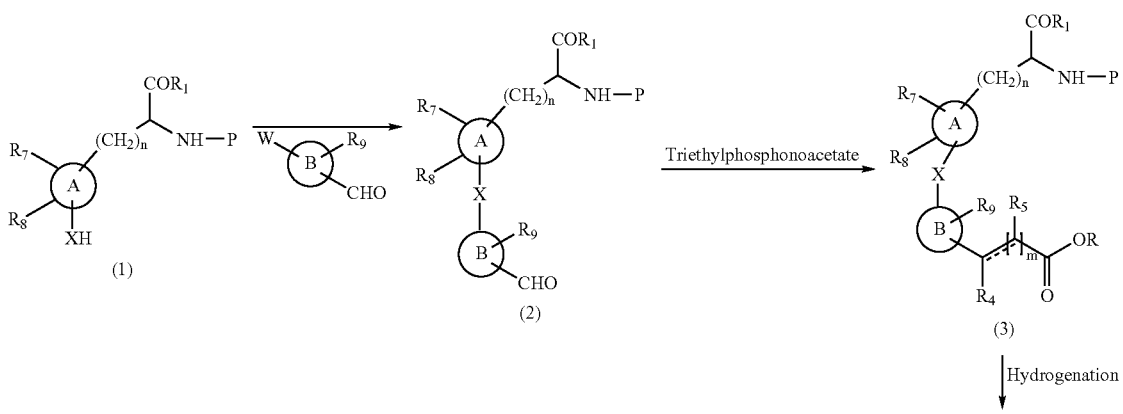

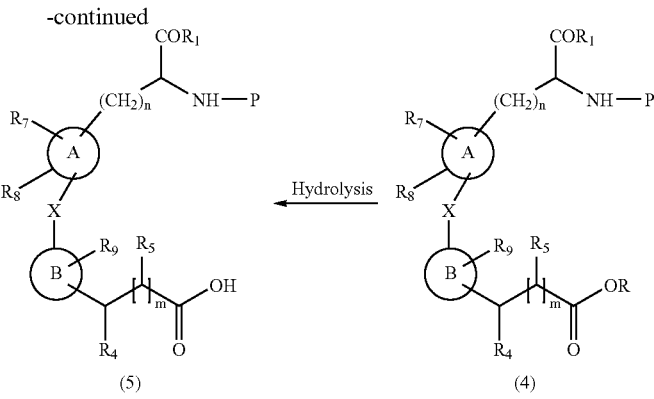
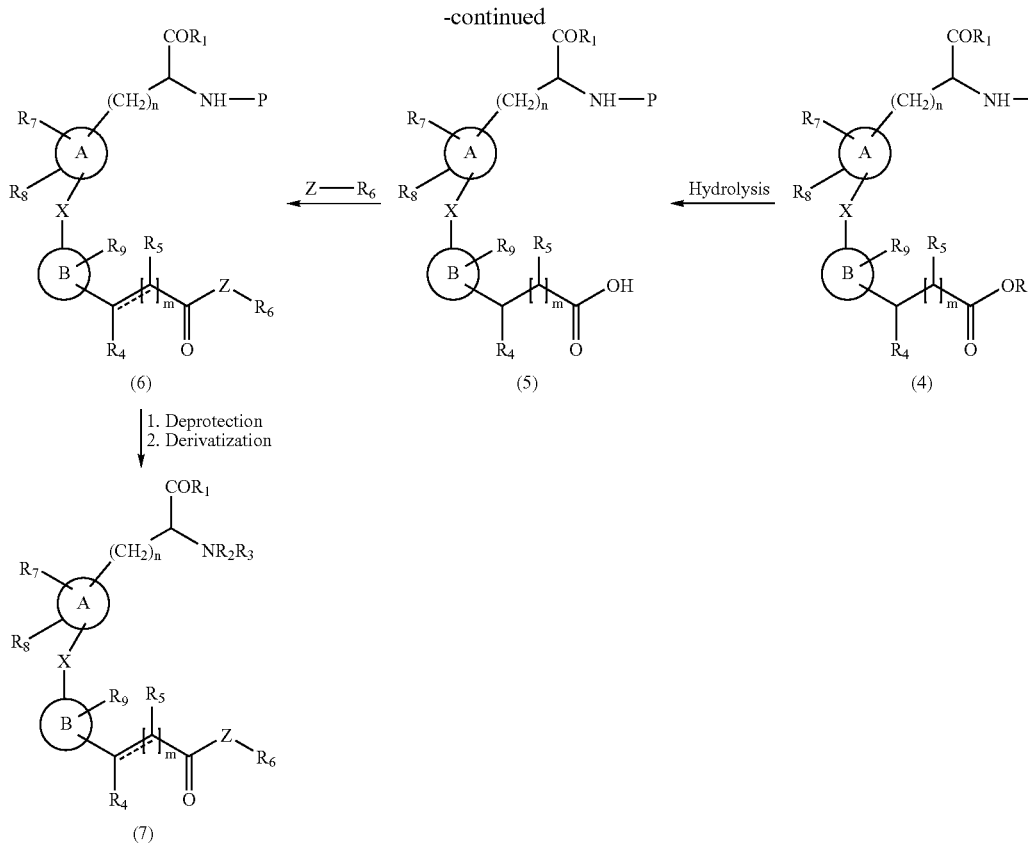

The compound of the general formula (I) is prepared by the following procedure;

Step-(I): The condensation of amino acid derivative of compound of formula (1), (wherein P represents a protecting group) with substituted halo-aldehyde (W=halo) carried out in the presence of solvents selected from toluene, DMF, tetrahydrofuran, chloroform, dichloromethane, dichloroethane, ethyl acetate, o-dichlorobenzene or a mixture thereof, in the presence of base such as triethyl amine, diethylamine, pyridine, DMAP, alkali hydroxides, alkaline earth metal hydroxide, alkali carbonates such as sodium hydroxide, potassium hydroxide, potassium carbonate and the like to obtain the compound of formula (2). The reaction is preferably carried out at a temperature in the range of room temperature to reflux temperature 0° C. to 100° C.

Step-(II): Reacting the compound of formula (2) with triethylphosphonoacetate, trimethyphosphonoacetate and the like when m=1, in the presence of sodium hydride, lithium hydride and the like in the presence of solvents such as toluene, DMF, tetrahydrofuran, dichloromethane, o-dichlorobenzene or a mixture thereof produces ester of formula (3).

Step-(III): The compound of the formula (3) is hydrogenated by using a catalyst such as Raney nickel, Pd/C, in the presence of solvents such as, methanol, ethanol, ethylacetate, n-butylacetate or a mixture thereof. The reaction may be carried out at 0° C. to 100° C. The duration of the reaction may range from 2 to 24 hrs, to produce a compound of formula (4).

Step-(IV): Desterifying the ester of formula (4) by using alkali hydroxide in the presence of solvent like THF, water, methanol or mixture thereof produces the compound of the formula (5).

Step-(V): The compound of formula (5) is reacted with $H_2N-R_6$ wherein $R_6$ is as described above in the presence of reagents selected from dicyclohexylcarbodiimide (DCC), N-hydroxysuccinimide (NHS), benzotriazol-1-yloxy-tris (dimethylamino)phosphonium hexafluorophosphate (BOP), 1-ethyl-3-(3-dimethylaminopropyl)carbodiimide (EDAC), 1-hydroxybenztriazole hydrate (HOBt) in the presence of base such as triethyl amine, pyridine, DMAP, and the like and solvents such as toluene, methanol, ethanol, tetrahydrofuran, chloroform, dichloromethane, dichloroethane, ethylacetate, o-dichlorobenzene or a mixture thereof to produce the compound of the formula (6). For making an ester (Z=O) or thioester (Z=S), a suitable activated acid form of the compound of formula (5) is used, such as an activated ester or acid halide, to react with $Z-R_6$.

Step-(VIa): The deprotection of compound of formula (6) may be carried out using Pd/C or HCl in the presence of solvents. Alternatively, the deportection may be carried out by passing HCl gas through a solvent selected from acetonitrile, dichloromethane, methanol, dimethylsulfoxide, dimethylformamide, tetrahydrofuran, trifluoro acetic acid, 1-methyl-2-pyrrolidinone, N,N-dimethylacetamide and the like or mixtures thereof.

Step-(VIb): The deprotected amide nitrogen is derivatized with $R_2$ and/or $R_3$ by conventional methods.

It is appreciated that in any of the above-mentioned reactions, any reactive group in the substrate molecule may be protected according to conventional chemical practice. Suitable protecting groups in any of the above-mentioned reactions are known in the art. The methods of formation and removal of such protecting groups are those methods appropriate to the molecule being protected.

The protecting group P used in the invention is a conventional protecting group such as t-butoxy carbonyl (t-Boc), trityl, trifluoroacetyl, benzyloxy, benzyloxy carbonyl (Cbz) and the like.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases such as lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The present invention also provides a pharmaceutical composition, containing one or more of the compounds of the general formula (I) as defined above, their their derivatives, their analogues, their stereoisomers, their pharmaceutically acceptable salts in combination with a pharmaceutically acceptable diluent and the like.

The pharmaceutical composition may be in the forms normally employed, such as tablets, capsules, powders, syrups, solutions, suspensions and the like. It may contain flavorants, sweeteners, etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical composition of the present invention are effective in the treatment of obesity, inflammation and autoimmune diseases. Furthermore, pharmaceutical composition of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, and IL-6. These compounds are also effective in the treatment of nitric oxide mediated disorders like insulin resistance, obesity, septic shock, rheumatoid arthritis, osteoarthritis, inflammatory bowel disease, multiple sclerosis and related diseases. The compounds of the present invention are also useful in lowering of blood glucose levels in hyperglycemic disorders such as diabetes mellitus and for treating related disorders such as body weight gain; abnormal serum insulin levels; elevated free fatty acid, cholesterol or triglyceride levels; and disorders exacerbated by obesity, such as migraine and respiratory problems, such as, chronic obstructive pulmonary disease and asthma.

The invention provides a method of treating metabolic disorders by administering to a subject in need of such treatment an effective amount of a compound according to Formula I.

Pharmaceutical compositions containing a therapeutically effective amount of one or more compounds according to Formula I together with a pharmaceutically or physiologically acceptable carrier, for use in the treatments contemplated herein, are also provided.

The present invention is provided by the examples below, which are provided by way of illustration only and should not be considered to limit the scope of the invention.

EXAMPLE 1

Synthesis of L-2-amino-3-{4-[4-(2-hydroxycarbamoylethyl)-phenoxy]-phenyl}-N,N-dimethylpropionamide hydrochloride(9)

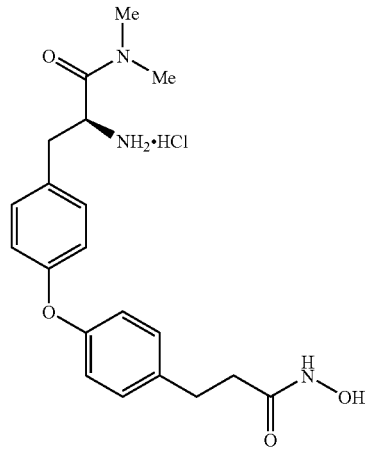

(9)

Step I

Preparation of 2-tertbutoxycarbonylamino-3-[4-(4-formylphenoxy)-phenyl]-propionic acid (2)

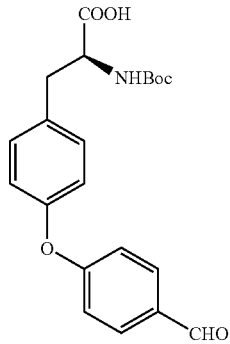

(2)

Potassium carbonate (14.74 g, 107 mmol) and 4-fluorobenzaldehyde (18.6 mL, 180 mmol) were added to a solution of amino acid (1) (10.0 g, 36 mmol) in anhydrous DMF (35 mL). The resulting suspension was refluxed at 75±5° C. under an atmosphere of argon. After 48 hr, the reaction mixture was cooled to room temperature, diluted with water (200 mL) and extracted with EtOAc (2×100 mL). The aqueous layer was collected, acidified with 5.0 M HCl to pH ~2.0 and extracted with EtOAc (2×150 mL). The resulting EtOAc layer was extracted with water (1×150 mL) and brine (1×150 mL), dried over anhydrous magnesium sulfate, filtered and concentrated under reduced pressure to yield the desired aldehyde as a low melting solid (13.7 g, ~99%). $^1$H NMR (300 MHz, DMSO-$d_6$): 9.89 (s, 1H), 7.82 (d, J=8.4 Hz, 2H), 7.23 (d, J=8.4 Hz, 2H), 7.00 (overlapped d, J=9.0 Hz, 4H), 4.63 (m, 1H), 3.2 (m, 1H), 3.06 (m, 1H), 1.40 (s, 9H).

Step II

Preparation of 3-{4-[4-(2-tert-butoxycarbonylamino-2-carboxy-ethyl)-phenoxy]-phenyl}-acrylic acid methyl ester (3)

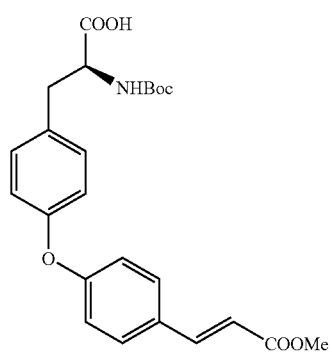

(3)

Sodium hydride (60% in mineral oil, 3.06 g, 76.0 mmol) was washed with anhydrous hexane (3×30 mL) under an atmosphere of argon. Dry THF (140 mL) was added and cooled to 0-5° C. A solution of trimethylphosphonoacetate (6.2 mL, 38.0 mmol) in dry THF (30 mL) was added dropwise to the above mixture with stirring. After about 5 min, a solution of the aldehyde 2 (13.4 g, 35.0 mmol) in dry THF (30 mL) was added and the reaction mixture was then brought up to room temperature and stirred. After 30 min, the clear reaction mixture was quenched with 10% citric acid (50 mL) and further acidified to pH ~2.0 with 2.0 M HCl. The THF was evaporated under reduced pressure and the resulting oily material was extracted with EtOAc (2×200 mL). The organic layer was extracted with water (3×200 mL), and brine (1×200 mL), dried over anhydrous magnesium sulfate, filtered and concentrated in vacuo to yield the unsaturated ester (14.0 g, 91.0%) as a crude product that was taken for the next step without further purification. $^1$H NMR (400 MHz, DMSO-$d_6$): 12.6 (s, 1H), 7.73 (d, J=8.8 Hz, 2H), 7.63 (d, J=16.0 Hz, 1H), 7.30 (d, J=8.4 Hz, 2H), 7.13 (d, J=8.8 Hz, 1H), 7.00 (d, J=8.4 Hz, 2H,), 6.96 (d, J=8.8 Hz, 2H), 6.55 (d, J=16.0 Hz, 1H), 4.11 (m, 1H), 3.03 (dd, J=14.0 and 4.4 Hz, 1H), 2.81 (dd, J=14.0 and 10.4 Hz, 1H), 1.33 (s, 9H).

Step III

Preparation of 2-tert-butoxycarbonylamino-3-{4-[4-(2-methoxycarbonyl-ethyl)-phenoxy]-phenyl}-propionic acid (4)

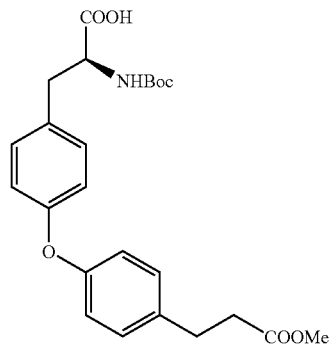

(4)

Raney nickel 2800 (15.4 g) was added to a degassed solution of the unsaturated ester 3 (14.7 g) in MeOH (100 mL) and the resulting suspension was treated with hydrogen at atmospheric pressure for 18 h. The suspension was filtered over a Celite® bed and concentrated. Flash chromatography (30-50% ethyl acetate in hexane containing 1% acetic acid) of the resulting residue gave the desired saturated ester 4 (8.1 g, 55%). $^1$H NMR (400 MHz, DMSO-$d_6$): 12.7 (br, 1H), 7.22 (overlapped d, J=8.4 Hz, 4H), 7.08 (d, J=8.0 Hz, 1H), 6.88 (overlapped d, J=8.0 Hz, 4H), 4.07 (br, 1H), 3.00 (m, 1H), 2.82 (t, J=7.6 Hz, 2H), 2.79 (m, 1H), 2.62 (t, J=8.0 Hz, 2H), 1.33 (s, 9H).

Step IV

Preparation of 3-{4-[4-(2-tert-butoxycarbonylamino-2-dimethylcarbamoyl-ethyl)-phenoxy]-phenyl}-propionic acid methyl ester (5)

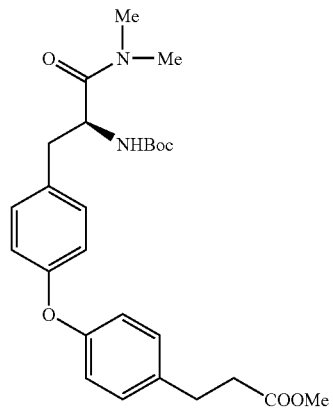

(5)

The hydrogenated compound 4 (8.0 g, 18.0 mmol) was dissolved in $CH_2Cl_2$ and stirred at room temperature under an atmosphere of argon. Triethylamine (3.02 mL, 21.6 mmol) and benzotriazol-1-yloxy-tris(dimethylamino)phosphonium hexafluorophosphate (BOP reagent, 8.78 g, 20.0 mmol) were added and the reaction mixture was stirred for 15 min. Dimethylamine (2.0 M solution in THF, 45.2 mL, 90.0 mmol) was added and the resulting solution was stirred at room temperature for about 2-3 h. The solvent was removed under reduced pressure and the resulting oil was taken up in EtOAc (200 mL). The organic layer was extracted with 0.5 N NaOH (1×30 mL), water (2×100 mL) and brine (1×100 mL). Drying and concentration of the organic layer gave the desired amide 5 (8.4 g, ~98%). $^1$H NMR (400 MHz, DMSO-$d_6$): 7.24 (d, J=8.4 Hz, 2H), 7.20 (d, J=8.4 Hz, 2H), 7.07 (d, J=8.4 Hz, 1H), 6.89 (d, J=8.8 Hz, 2H), 6.86 (d, J=8.8 Hz, 2H), 4.23 (m, 1H), 3.58 (s, 3H), 2.91 (s, 3H), 2.70-2.86 (m, 7H), 2.62 (t, J=7.6 Hz, 2H), 1.31 (s, 9H).

Step V

Preparation of 3-{4-[4-(2-tert-butoxycarbonylamino-2-dimethylcarbamoyl-ethyl)-phenoxy]-phenyl}-propionic acid (6)

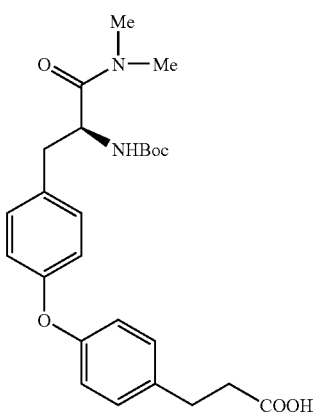

(6)

Amide 5 (8.4 g, 17.0 mmol) was dissolved in THF (60 mL) and diluted with water (60 mL). Lithium hydroxide (1.66 g, 69.0 mmol) was added and the reaction mixture was stirred at room temperature for about 2 h. The THF was evaporated and the resulting aqueous layer was acidified with 2.0 M HCl and extracted into EtOAc (2×100 mL). The organic layer was washed with water (1×100 mL) and brine (1×100 mL), dried and concentrated to yield the desired acid compound 6 (8.0 g, 97%). $^1$H NMR (400 MHz, DMSO-$d_6$): 12.15 (br, 1H), 7.22 (overlapped d, J=8.4 Hz, 4H), 7.06 (d, J=8.4 Hz, 1H), 6.88 (d, J=8.4 Hz, 2H), 6.86 (d, J=8.4 Hz, 2H), 4.53 (m, 1H), 2.91 (s, 3H), 2.73-2.83) (m, 9H), 1.31 (s, 9H).

Step VI

Preparation of (2-{4-[4-(2-benzyloxycarbamoyl-ethyl)-phenoxy]-phenyl}-1-dimethylcarbamoyl-ethyl)-carbamic acid tert-butyl ester (7)

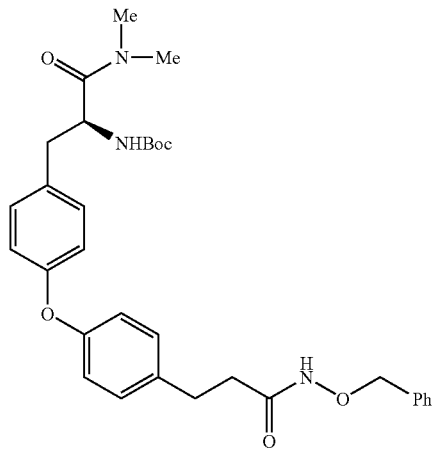

(7)

The acid compound 6 (4.8 g, 10.5 mmol) was dissolved in dry DMF and cooled to 0-5° C. 1-Hydroxybenzotriazole (1.56 g, 11.5 mmol), 1-(3-dimethylaminopropyl)-3-ethylcarbodiimide hydrochloride (EDCI, 2.0 g, 10.5 mmol), and triethylamine (4.4 mL, 31.6 mmol) were added to the above mixture followed by stirring for 15 min. O-Benzylhydroxylamine hydrochloride (1.85 g, 11.5 mmol) was added and the mixture was allowed to come to room temperature and stirred for 18 h. The solvent was evaporated under reduced pressure and the residual oil was taken up in EtOAc (100 mL). The organic layer was extracted with 2.0 M HCl (1×20 mL), saturated NaHCO$_3$ (1×20 mL), and brine (1×50 mL). The resulting EtOAc layer was dried and concentrated to yield the crude product. Flash chromatography (30-70% ethyl acetate in hexane containing 1% acetic acid) yielded the desired benzyl hydroxamate 7 (4.7 g, 78%). $^1$H NMR (400 MHz, DMSO-$d_6$): 10.96 (s, 1H), 7.32-7.38 (m, 5H), 7.23 (d, J=8.8 Hz, 2H), 7.17 (d, J=8.4 Hz, 7.06 (d, J=8.0 Hz, 1H), 6.86 (overlapped d, J=8.4 Hz, 4H), 4.72 (s, 2H), 4.53 (m, 1H), 2.90 (s, 3H), 2.69-2.86 (m, 7H), 2.25 (t, J=7.6 Hz, 2H), 1.30 (s, 9H).

Step VII

Preparation of (1-dimethylcarbamoyl-2-{4-[4-(2-hydroxycarbamoyl-ethyl)-phenoxy]-phenyl}-ethyl)-carbamic acid tert-butyl ester (8)

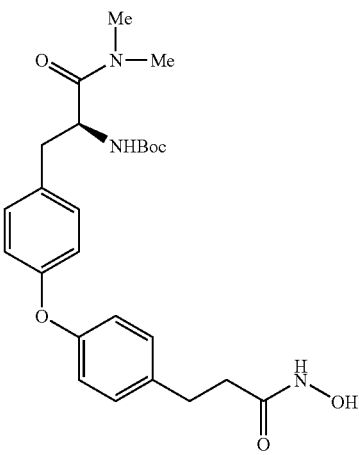

(8)

Palladium on BaSO$_4$ (5%, 4.0 g) was added to a degassed solution of the benzyl hydroxamate 7 (4.6 g) in MeOH (200 mL) and the suspension was treated with hydrogen at atmospheric pressure for 6 h. The suspension was filtered over a Celite® bed and concentrated to yield the desired hydroxamate 8 (3.5 g, 93%). $^1$H NMR (DMSO-$d_6$): 10.37 (s, 1H), 8.71 (s, 1H), 7.24 (d, J=8.4 Hz, 2H), 7.18 (d, J=8.4 Hz, 2H), 7.07 (d, J=8.4 Hz, 1H), 6.89 (d, J=8.4 Hz, 2H), 6.86 (d, J=8.8 Hz, 2H), 4.54 (ddd, J=14.8, 8.8, and 6.0 Hz, 1H), 2.91 (s, 3H), 2.70-2.87 (m, 7H), 2.24 (t, J=7.2 Hz, 2H), 1.32 (s, 9H).

Step VIII

Preparation of 2-amino-3-{4-[4-(2-hydroxycarbamoylethyl)-phenoxy]-phenyl}-N,N-dimethylpropionamide hydrochloride (9)

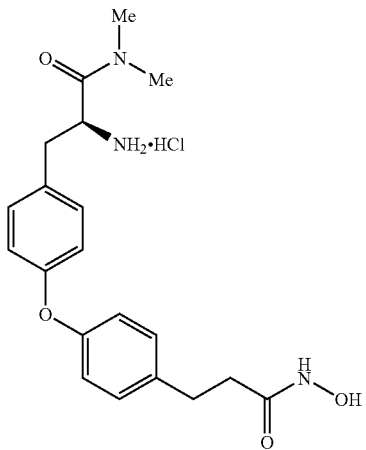

(9)

The hydroxamate 8 (3.4 g) was dissolved in CH$_2$Cl$_2$ and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×50 mL), decanted, and dried to yield the desired compound 9 as a white amorphous solid (2.9 g, 98%). $^1$H NMR (DMSO-d$_6$): 10.39 (s, 1H), 7.21 (d, J=8.4 Hz, 4H), 6.95 (d, J=8.4 Hz, 2H), 6.99 (d, J=8.4 Hz, 2H), 4.55 (m, 1H), 2.95-2.99 (m, 2H), 2.82 (s, 3H), 2.80 (t, J=8.0 Hz, 2H), 2.73 (s, 3H), 2.25 (t, J=8.0 Hz, 2H); LCMS (m/e): Obsd. 372.0, Calcd. 371.43

EXAMPLE 2

Synthesis of 3-{4-[4-(2-amino-2-dimethylcarbamoylethyl)-phenoxy]-phenyl}-propionic acid hydrochloride (10)

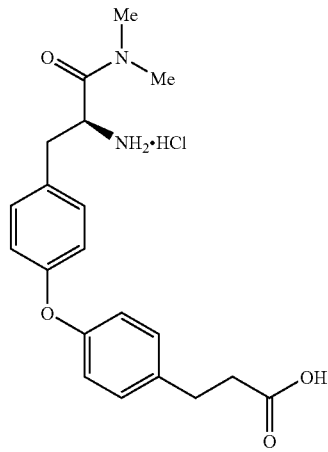

10

The acid compound 6 (0.8 g) was dissolved in CH$_2$Cl$_2$ (20 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×25 mL), decanted, and dried to yield the desired compound 10 as a white amorphous solid (0.6 g, 87%). $^1$H NMR (DMSO-d$_6$): 12.20 (br, 1H), 7.24 (d, J=8.4 Hz, 2H), 7.21 (d, J=8.8 Hz, 2H), 6.96 (d, J=8.8 Hz, 2H), 6.90 (d, J=8.0 Hz, 2H), 4.53 (m, 1H), 3.04 (dd, J=13.2 and 6.0 Hz, 1H), 2.95 (dd, J=14.0 and 8.0 Hz, 1H), 2.81 (m, 5H), 2.71 (s, 3H), 2.53 (t, J=7.6 Hz, 2H). LCMS (m/e): Obsd. 357.0, Calcd. 356.42

EXAMPLE 3

Synthesis of 2-amino-3-{4-[4-(2-carbamoylethyl)-phenoxy]-phenyl}-N,N-dimethyl-propionamide hydochloride (12)

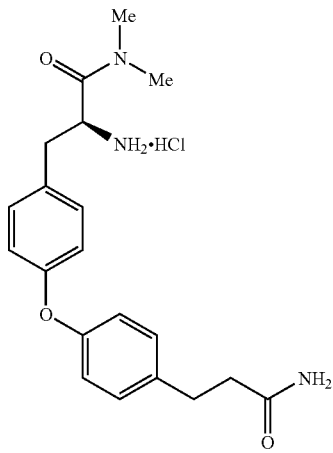

(12)

Step I

Preparation of (2-{4-[4-(2-carbamoylethyl)-phenoxy]-phenyl}-1-dimethylcarbamoylethyl)-carbamic acid tert-butyl ester (11)

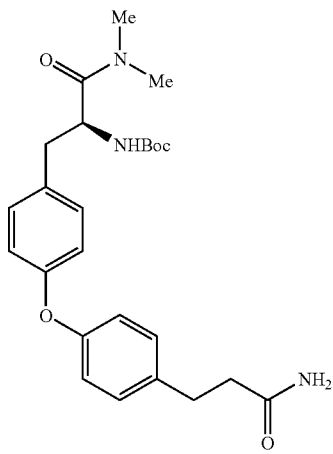

(11)

Acid compound 6 (1.5 g, 3.3 mmol) was dissolved in DCM (25 mL). Triethylamine (0.55 mL, 3.94 mmol) and BOP reagent (1.6 g, 3.61 mmol) were added and the reaction mixture stirred at room temperature for 15 min under an atmosphere of argon. Ammonia gas was then bubbled gently through the solution for 15-20 min to complete the reaction. Excess ammonia was degassed, the solvent was removed under reduced pressure and the residue was suspended in EtOAc (75 mL). The organic layer was washed with 0.5 N NaOH (2×10 mL), water (2×25 mL), and brine (1×30 mL), dried and concentrated under reduced pressure to yield the amide compound 11 (1.5 g, ~99%). $^1$H NMR (DMSO-d$_6$): 7.27 (br, 1H), 7.25 (d, J=8.4 Hz, 2H), 7.19 (d, J=8.4 Hz, 2H), 7.06 (d, J=8.4 Hz, 1H), 6.88 (d, J=8.8 Hz, 2H), 6.86 (d, J=8.4

Hz, 2H), 6.75 (br, 1H), 4.53 (m, 1H), 2.91 (s, 3H), 2.75-2.83 (m, 7H), 2.33 (t, J=7.6 Hz, 2H), 1.32 (s, 9H)

Step II

Preparation of 2-amino-3-{4-[4-(2-carbamoyl-ethyl)-phenoxy]-phenyl}-N,N-dimethyl-propionamide hydochloride (12)

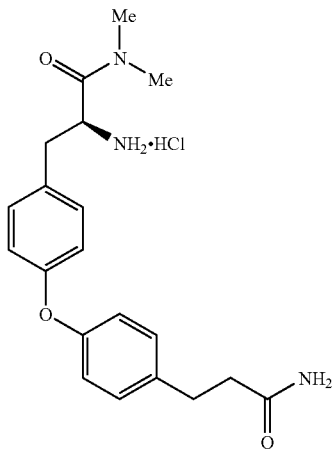

(12)

The amide compound 11 (1.5 g) was dissolved in CH$_2$Cl$_2$ (30 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×50 mL), decanted, and dried to yield the desired compound 12 as a white amorphous solid that was extremely hygroscopic (1.0 g, 77%). $^1$H NMR (DMSO-d$_6$): 7.29 (br, 1H), 7.20 (overlapped d, J=8.8 Hz, 2H), 7.19 (overlapped d, J=8.8 Hz, 2H), 6.88 (overlapped d, J=8.4 Hz, 2H), 6.87 (overlapped d, J=8.4 Hz, 2H), 6.87 (overlapped d, J=8.8 Hz, 2H), 6.76 (br, 1H), 4.63 (m, 1H), 2.83 (s, 3H), 2.54-2.78 (m, 7H), 2.34 (t, J=8.4 Hz, 2H).

EXAMPLE 4

Synthesis of 3-{4-[4-(2-amino-3-morpholin-4-yl-3-oxo-propyl)-phenoxy]-phenyl}-N-hydroxypropionamide hydrochloride (17)

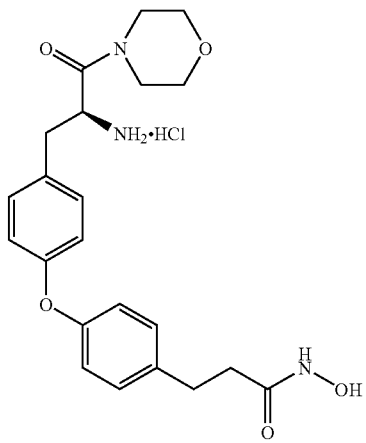

(17)

Step I

Preparation of 3-{4-[4-(2-tert-butoxycarbonylamino-3-morpholin-4-yl-3-oxo-propyl)-phenoxy]-phenyl}-propionic acid methyl ester (13)

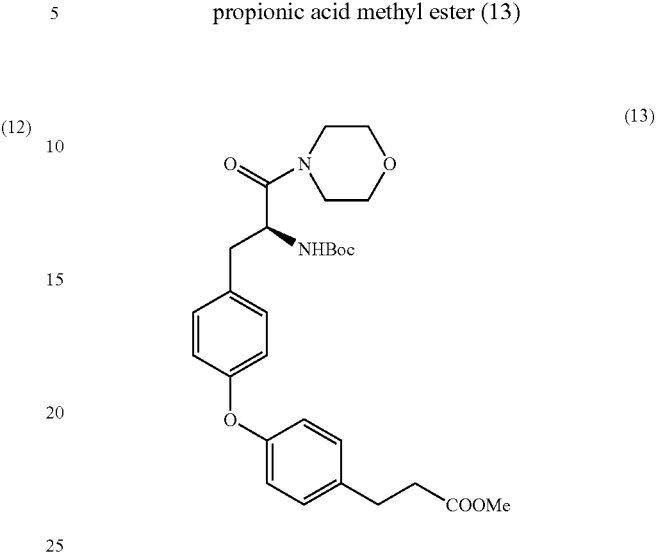

(13)

The compound 4 (2.0 g, 4.6 mmol) was dissolved in CH$_2$Cl$_2$ (25 mL) and stirred at room temperature under an atmosphere of argon. Triethylamine (0.94 mL, 6.76 mmol) and BOP reagent (2.19 g, 4.96 mmol) were added and the reaction mixture was stirred for 15 min. Morpholine (0.79 mL, 9.02 mmol) was added and the resulting solution was stirred at room temperature for about 1 h. The solvent was removed under reduced pressure and the resulting oil was taken up in EtOAc (60 mL). The organic layer was extracted with 1.0 N NaOH (1×10 mL), water (2×20 mL) and brine (1×20 mL). Drying and concentration of the organic layer gave the desired amide 13 (1.7 g, ~74%). $^1$H NMR (400 MHz, DMSO-d$_6$): 7.24 (d, J=8.8 Hz, 2H), 7.20 (d, J=8.4 Hz, 2H), 7.17 (d, J=8.4 Hz, 2H), 6.90 (d, J=8.4 Hz, 2H), 6.86 (d, J=8.4 Hz, 2H), 4.56 (m, 1H), 3.58 (s, 3H), 3.24-3.54 (m, 8H), 2.74-2.87 (m, 4H), 2.62 (t, J=6.0 Hz, 2H), 1.32 (s, 9H).

Step II

Preparation of 3-{4-[4-(2-tert-butoxycarbonylamino-3-morpholin-4-yl-3-oxopropyl)-phenoxy]-phenyl}-propionic acid (14)

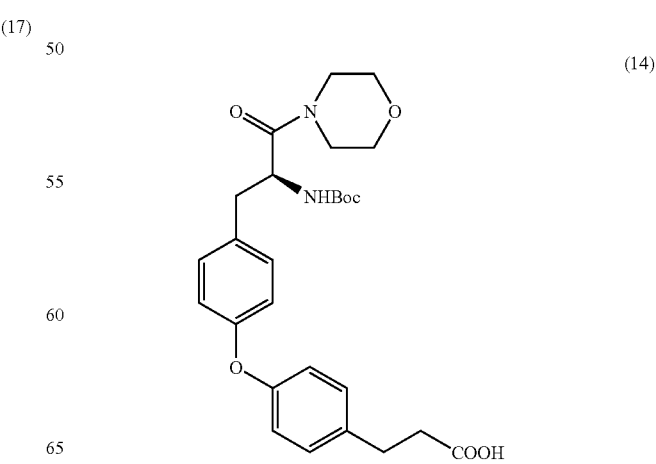

(14)

The amide 13 (2.2 g, 4.3 mmol) was dissolved in THF (25 mL) and diluted with water (25 mL). Lithium hydroxide (0.41 g, 17.0 mmol) was added and the reaction mixture was stirred at room temperature for about 2 h. The THF was evaporated and the resulting aqueous layer was acidified with 2.0 M HCl and extracted into EtOAc (2×50 mL). The organic layer was washed with water (1×50 mL) and brine (1×50 mL), dried and concentrated to yield the desired acid compound 14 (2.0 g, 93.5%). $^1$H NMR (400 MHz, DMSO-$d_6$): 12.1 (br, 1H), 7.20 (d, J=8.4 Hz, 2H), 7.17 (d, J=8.8 Hz, 2H), 7.14 (d, J=8.4 Hz, 1H), 6.86 (d, J=8.4 Hz, 2H), 6.82 (d, J=8.8 Hz, 2H), 4.52 (m, 1H), 3.22-3.47 (m, 8H), 2.72-2.80 (m, 4H), 1.28 (s, 9H).

Step III

Preparation of (1-{4-[4-(2-benzyloxycarbamoyl-ethyl)-phenoxy]-benzyl}-2-morpholin-4-yl-2-oxoethyl)-carbamic acid tert-butyl ester (15)

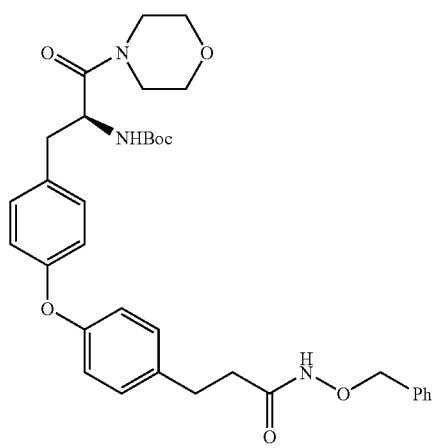

(15)

The acid 14 (2.0 g, 4.0 mmol) was dissolved in dry DMF (35 mL) and cooled to 0-5° C. 1-Hydroxybenzotriazole (0.6 g, 4.4 mmol), EDCI (0.77 g, 4.0 mmol), and triethylamine (1.68 mL, 12.0 mmol) were added to the above mixture followed by stirring for 15 min. O-Benzylhydroxylamine hydrochloride (0.7 g, 4.4 mmol) was added and the mixture was allowed to come to room temperature and stirred for 18 h. The solvent was evaporated under reduced pressure and the residual oil was taken up in EtOAc (100 mL). The organic layer was extracted with 2.0 M HCl (1×20 mL), saturated NaHCO$_3$ (1×20 mL), and brine (1×50 mL). The resulting EtOAc layer was dried and concentrated to yield the crude product. Flash chromatography on silica gel (hexanes:ethyl acetate—1:1 containing 1% acetic acid) yielded the desired benzyl hydroxamate 15 (1.6 g, 66%). $^1$H NMR (400 MHz, DMSO-$d_6$): 10.93 (s, 1H), 7.28-7.35 (m, 5H), 7.19 (d, J=8.4 Hz, 2H), 6.85 (d, J=8.4 Hz, 2H), 6.82 (d, J=8.4 Hz, 2H), 4.68 (s, 2H), 4.52 (m, 1H), 3.21-3.49 (m, 8H), 2.72-2.80 (m, 4H), 2.21 (t, J=7.6 Hz, 2H), 1.29 (s, 9H).

Step IV

Preparation of (1-{4-[4-(2-hydroxycarbamoyl-ethyl)-phenoxy]-benzyl}-2-morpholin-4-yl-2-oxoethyl)-carbamic acid tert-butyl ester (16)

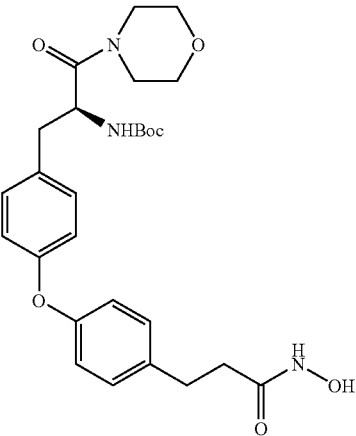

(16)

Palladium on BaSO$_4$ (5%, 0.5 g) was added to a degassed solution of the benzyl hydroxamate 15 (1.6 g) in MeOH (50 mL) and the suspension was treated with hydrogen at atmospheric pressure for 6 h. The suspension was filtered over a Celite® bed and concentrated to yield the desired hydroxamate 16 (1.1 g, 81%). $^1$H NMR (400 MHz, DMSO-$d_6$): 10.35 (s, 1H), 7.20 (d, J=8.4 Hz, 2H), 7.13-7.17 (m, 3H), 6.85 (d, J=8.4 Hz, 2H), 6.81 (d, J=8.8 Hz, 2H), 4.52 (m, 1H), 3.21-3.49 (m, 8H), 2.69-2.83 (m, 4H), 2.20 (t, J=8.0 Hz, 2H), 1.28 (s, 9H).

Step V

Preparation of 3-{4-[4-(2-amino-3-morpholin-4-yl-3-oxopropyl)-phenoxy]-phenyl}-N-hydroxypropionamide hydrochloride (17)

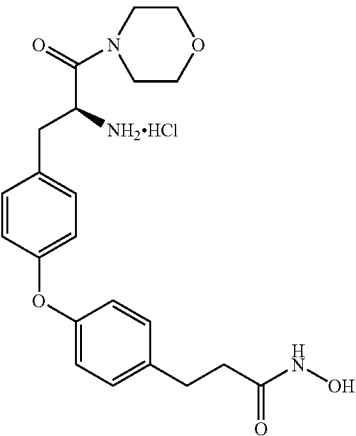

(17)

The compound 16 (1.1 g) was dissolved in CH$_2$Cl$_2$ (30 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×25 mL), decanted, and dried to yield the desired compound 17 as a white amorphous solid (0.82 g, 85%). $^1$H NMR (400 MHz, DMSO-$d_6$): 10.40 (s, 1H), 7.23 (overlapped d, J=8.8 Hz, 2H), 7.20 (overlapped d, J=8.8 Hz, 2H), 6.96 (d, J=8.4 Hz, 2H), 6.89 (d, J=8.4 Hz, 2H), 4.62 (m, 1H), 3.35-3.54 (m, 8H), 2.91-3.07 (m, 2H), 2.80 (t, J=8.0 Hz, 2H), 2.25 (t, J=8.0 Hz, 2H); LCMS: Obsd.414, Calcd. 413.47.

EXAMPLE 5

Synthesis of 3-(4-{4-[3-(4-acetylpiperazin-1-yl)-2-amino-3-oxopropyl]-phenoxy}-phenyl)-N-hydroxypropionamide hydrochloride (22)

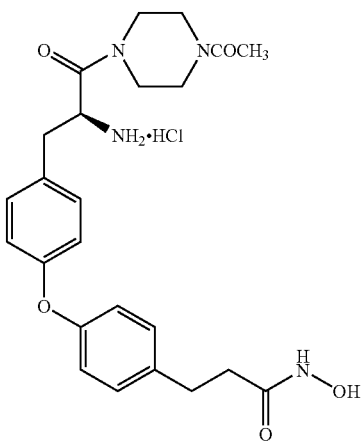

(22)

Step I

Preparation of 3-(4-{4-[3-(4-acetylpiperazin-1-yl)-2-tert-butoxycarbonylamino-3-oxo-propyl]-phenoxy}-phenyl)-propionic acid methyl ester (18)

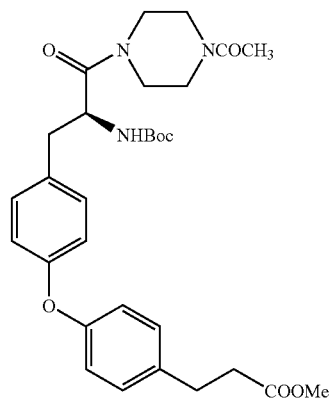

(18)

The hydrogenated compound 4 (2.0 g, 4.6 mmol) was dissolved in $CH_2Cl_2$ (20 mL) and stirred at room temperature under an atmosphere of argon. Triethylamine (0.75 mL, 5.4 mmol) and BOP reagent (2.19 g, 4.96 mmol) were added and the reaction mixture was stirred for 15 min. 1-Acetylpiperazine (1.16 g, 9.02 mmol) was added and the resulting solution was stirred at room temperature for about 2 h. The solvent was removed under reduced pressure and the resulting oil was taken up in EtOAc (75 mL). The organic layer was extracted with 1.0 N NaOH (1×10 mL), water (2×30 mL) and brine (1×30 mL). Drying and concentration of the organic layer gave the desired amide 18 (2.4 g, ~96%). $^1$H NMR (400 MHz, DMSO-$d_6$): 7.24 (d, J=8.8 Hz, 2H), 7.19 (d, J=8.8 Hz, 2H), 6.87 (d, J=7.6 Hz, 2H), 6.83 (d, J=8.4 Hz, 2H), 4.58 (m, 1H), 3.50 (s, 3H), 3.27-3.46 (m, 8H), 3.08-3.13 (m, 1H), 2.77-2.83 (m, 3H), 2.61 (t, J=7.2 Hz, 2H), 1.99 (s, 3H), 1.32 (s, 9H).

Step II

Preparation of 3-(4-{4-[3-(4-acetyl-piperazin-1-yl)-2-tert-butoxycarbonylamino-3-oxo-propyl]-phenoxy}-phenyl)-propionic acid (19)

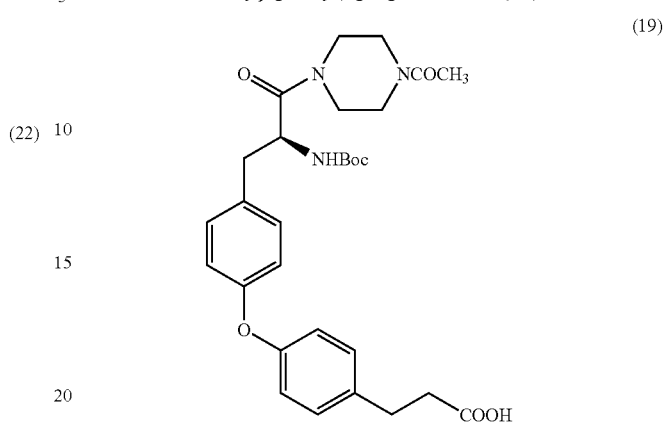

(19)

The amide compound 18 (2.3 g, 4.15 mmol) was dissolved in THF (20 mL) and diluted with water (20 mL). Lithium hydroxide (0.4 g, 17.0 mmol) was added and the reaction mixture was stirred at room temperature for about 2 h. The THF was evaporated and the resulting aqueous layer was acidified with 2.0 M HCl and extracted into EtOAc (2×30 mL). The organic layer was washed with water (1×40 mL) and brine (1×40 mL), dried and concentrated to yield the desired acid compound 19 (2.0 g, 89%). $^1$H NMR (400 MHz, DMSO-$d_6$): 7.16 (overlapped d, J=8.4 Hz, 2H), 7.15 (overlapped d, J=8.8 Hz, 2H), 6.91 (d, J=8.0 Hz, 2H), 6.86 (d, J=8.0 Hz, 2H), 5.47 (dd, J=12.8 and 8.4 Hz, 1H), 4.81 (m, 1H), 4.81 (m, 1H), 3.32-3.57 (m, 6H), 2.92-3.00 (m, 6H), 2.66 (t, J=6.8 Hz, 2H), 2.08 (d, J=7.6 Hz, 3H), 1.43 (s, 9H).

Step III

Preparation of (2-(4-acetyl-piperazin-1-yl)-1-{4-[4-(2-benzyloxycarbamoylethyl)-phenoxy]-benzyl}-2-oxo-ethyl)-carbamic acid tert-butyl ester (20)

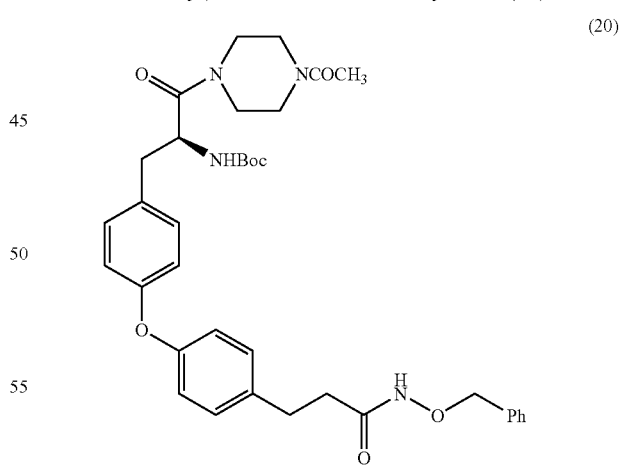

(20)

The compound 19 (1.95 g, 3.61 mmol) was dissolved in dry DMF (30 mL) and cooled to 0-5° C. 1-Hydroxybenzotriazole (0.54 g, 4.0 mmol), EDCI (0.7 g, 3.61 mmol), and triethylamine (1.5 mL, 11.0 mmol) were added to the above mixture followed by stirring for 15 min. O-Benzylhydroxylamine hydrochloride (0.64 g, 4.0 mmol) was added and the mixture was allowed to come to room temperature and stirred for 18 h. The solvent was evaporated under reduced pressure and the residual oil was taken up in EtOAc (60 mL). The organic layer was extracted with 2.0 M HCl (1×20 mL), saturated NaHCO₃ (1×20 mL), and brine (1×40 mL). The resulting EtOAc layer was dried and concentrated to yield the crude product. Silica gel flash chromatography (CHCl₃:MeOH—49:1) yielded the desired benzyl hydroxamate 15 (1.0 g, 44%). ¹H NMR (400 MHz, DMSO-d₆): 10.93 (s, 1H), 8.23 (s, 1H), 7.28-7.33 (m, 5H), 7.20 (d, J=8.4 Hz, 2H), 7.13 (d, J=8.4 Hz, 2H), 6.84 (d, J=7.2 Hz, 2H), 6.80 (d, J=8.4 Hz, 2H), 4.69 (s, 2H), 4.02 (m, 1H), 3.07-3.42 (m, 8H), 2.60-2.85 (m, 4H), 2.21 (t, J=7.6 Hz, 2H), 1.97 (s, 3H), 1.28 (s, 9H).

Step IV

Preparation of (2-(4-acetyl-piperazin-1-yl)-1-{4-[4-(2-hydroxycarbamoyl-ethyl)-phenoxy]-benzyl}-2-oxo-ethyl)-carbamic acid tert-butyl ester (21)

(21)

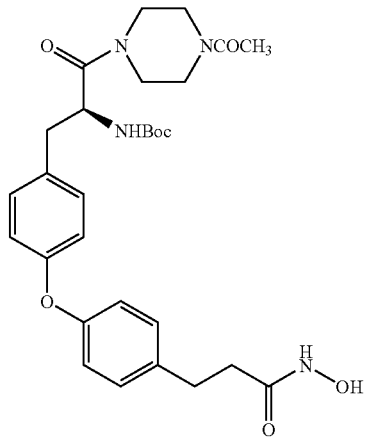

Palladium on BaSO₄ (5%, 0.4 g) was added to a degassed solution of the benzyl hydroxamate 20 (0.9 g) in MeOH (75 mL) and the suspension was treated with hydrogen at atmospheric pressure for 6 h. The suspension was filtered over a Celite® bed and concentrated to yield the desired hydroxamate 21 (~0.8 g, quantitative yield). ¹H NMR (400 MHz, DMSO-d₆): 10.38 (s, 1H), 8.72 (s, 1H), 7.24 (d, J=8.0 Hz, 2H), 7.16 (d, J=8.8 Hz, 2H), 6.88 (d, J=7.6 Hz, 2H), 6.83 (d, J=8.4 Hz, 2H), 4.58 (m, 1H) 3.10-3.45 (m, 8H), 2.76-2.85 (m, 4H), 2.24 (t, J=7.2 Hz, 2H), 2.00 (s, 3H), 1.32 (s, 9H).

Step V

Preparation of 3-(4-{4-[3-(4-acetylpiperazin-1-yl)-2-amino-3-oxo-propyl]-phenoxy}-phenyl)-N-hydroxypropionamide hydrochloride (22)

(22)

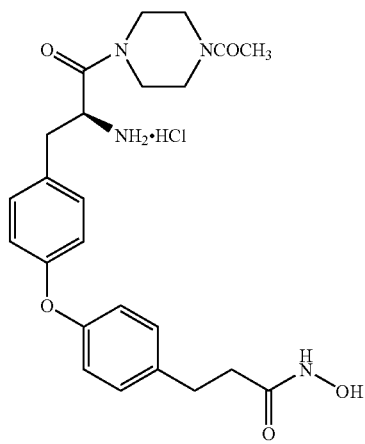

The acid compound 21 (0.8 g) was dissolved in CH₂Cl₂ (30 mL) and cooled to 0-5° C. Hydrogen chloride gas was bubbled through this solution for 20 min. The bubbling was discontinued and the reaction mixture was stirred at room temperature for 1 h. The excess HCl was degassed and the CH₂Cl₂ was removed. The residual solid was triturated with EtOAc (2×25 mL), decanted, and dried to yield the desired compound 22 as a white amorphous solid (0.82 g, 85%). ¹H NMR (CD₃OD): 7.26 (overlapped d, J=8.8 Hz, 1H), 7.25 (overlapped d, J=8.8 Hz, 1H), 7.20 (d, J=8.8 Hz, 2H), 6.97 (overlapped d, J=8.4 Hz, 1H), 6.95 (overlapped d, J=8.4 Hz, 1H), 6.89 (overlapped d, J=8.4 Hz, 1H), 6.88 (overlapped d, J=8.4 Hz, 1H), 4.65 (m, 1H), 3.3-3.6 (m, 6H), 3.0-2.8 (m, 4H), 2.91 (t, J=7.6 Hz, 2H), 2.39 (t, J=7.6 Hz, 2H), 2.10(d, J=11.2 Hz, 3H). LCMS: Obsd. 455.0, Calcd. 454.52

EXAMPLE 6

Synthesis of 3-(4-{4-[2-dimethylcarbamoyl-2-(toluene-4-sulfonylamino)-ethyl]-phenoxy}-phenyl)-propionic acid (25)

(25)

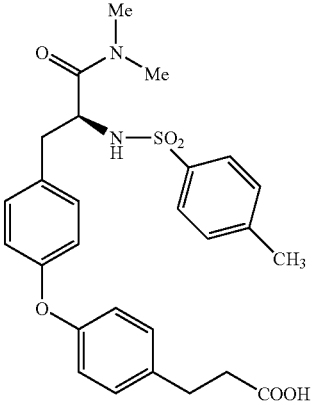

Step I

Preparation of 3-{4-[4-(2-amino-2-dimethylcarbamoyl-ethyl)-phenoxy]-phenyl}-propionic acid methyl ester hydrochloric acid salt (23)

(10)

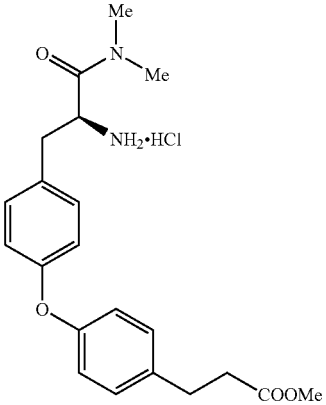

Amide compound 5 (1.8 g) was dissolved in CH₂Cl₂ (30 mL) and cooled to 0-5° C. Hydrogen chloride gas was bubbled through this solution for 20 min. The bubbling was discontinued and the reaction mixture was stirred at room temperature for 2 h. The excess HCl was degassed and the CH₂Cl₂ was removed. The residual sticky solid was dried under vacuum without further purification to yield the crude hydrochloride salt 23 (1.5 g, quantitative yield). ¹H NMR (400 MHz, DMSO-$d_6$): 7.20 (overlapped d, J=8.4 Hz, 2H), 7.18 (overlapped d, J=8.4 Hz, 2H), 6.90 (d, J=8.8 Hz, 2H), 6.86 (d, J=8.8 Hz, 2H), 4.50 (m, 1H), 3.55 (s, 3H), 2.98-3.04 (m, 3H), 2.91 (dd, J=14.0 and 8.0 Hz, 1H), 2.80 (t, J=7.2 Hz, 2H), 2.77 (s, 3H), 2.67 (s, 3H), 2.59 (t, J=7.2 Hz, 2H).

Step II

Preparation of 3-(4-{4-[2-dimethylcarbamoyl-2-(toluene-4-sulfonylamino)-ethyl]-phenoxy}-phenyl)-propionic acid methyl ester (24)

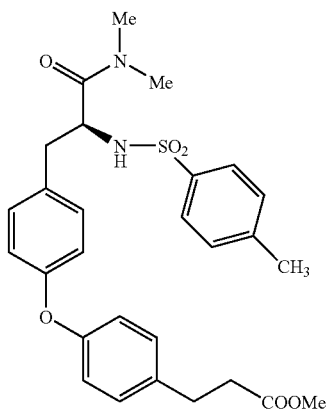

(24)

Hydrochloride compound 23 (1.5 g, 3.69 mmol) was dissolved in $CH_2Cl_2$ (50 mL) and cooled to 0-5° C. N,N'-Diisopropylethylamine (1.28 mL, 7.74 mmol) was added to the above solution followed by addition of p-toluenesulfonyl chloride (0.58 g, 3.06 mmol) in small portions. The reaction mixture was then warmed up to room temperature and stirred overnight. The solvent was removed under reduced pressure and the residual oil was taken up in EtOAc (75 mL). The organic layer was washed with 2.0 M HCl (1×10 mL), water (1×50 mL), and brine (2×50 mL). The resulting EtOAc layer was dried and concentrated under reduced pressure to yield oil. Flash chromatography (hexanes:ethyl acetate—3:2 containing 1% acetic acid) yielded the desired sulfonamide 24 (0.9 g, 47%). $^1$H NMR (400 MHz, DMSO-$d_6$): 7.54 (d, J=8.4 Hz, 2H), 7.29 (d, J=8.0 Hz, 2H), 7.22 (d, J=8.8 Hz, 2H), 7.10 (d, J=8.4 Hz, 2H), 6.86 (d, J=8.8 Hz, 2H), 6.82 (d, J=8.4 Hz, 2H), 4.39 (m, 1H), 3.58 (s, 3H), 2.72-2.92 (m, 4H), 2.69 (s, 3H), 2.57-2.64 (m, 4H), 2.47 (s, 3H), 2.35 (s, 3H).

Step III

Preparation of 3-(4-{4-[2-dimethylcarbamoyl-2-(toluene-4-sulfonylamino)-ethyl]-phenoxy}-phenyl)-propionic acid (25)

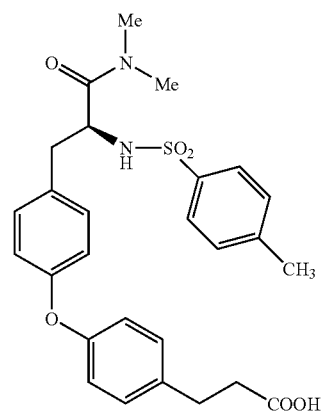

(25)

The sulfonamide compound 24 (0.9 g, 1.72 mmol) was dissolved in THF (10 mL) and diluted with water (10 mL). Lithium hydroxide (0.16, 6.86 mmol) was added and the reaction mixture was stirred at room temperature for about 2 h. The THF was evaporated and the resulting aqueous layer was acidified with 2.0 M HCl and extracted into EtOAc (2×25 mL). The organic layer was washed with water (1×25 mL) and brine (1×25 mL), dried and concentrated to yield the desired acid compound 25 (0.9 g, quantitative). $^1$H NMR (400 MHz, DMSO-$d_6$): 12.2 (br, 1H), 8.05 (d, J=9.2 Hz, 1H), 7.54 (d, J=8.4 Hz, 2H), 7.29 (d, J=7.6 Hz, 2H), 7.22 (d, J=8.8 Hz, 2H), 7.10 (d, J=8.8 Hz, 2H), 6.88 (d, J=8.4 Hz, 2H), 6.82 (d, J=8.8 Hz, 2H), 4.28 (m, 1H), 2.75-2.81 (m, 3H), 2.69 (s, 3H), 2.60 (dd, J=13.2 and 7.6 Hz, 1H), 2.52 (t, J=8.0 Hz, 2H), 2.35 (s, 3H). LCMS (m/e): Obsd. 526, Calcd. 525.62

EXAMPLE 7

Synthesis of 3-{4-[4-(2-hydroxycarbamoylethyl)-phenoxy]-phenyl}-N,N-dimethyl-2-(toluene-4-sulfonylamino)-propionamide (27)

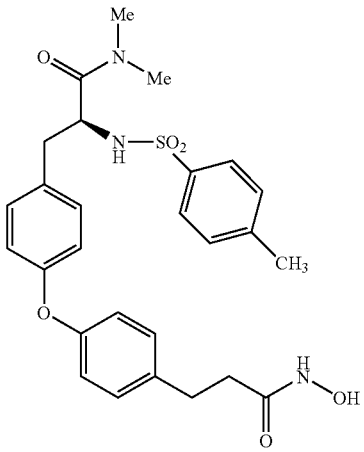

(27)

Step I

Preparation of 3-{4-[4-(2-benzyloxycarbamoylethyl)-phenoxy]-phenyl}-N,N-dimethyl-2-(toluene-4-sulfonylamino)-propionamide (26)

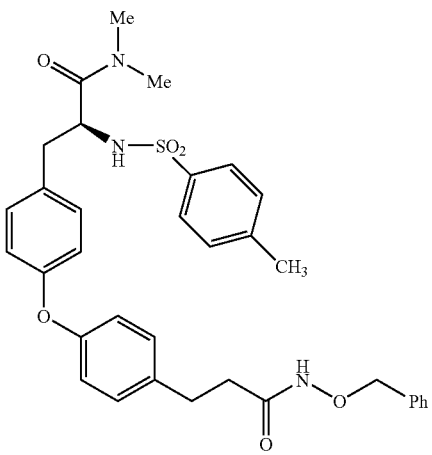

(26)

The acid compound 25 (0.85 g, 1.66 mmol) was dissolved in dry DMF (20 mL) and cooled to 0-5° C. 1-Hydroxybenzotriazole (0.25 g, 1.82 mmol), EDCI (0.32 g, 1.66 mmol), and triethylamine (0.7 mL, 5.0 mmol) were added to the above mixture followed by stirring for 15 min. O-Benzylhydroxylamine hydrochloride (0.3 g, 1.83 mmol) was added and the mixture was allowed to come to room temperature and stirred for 18 h. The solvent was evaporated under reduced pressure and the residual oil was taken up in EtOAc (50 mL). The organic layer was extracted with 2.0 M HCl (1×10 mL), saturated NaHCO$_3$ (1×10 mL), and brine (1×25 mL). The resulting EtOAc layer was dried and concentrated to yield the crude product. Flash chromatography on silica gel (hexanes: ethyl acetate—1:1 containing 1% acetic acid) yielded the desired benzyl hydroxamate 26 (0.8 g, 78%). $^1$H NMR (400 MHz, DMSO-d$_6$): 8.06 (d, J=9.6 Hz, 1H), 7.54 (d, J=8.4 Hz, 2H), 7.30-7.36 (m, 5H), 7.29 (d, J=8.0 Hz, 2H), 7.19 (d, J=8.0 Hz, 2H), 7.09 (d, J=8.8 Hz, 2H), 6.86 (d, J=8.8 Hz, 2H), 6.81 (d, J=8.8 Hz, 2H), 4.72 (s, 2H), 4.26-4.32 (m, 1H), 2.75-2.82 (m, 3H), 2.68 (s, 3H), 2.57-2.63 (dd, J=13.6 and 7.6 Hz, 1H), 2.35 (s, 3H), 2.25 (t, J=7.2 Hz, 2H).

Step II

Preparation of 3-{4-[4-(2-hydroxycarbamoyl-ethyl)-phenoxy]-phenyl}-N,N-dimethyl-2-(toluene-4-sulfonylamino)-propionamide (27)

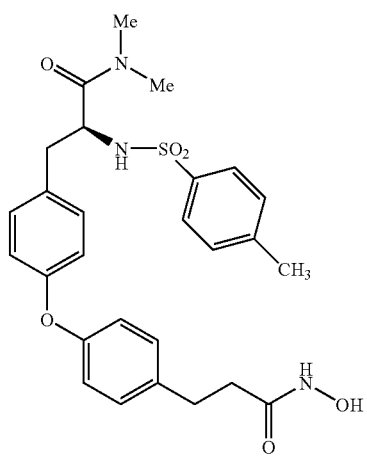

(27)

Palladium on BaSO$_4$ (5%, 0.5 g) was added to a degassed solution of the benzyl hydroxamate 26 (0.8 g) in MeOH (50 mL) and the suspension was treated with hydrogen at atmospheric pressure for 4 h. The suspension was filtered over a Celite® bed and concentrated to yield the desired hydroxamate 27 (0.4 g, 59%). $^1$H NMR (400 MHz, DMSO-d$_6$): 10.36 (s, 1H), 8.70 (br, 1H), 8.05 (d, J=9.2 Hz, 1H), 7.54 (d, J=8.4 Hz, 2H), 7.29 (d, J=7.6 Hz, 2H), 7.19 (d, J=8.8 Hz, 2H), 7.10 (d, J=8.4 Hz, 2H), 6.86 (d, J=8.8 Hz, 2H), 6.82 (d, J=8.8 Hz, 2H), 4.29 (m, 1H), 2.73-2.80 (m, 3H), 2.67 (s, 3H), 2.59 (dd, J=13.2 and 7.6 Hz, 1H), 2.99 (s, 3H), 2.24 (t, J=8.0 Hz, 2H). LCMS (m/e): Obsd. 511, Calcd. 510.6

EXAMPLE 8

Synthesis of D-2-amino-3-{4-[4-(2-hydroxycarbamoyl-ethyl)-phenoxy]-phenyl}-N,N-dimethyl-propionamide hydrochloride (28)

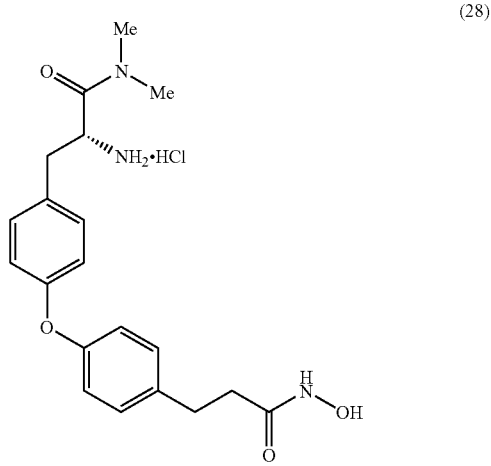

(28)

The title compound 28 was prepared by following similar method as that of compound 9 starting from Boc-D-tyrosine as a white amorphous solid. $^1$H NMR (DMSO-d$_6$): 10.43 (s, 1H), 7.21 (d, J=8.4 Hz, 4H), 6.94 (d, J=8.4 Hz, 2H), 6.89 (d, J=8.4 Hz, 2H), 4.53 (dd, J=12.4 and 6.8 Hz, 1H), 3.03 (dd, J=13.6 and 6.4 Hz, 1H), 2.94 (dd, J=13.6 and 7.6 Hz, 1H), 2.81 (s, 3H), 2.79 (overlapped t, J=8.0 Hz, 2H), 2.71 (s, 3H), 2.25 (t, J=8.0 Hz, 2H).

EXAMPLE 9

Synthesis of 3-{4-[4-(aminodimethylcarbamoylmethyl)-phenoxy]-phenyl}-N-hydroxy-propionamide hydrochloric acid salt (36)

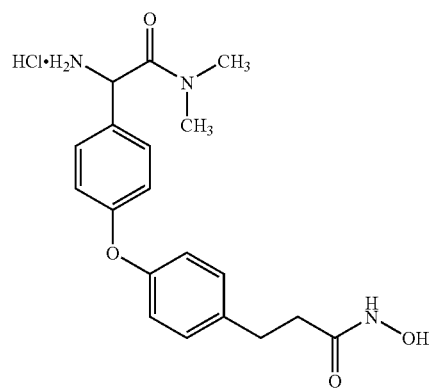

(36)

Step I

Preparation of tert-butoxycarbonylamino-[4-(4-formylphenoxy)-phenyl]-acetic acid (29)

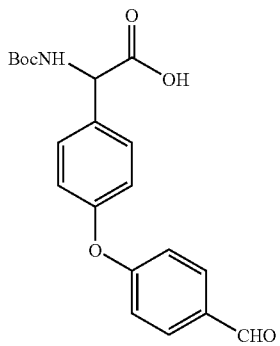

(29)

Potassium carbonate (23.11 g, 140 mmol) and 4-fluorobenzaldehyde (25.0 mL, 233 mmol) were added to a solution of tert-butoxycarbonylamino-(4-hydroxy-phenyl)-acetic acid (12.5 g, 46.7 mmol) in anhydrous DMF (40 mL). The resulting suspension was refluxed at 75±5° C. under an atmosphere of argon. After 72 hr, the reaction mixture was cooled to room temperature, diluted with water (200 mL) and extracted with EtOAc (2×150 mL). The aqueous layer was collected, acidified with 5.0 M HCl to pH ~2.0 and extracted with EtOAc (3×150 mL). The resulting EtOAc layer was extracted with water (2×300 mL) and brine (1×300 mL), dried over anhydrous magnesium sulfate, filtered and concentrated under reduced pressure to yield the desired aldehyde 29 as a low melting solid (12.0 g, 69%). $^1$H NMR (400 MHz, DMSO-$d_6$): 12.9 (br, 1H), 9.93 (s, 1H), 7.93 (d, J=8.8 Hz, 2H), 7.65 (d, J=8.8 Hz, 1H), 7.49 (d, J=8.8 Hz, 2H), 7.13 (overlapped d, J=8.8 Hz, 2H), 7.13 (overlapped d, J=8.8 Hz, 2H), 5.16 (d, J=8.0 Hz, 1H), 1.40 (s, 9H).

Step II

Preparation of 3-{4-[4-(tert-butoxycarbonylaminocarboxymethyl)-phenoxy]-phenyl}-acrylic acid methyl ester (30)

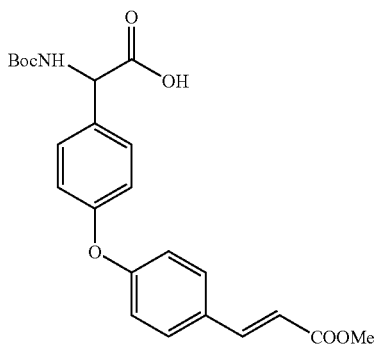

(30)

Sodium hydride (60% in mineral oil, 4.03 g, 100.0 mmol) was washed with anhydrous hexane (3×50 mL) under an atmosphere of argon. Dry THF (200 mL) was added and cooled to 0-5° C. A solution of trimethylphosphonoacetate (8.2 mL, 50.0 mmol) in dry THF (35 mL) was added dropwise to the above mixture with stirring. After about 5 min, a solution of the aldehyde 29 (17.0 g, 46.0 mmol) in dry THF (35 mL) was added and the reaction mixture was then brought up to room temperature and stirred. After 30 min, the clear reaction mixture was quenched with 10% citric acid (50 mL) and further acidified to pH ~2.0 with 2.0 M HCl. THF was evaporated under reduced pressure and the resulting oily material was extracted with EtOAc (2×400 mL). The organic layer was extracted with water (3×500 mL), and brine (1×500 mL), dried over anhydrous magnesium sulfate, filtered and concentrated in vacuo to yield the unsaturated ester 30 (20.0 g, quantitative yield) as a crude product that was taken for the next step without further purification. $^1$H NMR (400 MHz, DMSO-$d_6$): 12.9 (br, 1H), 7.75 (d, J=8.8 Hz, 2H), 7.65 (d, J=12.0 Hz, 1H), 7.60 (d, J=8.4 Hz, 1H), 7.05 (d, J=8.8 Hz, 2H), 7.01 (d, J=8.8 Hz, 2H), 6.56 (d, J=12.0 Hz, 1H), 5.12 (d, J=8.0 Hz, 1H), 3.72 (s, 3H), 1.40 (s, 9H).

Step III

Preparation of 3-{4-[4-(tert-butoxycarbonylaminocarboxymethyl)-phenoxy]-phenyl}-propionic acid methyl ester (31)

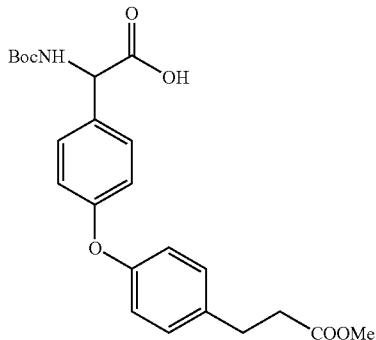

(31)

Raney nickel 2800 (21.9 g) was added to a degassed solution of the unsaturated ester 30 (20.0 g) in MeOH (100 mL) and the resulting suspension was treated with hydrogen at atmospheric pressure for 18 h. The suspension was filtered over a Celite® bed and concentrated. Completion of hydrogenation was determined by NMR. Flash chromatography (20-50% ethyl acetate in hexane containing 1% acetic acid) of the resulting residue gave the desired saturated ester 31 (15.1 g, 75%). $^1$H NMR (400 MHz, DMSO-$d_6$): 12.8 (br, 1H), 7.37 (d, J=8.8 Hz, 2H), 7.24 (d, J=8.4 Hz, 2H), 6.93 (d, J=8.4 Hz, 4H), 3.59 (s, 3H), 2.84 (t, J=7.6 Hz, 2H), 2.63 (t, J=7.6 Hz, 2H) 1.39 (s, 9H).

Step IV

Preparation of 3-{4-[4-(tert-butoxycarbonylaminodimethylcarbamoylmethyl)-phenoxy]-phenyl}-propionic acid methyl ester (32)

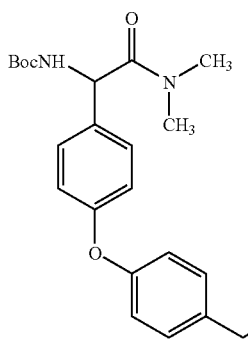

(32)

The hydrogenated compound 31 (4.0 g, 9.3 mmol) was dissolved in $CH_2Cl_2$ (60 mL) and stirred at room temperature under an atmosphere of argon. Triethylamine (1.56 mL, 11.0 mmol) and BOP reagent (4.53 g, 10.0 mmol) were added and the reaction mixture was stirred for 15 min. Dimethylamine (2.0 M solution in THF, 23.3 mL, 47.0 mmol) was added and the resulting solution was stirred at room temp for about 2-3 h. The solvent was removed under reduced pressure and the resulting oil was taken up in EtOAc (200 mL). The organic layer was extracted with 0.5 N NaOH (1×30 mL), water (2×100 mL) and brine (1×100 mL). Drying and concentration of the organic layer gave the desired amide 32 (3.7 g, 87%). $^1$H NMR (400 MHz, DMSO-$d_6$): 7.34 (d, J=8.4 Hz, 2H), 7.24 (d, J=8.4 Hz, 2H), 7.11 (d, J=8.0 Hz, 2H), 6.93 (overlapped d, J=8.8 Hz, 2H), 6.92 (overlapped d, J=8.0 Hz, 2H), 5.50 (d, J=8.0 Hz, 1H), 3.59 (s, 3H), 2.90 (s, 3H), 2.80-2.84 (m. 5H), 2.63 (t, J=7.6 Hz, 2H), 1.37 (s, 9H).

Step V

Preparation of 3-{4-[4-(tert-butoxycarbonylamin-odimethylcarbamoylmethyl)-phenoxy]-phenyl}-propionic acid (33)

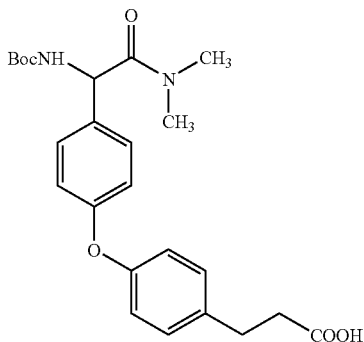

(33)

Amide 32 (3.6 g, 7.9 mmol) was dissolved in THF (40 mL) and diluted with water (40 mL). Lithium hydroxide (0.76 g, 31.0 mmol) was added and the reaction mixture was stirred at room temp for about 2 h. The THF was evaporated and the resulting aqueous layer was acidified with 2.0 M HCl and extracted into EtOAc (2×100 mL). The organic layer was washed with water (1×150 mL) and brine (1×200 mL), dried and concentrated to yield the desired acid compound 33 (3.4 g, 97%). $^1$H NMR (400 MHz, DMSO-$d_6$): 12.2 (br, 1H), 7.34 (d, J=8.4 Hz, 2H), 7.25 (d, J=8.4 Hz, 2H), 7.12 (d, J=8.0 Hz, 1H), 6.93 (d, J=8.4 Hz, 2H), 6.93 (d, J=8.8 Hz, 2H), 5.50 (d, J=8.0 Hz, 1H), 2.90 (s, 3H), 2.84 (s, 3H), 2.81 (t, J=7.6 Hz, 2H), 2.53 (t, J=7.6 Hz, 2H), 1.37 (s, 9H).

Step VI

Preparation of ({4-[4-(2-benzoyloxycarbamoyl-ethyl)-phenoxy]-phenyl}-dimethylcarbamoylm-ethyl)-carbamic acid tert-butyl ester (34)

(34)

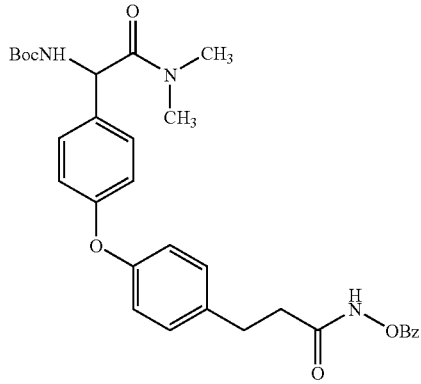

The acid compound 33 (1.5 g, 3.4 mmol) was dissolved in dry DMF (20 mL) and cooled to 0-5° C. 1-Hydroxybenzotriazole (0.5 g, 3.73 mmol), 1-(3-dimethylaminopropyl)-3-ethylcarbodiimide hydrochloride (0.65 g, 3.4 mmol), and triethylamine (1.42 mL, 10.0 mmol) were added to the above mixture followed by stirring for 15 min. O-Benzylhydroxylamine hydrochloride (0.6 g, 3.73 mmol) was added and the mixture was allowed to come to room temperature and stirred for 18 h. The solvent was evaporated under reduced pressure and the residual oil was taken up in EtOAc (100 mL). The organic layer was extracted with 2.0 M HCl (1×10 mL), saturated NaHCO$_3$ (1×10 mL), and brine (1×50 mL). The resulting EtOAc layer was dried and concentrated to yield the crude product. Flash chromatography (30-70% ethyl acetate in hexane containing 1% acetic acid) yielded the desired benzyl hydroxamate 34 (1.6 g, 84%). $^1$H NMR (400 MHz, DMSO-$d_6$): 10.97 (s, 1H), 7.32-7.36 (m, 7H), 7.21 (d, J=8.4 Hz, 2H), 7.11 (d, J=8.0 Hz, 1H), 6.93 (overlapped d, J=8.4 Hz, 2H), 6.91 (overlapped d, J=8.4 Hz, 2H), 5.50 (d, J=8.0 Hz, 2H), 4.73 (s, 2H), 2.89 (s, 3H), 2.80-2.83 (m, 5H), 2.26 (t, J=7.6 Hz, 2H), 1.39 (s, 9H).

Step VII

Preparation of (dimethylcarbamoyl-{4-[4-(2-hy-droxycarbamoyl-ethyl)-phenoxy]-phenyl}-methyl)-carbamic acid tert-butyl ester (35)

(35)

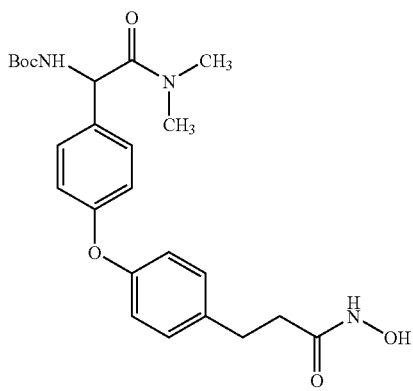

Palladium (5% on BaSO$_4$, 2.0 g) was added to a degassed solution of the benzyl hydroxamate 34 (1.5 g) in MeOH (100 mL) and the suspension was treated with hydrogen at atmospheric pressure for 6 h. The suspension was filtered over a Celite® bed and concentrated to yield the desired hydroxamate 35 (1.1 g, 90%). $^1$H NMR (400 MHz, DMSO-$d_6$): 10.42 (s, 1H), 7.33 (d, J=8.4 Hz, 2H), 7.22 (d, J=8.4 Hz, 2H), 7.12 (d, J=8.4 Hz, 1H), 6.93 (overlapped d, J=8.8 Hz, 2H), 6.92 (overlapped d, J=8.4 Hz, 2H), 5.50 (d, J=8.0 Hz, 1H), 2.90 (s, 3H), 2.84 (s, 3H), 2.80 (t, J=8.0 Hz, 2H), 2.25 (t, J=7.6 Hz, 2H), 1.37 (s, 9H).

Step VIII

Preparation of 3-{4-[4-(aminodimethylcarbamoylmethyl)-phenoxy]-phenyl}-N-hydroxypropionamide hydrochloric acid salt (36)

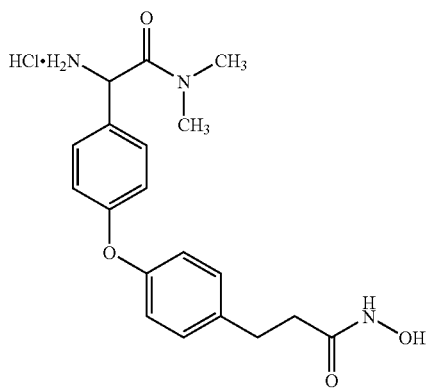
(36)

The hydroxamate 35 (1.1 g) was dissolved in CH$_2$Cl$_2$ and cooled to 0-5° C. Hydrogen chloride gas was bubbled through this solution for 20 min. The bubbling was discontinued and the reaction mixture was stirred at room temp for 1 h. The excess HCl was degassed and the CH$_2$Cl$_2$ was removed. The residual solid was triturated with EtOAc (2×50 mL), decanted, and dried to yield the desired compound 36 as a white amorphous solid (0.87 g, 92%). $^1$H NMR (DMSO-d$_6$): 10.44 (s, 1H), 7.46 (d, J=8.8 Hz, 2H), 7.24 (d, J=8.8 Hz, 2H), 7.03 (d, J=8.4 Hz, 2H), 6.95 (d, J=8.4 Hz, 2H), 5.48 (d, J=5.2 Hz, 1H), 2.89 (s, 3H), 2.82 (s, 3H), 2.81 (t, J=8.0 Hz, 2H), 2.26 (t, J=8.0 Hz, 2H). LCMS (m/e): Obsd. [M+Na]$^+$ 380, Calcd. 357.4

EXAMPLE 10

Synthesis of 3-{4-[4-(aminodimethylcarbamoylmethyl)-phenoxy]-phenyl}-propionic acid (37)

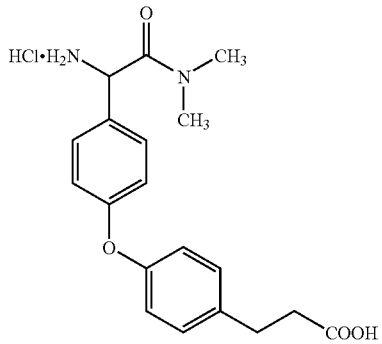
(37)

The acid compound 33 (0.3 g) was dissolved in CH$_2$Cl$_2$ (20 mL) and cooled to 0-5° C. Hydrogen chloride gas was bubbled through this solution for 20 min. The bubbling was discontinued and the reaction mixture was stirred at room temp for 1 h. The excess HCl was degassed and the CH$_2$Cl$_2$ was removed. The residual solid was triturated with EtOAc (2×25 mL), decanted, and dried to yield the desired compound 37 as a white amorphous solid (0.15 g, 59%). $^1$H NMR (400 MHz, DMSO-d$_6$): 12.2 (br, 1H), 7.47 (d, J=9.2 Hz, 2H), 7.29 (d, J=8.4 Hz, 2H), 7.04 (d, J=8.8 Hz, 2H), 6.96 (d, J=8.4 Hz, 2H), 5.49 (s, 1H), 2.90 (s, 3H), 2.81-2.84 (m, 5H), 2.54 (t, J=8.0 Hz, 2H).

EXAMPLE 11

Synthesis of 3-{4-[4-(aminodimethylcarbamoylmethyl)-phenoxy]-phenyl}-propionamide hydrochloric acid salt (39)

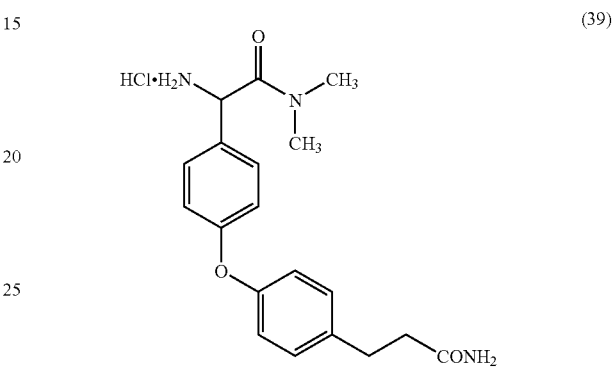
(39)

Step I

Preparation of ({4-[4-(2-carbamoylethyl)phenoxy]-phenyl}-dimethylcarbamoylmethyl)-carbamic acid tert-butyl ester (38)

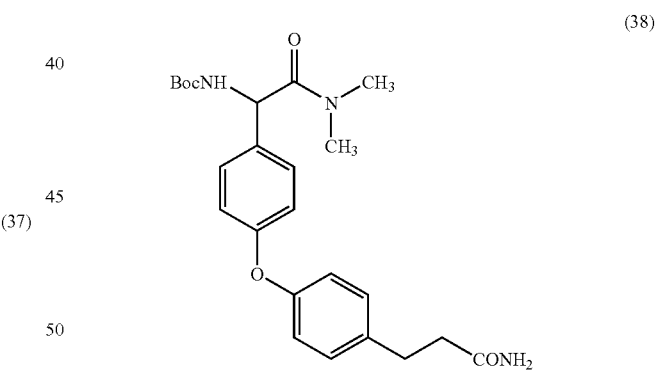
(38)

Acid compound 33 (0.7 g, 1.58 mmol) was dissolved in DCM (25 mL). Triethylamine (0.26 mL, 1.89 mmol) and BOP reagent (0.77 g, 1.74 mmol) were added and the reaction mixture stirred at room temp for 15 min under an atmosphere of argon. Ammonia gas was then bubbled gently through the solution for 15-20 min to complete the reaction. Excess ammonia was degassed, the solvent was removed under reduced pressure and the residue was suspended in EtOAc (75 mL). The organic layer was washed with 0.5 N NaOH (2×10 mL), water (2×25 mL), and brine (1×30 mL), dried and concentrated under reduced pressure to yield the amide compound 38 (0.7 g, quantitative yield). $^1$H NMR (400 MHz, DMSO-d$_6$): 7.33 (d, J=8.4 Hz, 2H), 7.30 (br, 1H), 7.23 (d, J=8.4 Hz, 2H), 7.12 (d, J=8.0 Hz, 1H), 6.93 (overlapped d, J=8.8 Hz, 2H0, 6.92 (overlapped d, J=8.8 Hz, 2H), 6.78 (br, 1H), 5.50 (d, J=8.0 Hz, 1H), 2.90 (s, 3H), 2.84 (s, 3H), 2.79 (t, J=8.0 Hz, 2H), 2.35 (t, J=8.0 Hz, 2H), 1.37 (s, 9H).

Step II

Preparation of 3-{4-[4-(aminodimethylcarbamoylmethyl)-phenoxy]-phenyl}-propionamide hydrochloric acid salt (39)

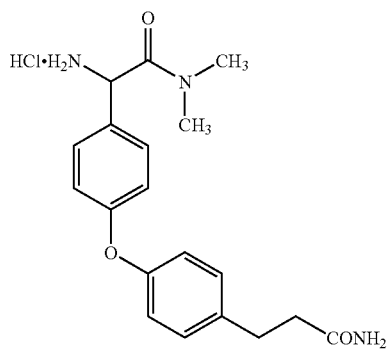

The amide compound 38 (0.6 g) was dissolved in $CH_2Cl_2$ (30 mL) and cooled to 0-5° C. Hydrogen chloride gas was bubbled through this solution for 20 min. The bubbling was discontinued and the reaction mixture was stirred at room temp for 1 h. The excess HCl was degassed and the $CH_2Cl_2$ was removed. The residual solid was triturated with EtOAc (2×50 mL), decanted, and dried to yield the desired compound 39 as a white amorphous solid that was extremely hygroscopic (0.44 g, 86%). $^1$H NMR (400 MHz, DMSO-$d_6$): 7.47 (d, J=8.8 Hz, 2H), 7.34 (br, 1H), 7.26 (d, J=8.4 Hz, 2H), 7.03 (d, J=8.3 Hz, 2H), 6.95 (d, J=8.4 Hz, 2H), 6.78 (br, 1H), 5.51 (d, J=5.6 Hz, 1H), 2.89 (s, 3H), 2.83 (s, 3H), 2.80 (2.80 (t, J=8.0 Hz,2H), 2.36 (t, J=8.0 Hz, 2H).

EXAMPLE 12

Synthesis of 3-{4-[4-aminodimethylcarbamoylmethyl)-phenoxy]-phenyl}-N,N-dimethylpropionamide hydrochloric acid salt (41)

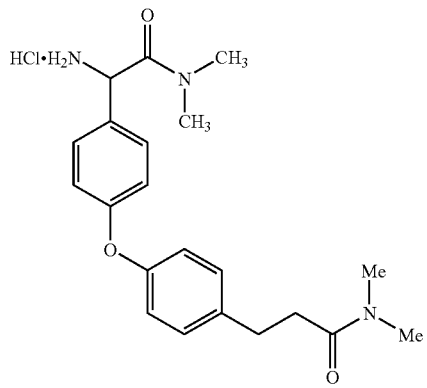

Step I

Preparation of (dimethylcarbamoyl-{4-[4-(2-dimethylcarbamoylethyl)-phenoxy]-phenyl}-methyl)-carbamic acid tert-butyl ester (40)

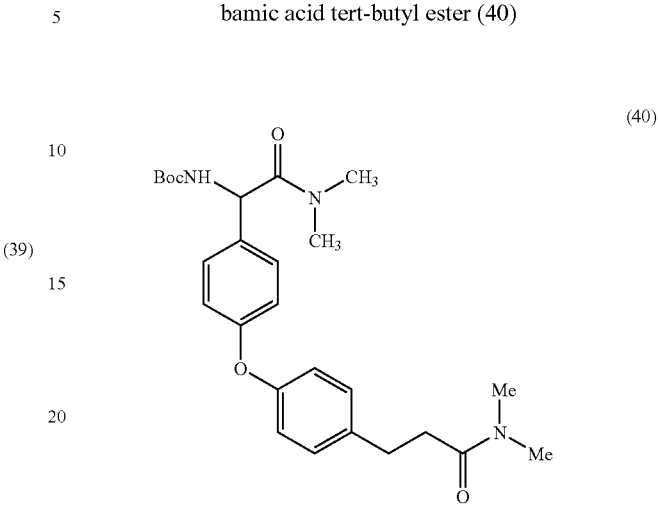

Acid compound 33 (0.7 g, 1.58 mmol) was dissolved in DCM (20 mL) and stirred at room temp under an atmosphere of argon. Triethylamine (0.26 mL, 1.9 mmol) and BOP reagent (0.77 g, 1.74 mmol) were added and the reaction mixture was stirred for 15 min. Dimethylamine (2.0 M solution in THF, 4.0 mL, 7.9 mmol) was added and the resulting solution was stirred at room temp for about 2-3 h. The solvent was removed under reduced pressure and the resulting oil was taken up in EtOAc (200 mL). The organic layer was extracted with 0.5 N NaOH (1×30 mL), water (2×100 mL) and brine (1×100 mL). Drying and concentration of the organic layer gave the desired amide 40 (0.7 g, 94.5%). $^1$H NMR (400 MHz, DMSO-$d_6$): 7.33 (d, J=8.4 Hz, 2H), 7.26 (d, J=8.4 Hz, 2H), 7.11 (d, J=8.0 Hz, 1H), 6.93 (overlapped d, J=8.4 Hz, 2H), 6.92 (overlapped d, J=8.4 Hz, 2H), 5.50 (d, J=7.6 Hz, 2H), 2.93 (s, 3H), 2.90 (s, 3H), 2.84 (s, 3H), 2.82 (s, 3H), 2.79 (t, J=8.0 Hz, 2H), 2.59 (t, J=8.0 Hz, 2H), 1.37 (s, 9H).

Step II

Preparation of 3-{4-[4-(aminodimethylcarbamoylmethyl)-phenoxy]-phenyl}-N,N-dimethylpropionamide hydrochloric acid salt (41)

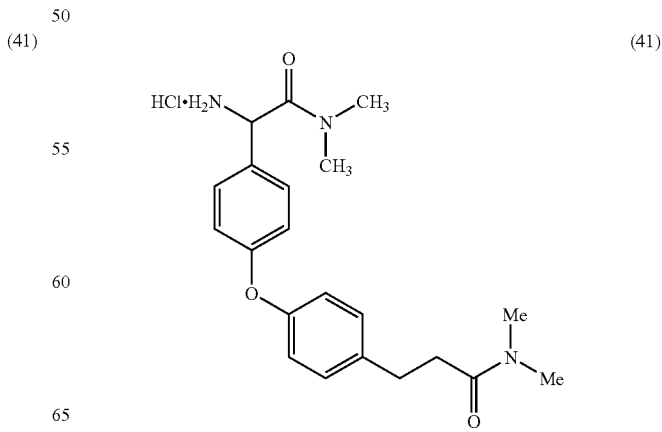

The amide compound 40 (0.6 g) was dissolved in $CH_2Cl_2$ (30 mL) and cooled to 0-5° C. Hydrogen chloride gas was bubbled through this solution for 20 min. The bubbling was discontinued and the reaction mixture was stirred at room temp for 1 h. The excess HCl was degassed and the $CH_2Cl_2$ was removed. The residual solid was triturated with EtOAc (2×50 mL), decanted, and dried to yield the desired compound 41 as a white amorphous solid that was extremely hygroscopic (0.43 g, 83%). $^1$H NMR (400 MHz, DMSO-$d_6$): 7.46 (d, J=8.8 Hz, 2H), 7.29 (d, J=8.8 Hz, 2H), 7.03 (d, J=8.4 Hz, 2H), 6.95 (d, J=8.4 Hz, 2H), 5.48 (d, J=5.2 Hz, 1H), 2.93 (s, 3H), 2.89 (s, 3H), 2.82 (s, 3H), 2.81 (s, 3H), 2.80 (t, J=8.0 Hz, 2H), 2.59 (t, J=8.0 Hz, 2H). LCMS (m/e): Obsd. 469, Calcd. 369.46.

EXAMPLE 13

Synthesis of 2-amino-3-[4'-(2-hydroxycarbamoyl-ethyl)-biphenyl-4-yl]-N,N-dimethylpropionamide hydrochloric acid salt (49)

Step I

Preparation of 2-tert-butoxycarbonylamino-3-(4'-formylbiphenyl-4-yl)-propionic acid, (42)

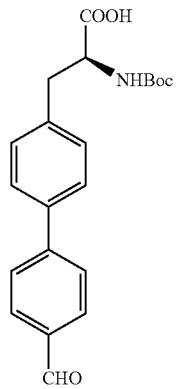

(42)

The amino acid (5.0 g, 15.0 mmol) and 4-formylphenyl-boronic acid (2.18 g, were dissolved in toluene (120 mL). An aqueous solution of $K_2CO_3$ (2.0 M, 21.8 mL) and ethanol (12 mL) were added to it, followed by the palladium catalyst and the resulting solution was heated at 85° C. for 18 h under an atmosphere of argon. The reaction mixture was diluted with water (50 mL) and the organic layer was separated. The aqueous layer was acidified with 2.0 M HCl and extracted with EtOAc (2×100 mL). The EtOAc layer was sequentially washed with water (2×75 mL) and brine (2×50 mL), dried over anhydrous magnesium sulfate, filtered and concentrated under reduced pressure to yield the crude product. Flash chromatography (20-40% ethyl acetate in hexane containing 1% acetic acid) yielded the desired aldehyde compound 42 (4.0 g, 74.6%). $^1$H NMR (400 MHz, DMSO-$d_6$): 12.23 (br, 1H), 10.05 (s, 1H), 7.98 (d, J=8.8 Hz, 2H), 7.90 (d, J=8.0 Hz, 2H), 7.70 (d, J=8.8 Hz, 2H), 7.40 (d, J=8.0 Hz, 2H), 7.17 (d, J=8.8 Hz, 1H), 4.14 (ddd, J=12.8, 10.4, and 4.4 Hz, 1H), 3.09 (dd, J=13.6 and 4.4 Hz, 1H), 2.89 (dd, J=13.6 and 10.4 Hz, 1H), 1.32 (d, 9H).

Step II

Preparation of 3-[4'-(2-tert-butoxycarbonylamino-2-carboxyethyl)-biphenyl-4-yl]-acrylic acid methyl ester (43)

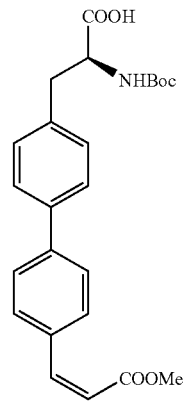

(43)

Sodium hydride (60% in mineral oil, 1.02 g, 26.0 mmol) was washed with anhydrous hexane (3×15 mL) under an atmosphere of argon. Dry THF (20 mL) was added and cooled to 0-5° C. A solution of trimethylphosphonoacetate (2.1 mL, 13.0 mmol) in dry THF (20 mL) was added dropwise to the above mixture with stirring. After about 5 min, a solution of the aldehyde 42 (4.3 g, 10.6 mmol) in dry THF (20 mL) was added and the reaction mixture was then brought up to room temperature and stirred. After 30 min, the clear reaction mixture was quenched with 10% citric acid (25 mL) and further acidified to pH ~2.0 with 2.0 M HCl. The THF was evaporated under reduced pressure and the resulting oily material was extracted with EtOAc (2×100 mL). The organic layer was extracted with water (3×75 mL), and brine (1×100 mL), dried over anhydrous magnesium sulfate, filtered and concentrated in vacuo to yield the unsaturated ester 43 (4.6 g, 93%) as a crude product that was taken for the next step without further purification. $^1$H NMR (400 MHz, DMSO-$d_6$): 12.66 (br, 1H), 7.80 (d, J=8.4 Hz, 2H), 7.72 (overlapped d, J=8.8 Hz, 2H), 7.70 (overlapped d, J=16.0 Hz, 1H), 7.36 (d, J=8.0 Hz, 2H), 7.18 (d, J=8.4 Hz, 1H), 6.69 (d, J=16.0 Hz, 1H), 4.13 (ddd, J=12.8, 10.4, and 4.8 Hz, 1H), 3.74 (s, 3H), 3.07 (dd, J=14.0 and 4.8 Hz, 1H), 2.88 (dd, J=13.6 and 10.0 Hz, 1H), 1.32 (s, 9H)

Step III

Preparation of 2-tert-butoxycarbonylamino-3-[4'-(2-methoxycarbonylethyl)-biphenyl-4-yl]-propionic acid (44)

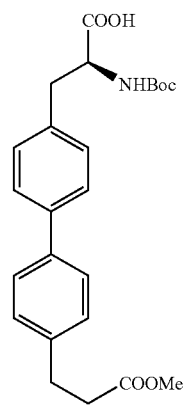

(44)

Raney nickel 2800 (4.0 g) was added to a degassed solution of the unsaturated ester 43 (4.1 g) in MeOH (150 mL) and the resulting suspension was treated with hydrogen at atmospheric pressure for 18 h. The suspension was filtered over a Celite® bed and concentrated. Flash chromatography (30-50% ethyl acetate in hexane containing 1% acetic acid) of the resulting residue gave the desired saturated ester 44 (3.8 g, 94.5%). $^1$H NMR (400 MHz, DMSO-d$_6$): 7.54 (d, J=7.6 Hz, 4H), 7.31 (overlapped d, J=8.8 Hz, 2H), 7.29 (overlapped d, J=8.4 Hz, 2H), 4.12 (m, 1H), 3.58 (s, 3H), 2.87 (t, J=7.6 Hz, 2H), 2.65 (t, J 7.6 Hz, 2H), 1.31 (s, 9H).

Step IV

Preparation of 3-[4'-(2-tert-butoxycarbonylamino-2-dimethylcarbamoylethyl)-biphenyl-4-yl]-propionic acid methyl ester (45)

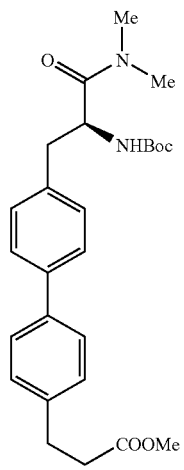

(45)

The hydrogenated compound 44 (4.3 g, 10.0 mmol) was dissolved in CH$_2$Cl$_2$ (50 mL) and stirred at room temperature under an atmosphere of argon. Triethylamine (1.68 mL, 12.0 mmol) and BOP reagent (4.9 g, 11.0 mmol) were added and the reaction mixture was stirred for 15 min. Dimethylamine (2.0 M solution in THF, 25.0 mL, 50.0 mmol) was added and the resulting solution was stirred at room temperature for about 2-3 h. The solvent was removed under reduced pressure and the resulting oil was taken up in EtOAc (100 mL). The organic layer was extracted with 0.5 N NaOH (1×10 mL), water (2×50 mL) and brine (1×50 mL). Drying and concentration of the organic layer gave the desired amide 45 (4.4 g, 96%). $^1$H NMR (400 MHz, DMSO-d$_6$): 7.56 (overlapped d, J=8.4 Hz, 2H), 7.55 (overlapped d, J=8.4 Hz, 2H), 7.32 (d, J=8.8 Hz, 2H), 7.30 (d, J=8.8 Hz, 2H), 7.13 (d, J=8.4 Hz, 1H), 4.58 (m, 1H), 3.60 (s, 3H), 2.94 (s, 3H), 2.89 (t, J=7.6 Hz, 2H), 2.79-2.83 (m, 5H), 2.67 (t, J=7.6 Hz, 2H), 1.31 (s, 9H).

Step V

Preparation of 3-[4'-(2-tert-butoxycarbonylamino-2-dimethylcarbamoylethyl)-biphenyl-4-yl]-propionic acid (46)

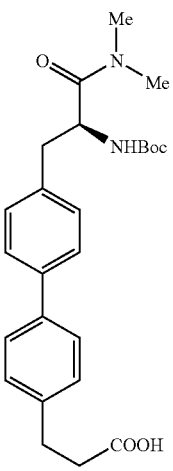

(46)

Amide 45 (4.3 g, 9.46 mmol) was dissolved in THF (35 mL) and diluted with water (35 mL). Lithium hydroxide (0.91 g, 38.0 mmol) was added and the reaction mixture was stirred at room temperature for about 2 h. The THF was evaporated and the resulting aqueous layer was acidified with 2.0 M HCl and extracted into EtOAc (2×100 mL). The organic layer was washed with water (1×100 mL) and brine (1×100 mL), dried and concentrated to yield the desired acid compound 46 (3.9, 93.7%). $^1$H NMR (400 MHz, DMSO-d$_6$): 12.22 (br, 1H), 7.55 (d, J=8.4 Hz, 4H), 7.32 (overlapped d, J=8.0 Hz, 2H), 7.31 (overlapped d, J=8.0 Hz, 2H), 7.14 (d, J=8.4 Hz, 1H), 4.56 (m, 1H), 2.94 (s, 3H), 2.75-2.90 (m, 7H), 2.57 (t, J=7.6 Hz, 2H), 1.31 (s, 9H).

Step VI

Preparation of {1-dimethylcarbamoyl-2-[4'-(2-phenoxycarbamoylethyl)-biphenyl-4-yl]-ethyl}-carbamic acid tert-butyl ester (47)

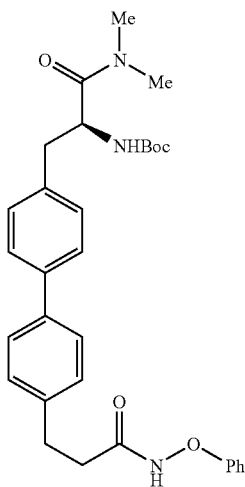

(47)

The acid compound 46 (1.9 g, 4.3 mmol) was dissolved in dry DMF (30 mL) and cooled to 0-5° C. 1-Hydroxybenzotriazole (0.64 g, 4.74 mmol), 1-(3-dimethylaminopropyl)-3-ethylcarbodiimide hydrochloride (0.83 g, 4.3 mmol), and triethylamine (1.8 mL, 13.0 mmol) were added to the above mixture followed by stirring for 15 min. O-Benzylhydroxylamine hydrochloride (0.76 g, 4.74 mmol) was added and the mixture was allowed to come to room temperature and stirred for 18 h. The solvent was evaporated under reduced pressure and the residual oil was taken up in EtOAc (75 mL). The organic layer was extracted with 2.0 M HCl (1×10 mL), saturated NaHCO$_3$ (1×10 mL), and brine (1×50 mL). The resulting EtOAc layer was dried and concentrated to yield the crude product. Flash chromatography (30-70% ethyl acetate in hexane containing 1% acetic acid) yielded the desired benzyl hydroxamate 47 (1.2 g, 53%).

Step VII

Preparation of {1-dimethylcarbamoyl-2-[4'-(2-hydroxycarbamoyl-ethyl)-biphenyl-4-yl]-ethyl}-carbamic acid tert-butyl ester (48)

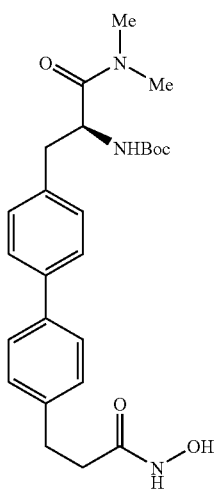
(48)

Palladium on BaSO$_4$ (5%, 1.0 g) was added to a degassed solution of the benzyl hydroxamate 47 (1.2 g) in MeOH (60 mL) and the suspension was treated with hydrogen at atmospheric pressure for 4 h. The suspension was filtered over a Celite® bed and concentrated to yield the desired hydroxamate 48 (1.0 g, 97%). $^1$H NMR (DMSO-d$_6$): 10.42 (br, 1H), 7.55 (d, J=7.6 Hz, 4H), 7.32 (d, J=8.0 Hz, 2H), 7.27 (d, J=8.4 Hz, 2H), 7.13 (d, J=8.4 Hz, 1H), 4.57 (m, 1H), 2.94 (s, 3H), 2.73-2.91 (m, 7H), 2.29 (t, J=8.0 Hz, 2H), 1.31 (s, 9H).

Step VIII

Preparation of 2-amino-3-[4'-(2-hydroxycarbamoyl-ethyl)-biphenyl-4-yl]-N,N-dimethylpropionamide hydrochloric acid salt (49)

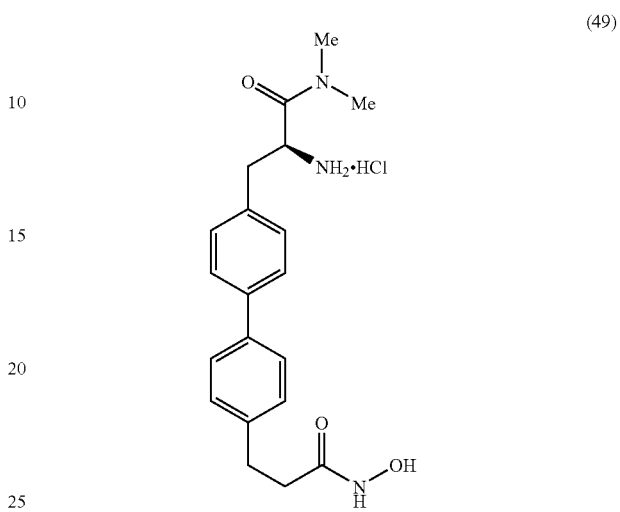
(49)

The hydroxamate 48 (0.9 g) was dissolved in CH$_2$Cl$_2$ (25 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×30 mL), decanted, and dried to yield the desired compound 49 as a white amorphous solid (0.68 g, 88%). $^1$H NMR (DMSO-d$_6$): 10.45 (s, 1H), 7.61 (d, J=8.4 Hz, 2H), 7.57 (d, J=8.0 Hz, 2H), 7.29 (d, J=8.4 Hz, 2H), 4.58 (m, 1H), 3.09 (dd, J=14.0 and 8.4 Hz, 1H), 3.01 (dd, J=14.0 and 7.2 Hz, 1H), 2.84 (t, J=6.8 Hz, 2H), 2.81 (s, 3H), 2.71 (s, 3H), 2.29 (t, J=7.2 Hz, 2H). LCMS (m/e): Obsd. [MH]$^+$ 356, Calcd. 355.4

EXAMPLE 14

Synthesis of 3-[4'-(2-amino-2-dimethylcarbamoyl-ethyl)-biphenyl-4-yl]-propionic acid hydrochloride (50)

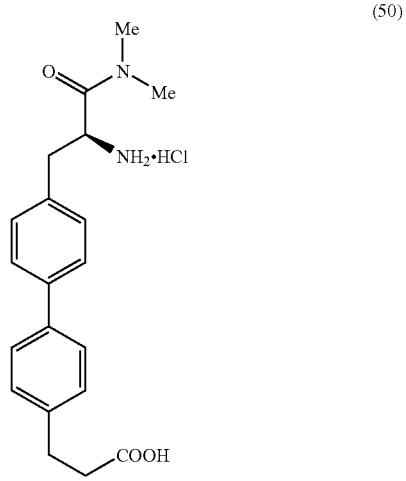
(50)

The acid compound 46 (0.9 g) was dissolved in CH$_2$Cl$_2$ (25 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×25 mL), decanted, and dried to yield the desired compound 50 as a white amorphous solid (0.64 g, 83%). $^1$H NMR (DMSO-d$_6$): 12.2 (br, 1H), 7.62 (d, J=8.4 Hz, 2H), 7.56 (d, J=8.0 Hz, 2H), 7.31 (d, J=8.4 Hz, 2H), 7.29 (d, J=8.0 Hz, 2H), 4.58 (m, 1H), 3.02-3.08 (m, 2H), 2.85 (t, J=7.6 Hz, 2H), 2.81 (s, 3H), 2.71 (s, 3H), 2.57 (t, J=7.6 Hz, 2H). LCMS (m/e): Obsd. [MH]$^+$ 341, Calcd. 340.4.

EXAMPLE 15

Synthesis of 2-amino-3-[4'-(2-carbamoylethyl)-biphenyl-4-yl]-N,N-dimethylpropionamide hydrochloric acid salt (52)

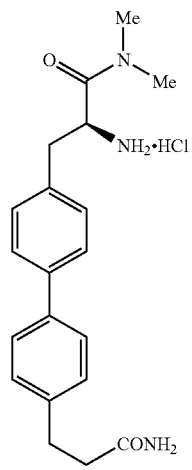

Step I

Preparation of {2-[4'-(2-carbamoylethyl)-biphenyl-4-yl]-1-dimethylcarbamoylethyl}-carbamic acid tert-butyl ester (51)

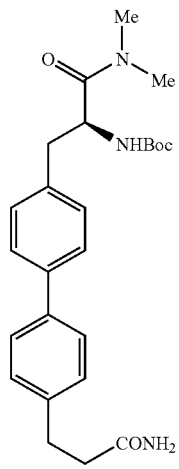

Acid compound 46 (1.2 g, 2.73 mmol) was dissolved in DCM (30 mL). Triethylamine (0.46 mL, 3.27 mmol) and BOP reagent (1.33 g, 3.0 mmol) were added and the reaction mixture stirred at room temperature for 15 min under an atmosphere of argon. Ammonia gas was then bubbled gently through the solution for 15-20 min to complete the reaction. Excess ammonia was degassed, the solvent was removed under reduced pressure and the residue was suspended in EtOAc (75 mL). The organic layer was washed with 0.5 N NaOH (2×10 mL), water (2×25 mL), and brine (1×30 mL), dried and concentrated under reduced pressure to yield the amide compound 51 (1.1 g, 92%). $^1$H NMR (DMSO-d$_6$): 7.54 (d, J=8.0 Hz, 4H), 7.31 (d, J=8.0 Hz, 2H), 7.27 (d, J=8.4 Hz, 2H), 7.09 (d, J=8.4 Hz, 1H), 6.77 (br, 1H), 4.56 (m, 1H), 2.93 (s, 3H), 2.75-2.90 (m, 7H), 2.74 (t, J=8.4 Hz, 2H), 1.30 (s, 9H).

Step II

Preparation of 2-amino-3-[4'-(2-carbamoylethyl)-biphenyl-4-yl]-N,N-dimethylpropionamide hydrochloric acid salt (52)

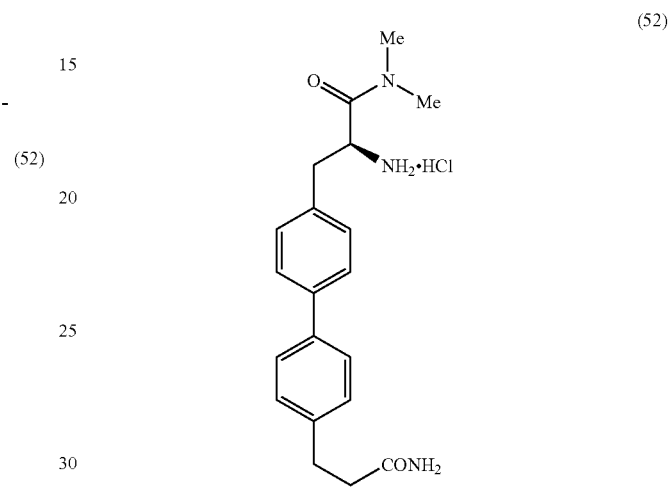

The amide compound 51 (1.0 g) was dissolved in CH$_2$Cl$_2$ (25 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×50 mL), decanted, and dried to yield the desired compound 52 as a white amorphous solid that was extremely hygroscopic (0.68 g, 79.5%). $^1$H NMR (DMSO-d$_6$): 7.62 (d, J=8.4 Hz, 2H), 7.57 (d, J=8.0 Hz, 2H), 7.34 (d, J=8.4 Hz, 2H), 7.29 (d, J=8.4 Hz, 2H), 6.78 (br, 1H), 4.58 (m, 1H), 2.95 (m, 2H), 2.81-2.85 (m, 5H), 2.72 (s, 3H), 2.38 (t, J=8.0 Hz, 2H). LCMS (m/e): Obsd. [MH]$^+$ 340, Calcd. 339.4.

EXAMPLE 16

Synthesis of 3-{4'-[2-dimethylcarbamoyl-2-(toluene-4-sulfonylamino)-ethyl]-biphenyl-4-yl}-propionic acid (69)

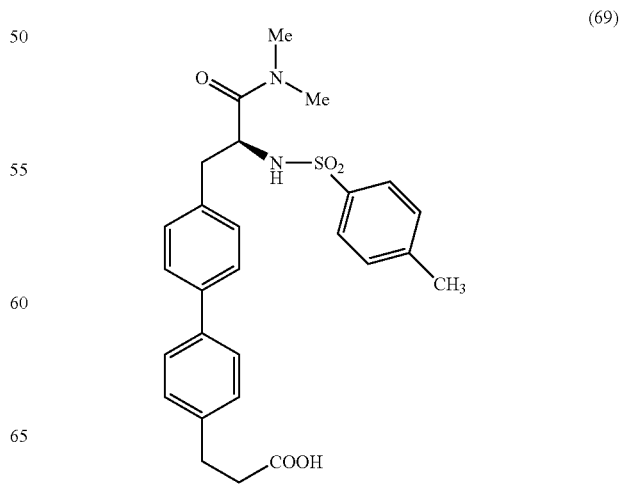

Step I

Preparation of 3-[4'-(2-amino-2-dimethylcarbamoyl-ethyl)-biphenyl-4-yl]-propionic acid methyl ester hydrochloric acid salt (53)

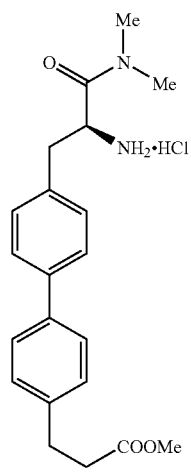

(53)

Amide compound 45 (2.7 g) was dissolved in CH$_2$Cl$_2$ (50 mL) and cooled to 0-5° C. Hydrogen chloride gas was bubbled through this solution for 20 min. The bubbling was discontinued and the reaction mixture was stirred at room temperature for 2 h. The excess HCl was degassed and the CH$_2$Cl$_2$ was removed. The residual sticky solid was dried under vacuum without further purification to yield the crude hydrochloride salt 53 (2.2 g, 94.8%). $^1$H NMR (DMSO-d$_6$): 10.55 (b, 1H), 7.61 (d, J=8.0 Hz, 2H), 7.58 (d, J=8.4 Hz, 2H), 7.31 (overlapped d, J=8.4 Hz, 2H), 7.29 (d, J=8.4 Hz, 2H), 4.57 (m, 1H), 3.58 (s, 3H), 2.99-3.20 (m, 2H), 2.88 (t, J=7.6 Hz, 2H), 2.80 (s, 3H), 2.69 (s, 3H), 2.66 (t, J=7.6 Hz, 2H).

Step II

Preparation of 3-{4'-[2-dimethylcarbamoyl-2-(toluene-4-sulfonylamino)-ethyl]-biphenyl-4-yl}-propionic acid methyl ester (54)

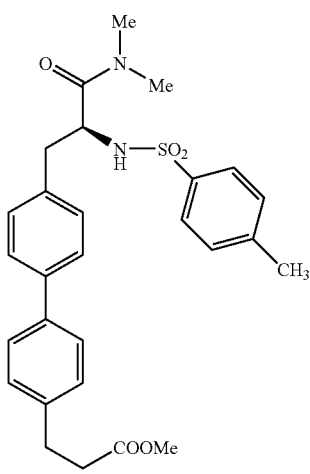

(54)

Hydrochloride compound 53 (2.1 g, 5.37 mmol) was dissolved in CH$_2$Cl$_2$ (35 mL) and cooled to 0-5° C. N,N-Diisopropylethylamine (1.87 mL, 11.0 mmol) was added to the above solution followed by addition of p-toluenesulfonyl chloride (0.85 g, 4.46 mmol) in small portions. The reaction mixture was then warmed up to room temperature and stirred overnight. The solvent was removed under reduced pressure and the residual oil was taken up in EtOAc (50 mL). The organic layer was washed with 2.0 M HCl (1×10 mL), saturated NaHCO$_3$ (1×10 mL), and brine (1×25 mL). The resulting EtOAc layer was dried and concentrated under reduced pressure to yield an oil. Flash chromatography (30-50% ethyl acetate in hexane containing 1% acetic acid) yielded the desired sulfonamide 54 (1.1 g, 40%). $^1$H NMR (DMSO-d$_6$): 8.10 (d, J=9.6 Hz, 1H), 7.55 (d, J=8.0 Hz, 2H), 7.51 (d, J=8.4 Hz, 2H), 7.48 (d, J=8.4 Hz, 2H), 7.30 (d, J=8.4 Hz, 2H), 7.23 (d, J=8.0 Hz, 2H), 7.18 (d, J=8.4 Hz, 2H), 4.33 (m, 1H), 3.59 (s, 3H), 2.81-2.90 (m, 3H), 2.75 (s, 3H), 2.62-2.68 (m, 3H), 2.53 (s, 3H), 2.26 (s, 3H).

Step III

Preparation of 3-{4'-[2-dimethylcarbamoyl-2-(toluene-4-sulfonylamino)-ethyl]-biphenyl-4-yl}-propionic acid (55)

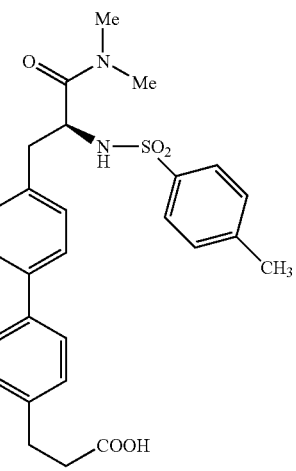

(55)

The sulfonamide compound 54 (1.1 g, 2.06 mmol) was dissolved in THF (30 mL) and diluted with water (30 mL). Lithium hydroxide (0.2 g, 8.26 mmol) was added and the reaction mixture was stirred at room temperature for about 2 h. The THF was evaporated and the resulting aqueous layer was acidified with 2.0 M HCl and extracted into EtOAc (2×25 mL). The organic layer was washed with water (1×25 mL) and brine (1×25 mL), dried and concentrated to yield the desired acid compound 55 (1.05 g, 98%). $^1$H NMR (400 MHz, DMSO-d$_6$): 12.2 (br, 1H), 8.09 (d, J=9.2 Hz, 1H), 7.55 (d, J=8.4 Hz, 2H), 7.51 (d, J=8.0 Hz, 2H), 7.48 (d, J=8.4 Hz, 2H), 7.30 (d, J=8.4 Hz, 2H), 7.24 (d, J=8.4 Hz, 2H), 7.18 (d, J=8.0 Hz, 2H), 4.33 (m, 1H), 2.81-2.87 (m, 3H), 2.75 (s, 3H), 2.61-2.67 (m, 1H), 2.56 (t, J=8.0 Hz, 2H), 2.53 (s, 3H), 2.27 (s, 3H).

EXAMPLE 17

Synthesis of 3-[4'-(2-hydroxycarbamoylethyl)-biphenyl-4-yl]-N,N-dimethyl-2-(toluene-4-sulfonylamino)-propionamide (57)

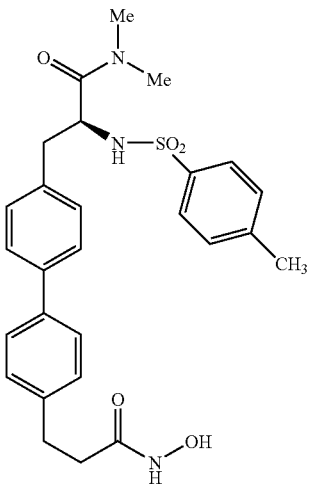

(57)

Step I

Preparation of N,N-dimethyl-3-[4'-(2-phenoxycarbamoylethyl)-biphenyl-4-yl]-2-(toluene-4-sulfonylamino)-propionamide (56)

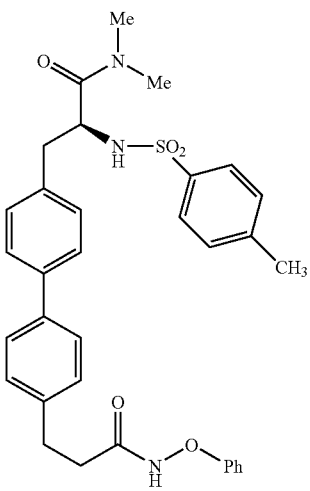

(56)

The compound 3-{4'-[2-dimethylcarbamoyl-2-(toluene-4-sulfonylamino)-ethyl]-biphenyl-4-yl}-propionic acid, (1.05 g, 2.1 mmol) was dissolved in dry DMF (20 mL) and cooled to 0-5° C. 1-Hydroxybenzotriazole (0.32 g, 2.34 mmol), 1-(3-dimethylaminopropyl)-3-ethylcarbodiimide hydrochloride (0.41 g, 2.13 mmol), and triethylamine (0.9 mL, 6.37 mmol) were added to the above mixture followed by stirring for 15 min. O-Benzylhydroxylamine hydrochloride (0.37 g, 2.34 mmol) was added and the mixture was allowed to come to room temperature and stirred for 18 h. The solvent was evaporated under reduced pressure and the residual oil was taken up in CHCl$_3$ (50 mL). The organic layer was extracted with 2.0 M HCl (1×10 mL), saturated NaHCO$_3$ (1×10 mL), and brine (1×25 mL). The resulting CHCl$_3$ layer was dried and concentrated to yield the crude product. Flash chromatography (30-70% ethyl acetate in hexane containing 1% acetic acid) yielded the desired benzyl hydroxamate 56 (0.8 g, 64.5%). $^1$H NMR (400 MHz, DMSO-d$_6$): 10.97 (s, 1H), 8.09 (d, J=8.4 Hz, 1H), 7.55 (d, J=8.4 Hz, 2H), 7.51 (d, J=8.0 Hz, 2H), 7.49 (d, J=8.4 Hz, 2H), 7.30-7.35 (m, 5H), 7.27 (d, J=8.4 Hz, 2H), 7.24 (d, J=8.4 Hz, 2H), 7.18 (d, J=8.4 Hz, 2H), 4.73 (s, 2H), 4.33 (m, 1H), 2.81-2.89 (m, 3H), 2.74 (s, 3H), 2.64 (dd, J=14.0 and 8.0 Hz, 1H), 2.53 (s, 3H), 2.29 (t, J=7.6 Hz, 2H), 2.27 (s, 3H).

Step II

Preparation of 3-[4'-(2-Hydroxycarbamoyl-ethyl)-biphenyl-4-yl]-N,N-dimethyl-2-(toluene-4-sulfonylamino)-propionamide (57)

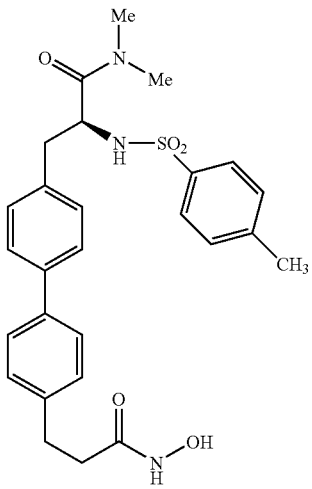

(57)

Palladium (5% on BaSO$_4$) (0.5 g) was added to a degassed solution of the benzyl hydroxamate 56 (0.8 g) in MeOH (50 mL) and the suspension was treated with hydrogen at atmospheric pressure for 4 h. The suspension was filtered over a Celite® bed and concentrated to yield the desired hydroxamate 57 (0.2 g, 29%). $^1$H NMR (400 MHz, DMSO-d$_6$): 10.39 (br, 1H), 8.09 (d, J=9.6 Hz, 1H), 7.54 (d, J=8.4 Hz, 2H), 7.49 (d, J=8.4 Hz, 2H), 7.27 (d, J=8.4 Hz, 2H), 7.24 (d, J=8.4 Hz, 2H), 7.18 (d, J=8.4 Hz, 2H), 4.33 (m, 1H), 2.81-2.86 (m, 3H), 2.75 (s, 3H), 2.61-2.67 (m, 1H), 2.53 (s, 3H), 2.28 (s, 3H).

EXAMPLE 18

Synthesis of L-2-amino-3-{4-[2-(2-hydroxycarbamoylethyl)-phenoxy]-phenyl}-N,N-dimethylpropionamide hydrochloric acid salt (65)

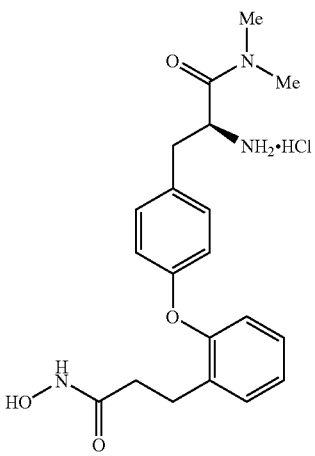

(65)

Step I

Preparation of 2-tert-butoxycarbonylamino-3-[4-(2-formylphenoxy)-phenyl]-propionic acid (58)

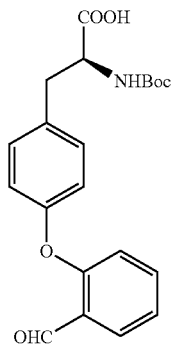
(58)

Potassium carbonate (7.36 g, 53.31 mmol) and -2-fluorobenzaldehyde (9.3 mL, 88.85 mmol) were added to a solution of Boc-tyrosine (5.0 g, 17.77 mmol) in anhydrous DMF (20 mL). The resulting suspension was refluxed at 75±5° C. under an atmosphere of argon. After 48 hr, the reaction mixture was cooled to room temperature, diluted with water (100 mL) and extracted with EtOAc (2×50.0 mL). The aqueous layer was collected, acidified with 5.0 M HCl to pH ~2.0 and extracted with EtOAc (2×100 mL). The resulting EtOAc layer was extracted with water (1×100 mL) and brine (1×100 mL), dried over anhydrous magnesium sulfate, filtered and concentrated under reduced pressure to yield the desired aldehyde, 58, as a low melting solid (6.4 g, ~99%). $^1$H NMR (400 MHz, DMSO-d$_6$): 12.62(s, 1H), 10.38 (s, 1H), 7.84 (dd, J=8.0 and 2.0 Hz, 1H), 7.64 (dt, J=7.2 and 1.6 Hz, 1H) 7.31 (d, J=8.8 Hz, 1H), 7.27 (t, J=7.6 Hz, 2 Hz), 7.13 (d, J=8.4 Hz, 1H), 7.06 (d, J=8.4 Hz, 2H) 6.89 (d, J=8.4 Hz, 1H), 4.09 (ddd, J=12.8, 10.8 and 4.4 Hz, 1H), 3.02 (dd, J=13.6 and 4.4 Hz, 1H), 2.81 (dd, J=13.6 and 10.4 Hz, 1H) 1.32 (s, 9H).

Step II

Preparation of 3-{2-[4-(2-tert-butoxycarbonylamino-2-carboxyethyl)-phenoxy]-phenyl}-acrylic acid methyl ester (59)

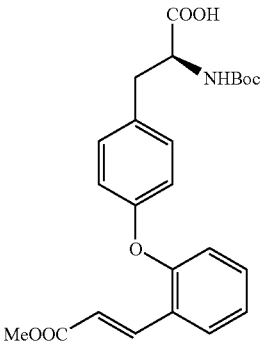
(59)

Sodium hydride (60% in mineral oil, 0.57 g, 14.278 mmol) was washed with anhydrous hexane (3×30 mL) under an atmosphere of argon. Dry THF (50 mL) was added and cooled to 0-5° C. A solution of trimethylphosphonoacetate (1.30 mL, 7.139 mmol) in dry THF (8.0 mL) was added dropwise to the above mixture with stirring. After about 5 min, a solution of the aldehyde 58 (2.5 g, 6.486 mmol) in dry THF (20 mL) was added and the reaction mixture was then brought up to room temperature and stirred. After 30 min, the clear reaction mixture was quenched with 10% citric acid (50 mL) and further acidified to pH ~2.0 with 2.0 M HCl. The THF was evaporated under reduced pressure and the resulting oily material was extracted with EtOAc (2×200 mL). The organic layer was extracted with water (3×200 mL), and brine (1×200 mL), dried over anhydrous magnesium sulfate, filtered and concentrated in vacuo to yield the unsaturated ester 59 (2.7 g, 98.0%). $^1$H NMR (400 MHz, DMSO-d$_6$): 12.62 (s, 1H), 7.91 (dd, J=7.6 and 1.6 Hz, 1H) 7.85 (d, J=16.4 Hz, 1H), 7.42 (dt, J=8.4 and 1.2 Hz, 1H), 7.28 (d, J=13.6, 2H), 7.17 (t, 8.0 Hz, 1H), 7.11 (d, J=8.4 Hz, 1H) 6.93 (d, J=2.8 Hz, 2H), 6.84 (d, J=8.4 Hz, 1H), 6.65 (d, J=16.4 Hz, 1H), 4.08 (m, 1H), 3.68 (s, 3H), 3.03 (dd, J=13.6 and 4.4 Hz, 1H), 2.80 (dd, J=13.6 and 10.0 Hz, 1H), 1.32 (s, 9H).

Step III

Preparation of 2-tert-butoxycarbonylamino-3-{4-[2-(2-methoxycarbonylethyl)-phenoxy]-phenyl}-propionic acid (60)

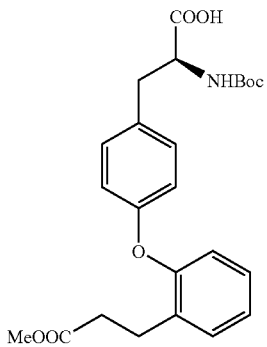
(60)

Raney nickel 2800 (2.5 g) was added to a degassed solution of the unsaturated ester 59 (2.5 g) in MeOH (50.0 mL) and the resulting suspension was treated with hydrogen at atmospheric pressure for 18 h. The suspension was filtered over a Celite® bed and concentrated. Flash chromatography (30-50% ethyl acetate in hexane containing 1% acetic acid) of the resulting residue gave the desired saturated ester 60 (2.2 g, 98%). $^1$H NMR (400 MHz, DMSO-d$_6$): 12.63 (s, 1H), 7.31 (dd, J=7.6 and 1.6 Hz, 1H), 7.21 (m, 3H), 7.08 (m, 2H), 6.85 (d, J=8.4 Hz, 2H), 6.77 (d, J=7.6 Hz, 1H), 4.06 (m, 1H), 3.55 (s, 3H), 3.0 (m, 1H), 2.84 (t, J=7.2 Hz, 2H) 2.76 (m, 1H) 2.61 (t, J=7.2 Hz, 2H), 1.31 (s, 9H)

Step IV

Preparation of 3-{2-[4-(2-tert-butoxycarbonylamino-2-dimethylcarbamoylethyl)-phenoxy]-phenyl}-propionic acid methyl ester (61)

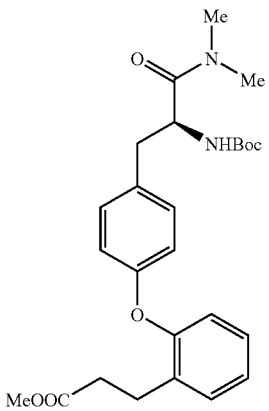
(61)

The hydrogenated compound 60 (2.2 g, 4.96 mmol) was dissolved in CH₂Cl₂ and stirred at room temperature under an atmosphere of argon. Triethylamine (0.829 mL, 5.95 mmol) and benzotriazol-1-yloxy-tris(dimethylamino)phosphonium hexafluorophosphate (BOP reagent, 2.413 g, 5.456 mmol) were added and the reaction mixture was stirred for 15 min. Dimethylamine (2.0 M solution in THF, 12.4 mL, 24.8 mmol) was added and the resulting solution was stirred at room temperature for about 2-3 h. The solvent was removed under reduced pressure and the resulting oil was taken up in EtOAc (100 mL). The organic layer was extracted with 0.5 N NaOH (1×30 mL), water (2×50.0 mL) and brine (1×50.0 mL). Drying and concentration of the organic layer gave the desired amide crude (1.2 g, ~98%). Flash chromatography on silica gel (methanol-chloroform 1%-2%) yielded the desired amide 75(0.8 g 98%) ¹H NMR (400 MHz, DMSO-d₆): 7.32 (dd, J=7.6 and 2 HZ, 1H), 7.21 (m, 3H), 7.08 (dd, J=14 and 7.2 Hz, 2H), 6.83 (d, J=8.8 Hz, 2H), 6.75 (d, J=8.0 Hz, 1H), 4.53 (m, 1H) 3.55 (s, 3H), 2.89 (s, 3H), 2.85-2.58 (m, 7H), 2.59 (t, J=7.6 Hz, 2H), 1.31 (s, 9H).

Step V

Preparation of 3-{2-[4-(2-tert-butoxycarbonylamino-2-dimethylcarbamoylethyl)-phenoxy]-phenyl}-propionic acid (62)

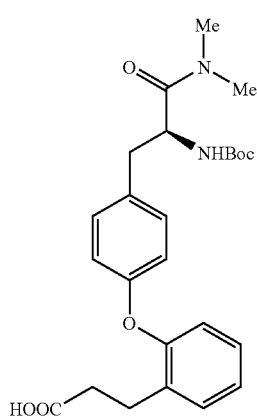

(62)

The ester 61 (0.8 g, 1.65 mmol) was dissolved in THF (10 mL) and diluted with water (10 mL). Lithium hydroxide (0.158 g, 6.6 mmol) was added and the reaction mixture was stirred at room temperature for about 2 h. The THF was evaporated and the resulting aqueous layer was acidified with 2.0 M HCl and extracted into EtOAc (2×100 mL). The organic layer was washed with water (1×100 mL) and brine (1×100 mL), dried and concentrated to yield the desired acid compound 62 (0.7 g, 97%). ¹H NMR (400 MHz, DMSO-d₆) 12.1 (s, 1H), 7.31 (dd, J=7.6 and 1.6 Hz, 1H) 7.21 (d, J=8.8 Hz, 2H), 7.18 (d, J=7.6 Hz, 1H), 7.08 (m, 2H), 6.82 (d, J=8.8 Hz, 2H), 6.76 (d, J=8.0 Hz, 1H), 4.52 (m, 1H), 2.88-2.81 (m, 10H), 1.31 (s, 9H)

Step VI

Preparation (2-{4-[2-(2-benzyloxycarbamoylethyl)-phenoxy]-phenyl}-1-dimethylcarbamoylethyl)-carbamic acid tert-butyl ester (63)

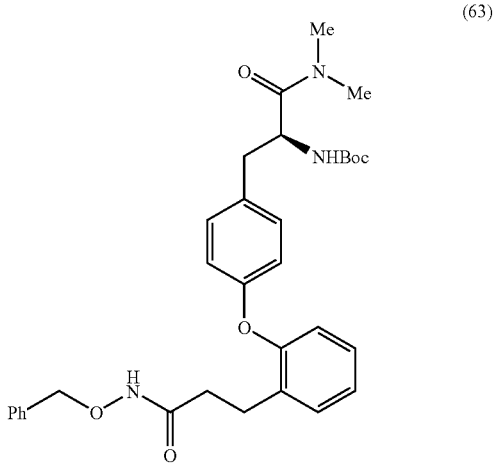

(63)

The acid compound 62 (0.7 g, 1.533 mmol) was dissolved in dry DMF and cooled to 0-5° C. 1-Hydroxybenzotriazole (0.227 g, 1.686 mmol), 1-(3-dimethylaminopropyl)-3-ethylcarbodiimide hydrochloride (EDCI, 0.293 g, 1.533 mmol), and triethylamine (0.641 mL, 4.59 mmol) were added to the above mixture followed by stirring for 15 min. O-Benzylhydroxylamine hydrochloride (0.269 g, 1.686 mmol) was added and the mixture was allowed to come to room temperature and stirred for 18 h. The solvent was evaporated under reduced pressure and the residual oil was taken up in EtOAc (100 mL). The organic layer was extracted with 2.0 M HCl (1×20 mL), saturated NaHCO₃ (1×20 mL), and brine (1×50 mL). The resulting EtOAc layer was dried and concentrated to yield the crude product. Flash chromatography (30-50% ethyl acetate in hexane containing 1% acetic acid) yielded the desired benzyl hydroxamate 63 (0.8 g, 98%). ¹H NMR (400 MHz, DMSO-d₆) 10.9 (s, 1H), 7.37-7.2 (m, 9H), 7.07 (t, J=7.2 Hz, 2H), 6.85 (d, J=8.4 Hz, 2H), 6.76 (d, J=7.6 Hz, 1H), 4.71 (s, 2H), 4.54 (m, 1H), 2.89 (s, 3H), 2.81-2.72 (m, 7H), 2.49 (t, J=1.6 Hz, 2H), 1.30 (s, 9H).

Step VII

Preparation of (1-dimethylcarbamoyl-2-{4-[2-(2-hydroxycarbamoyl-ethyl)-phenoxy]-phenyl}-ethyl)-carbamic acid tert-butyl ester (64)

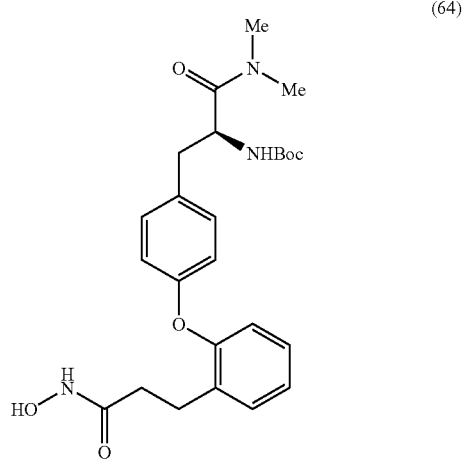

(64)

Palladium on BaSO$_4$ (5%, 0.24 g) was added to a degassed solution of the benzyl hydroxamate 63 (0.7 g) in MeOH (20.0 mL) and the suspension was treated with hydrogen at atmospheric pressure for 6 h. The suspension was filtered over a Celite® bed and concentrated to yield the desired hydroxamate 64 (0.7 g, 97%). $^1$H NMR (DMSO-d$_6$): 10.37 (s, 1H), 7.28 (d, J=7.6 Hz, 1H), 7.23-7.16 (m, 3H), 7.06 (t, J=8.4 Hz, 2H), 6.85 (d, J=8.8 Hz, 2H), 6.76 (d, J=7.6 Hz, 1H), 4.53 (m, 1H), 2.80 (s, 3H), 2.79-2.75 (m, 7H), 2.23 (t, J=2.0 Hz, 2H), 1.30 (s, 9H).

Step VIII

Preparation L-2-amino-3-{4-[2-(2-hydroxycarbamoylethyl)-phenoxy]-phenyl}-N,N-dimethylpropionamide hydrochloric acid salt (65)

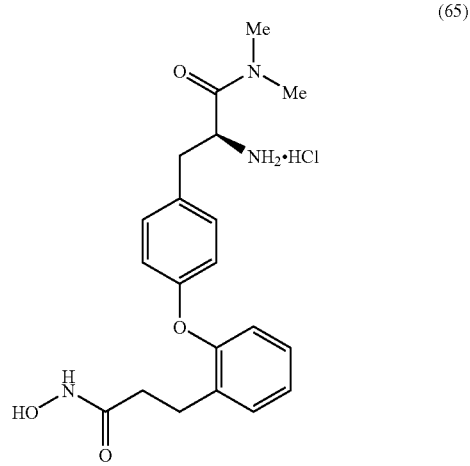

(65)

The hydroxamate 64 (0.5 g) was dissolved in CH$_2$Cl$_2$ and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×50 mL), decanted, and dried to yield the desired compound 65 as a white amorphous solid (0.4 g, 98%). $^1$H NMR (DMSO-d$_6$): 10.42 (s, 1H), 7.31 (dd, J=7.6 and 1.6 Hz, 1H), 7.22 (m, 1H), 7.19 (d, J=8.4 Hz, 1H), 7.11 (dt, J=7.2 and 1.2 Hz, 1H), 6.88(d, J=8.4 Hz, 2H), 6.82 (dd, J=8.0 and 0.8 Hz, 1H), 4.53 (m, 1H), 3.0 (dd, J=13.2 and 6 Hz, 1H) 2.93(dd, J=13.2 and 7.2 Hz, 1H), 2.81(s, 3H), 2.76 (t, J=7.6 Hz, 2H), 2.73 (s, 3H), 2.25 (t, J=7.6 Hz, 2H); LCMS (m/e): Obsd. 372.0, Calcd. 371.43

Protocols for Biological Testing:

Compounds of the present invention have been tested for lowering inflammatory cytokines level, nitric oxide, the enzyme inducible nitric oxide (iNOS) and showed significant body weight lowering in animal models. The attached FIGS. 1-7 show the activity profile of representative compounds.

FIG. 1. TNF-α Inhibition in Human Peripheral Blood Monocytic Cells (hPBMC)

Compounds of the invention show inhibition of major pro-inflammatory cytokine, TNF-α, in human peripheral blood mononuclear cells isolated from volunteers. Human PBMC cells were cultured and incubated with compounds at 1 μM concentration and a positive control dexamethasone (10 μM). Cells (1×10$^6$/mL) were challenged with lipopolysaccharides (LPS) at a concentration of (100 ng/mL) for 20 hours. Cell supernatant was analyzed for the presence of TNF-α by antibody directed enzyme-linked immunoassay (R & D Systems, MN, USA).

FIG. 2. IL-6 and IL-1β Inhibition in Human Peripheral Blood Monocytic Cells (hPBMC)

This figure shows the inhibition of major pro-inflammatory cytokines IL-6 and IL-1β by compound 9 in human peripheral blood mononuclear cells isolated from volunteers. Human PBMC cells were cultured and incubated with compounds at 1 μM concentration and a positive control dexamethasone (10 μM). Cells (1×10$^6$/mL) were challenged with lipopolysaccharides (LPS) at a concentration of (100 ng/mL) for 20 hours. Cell supernatant was analyzed for the presence of IL-6 and IL-1β by antibody directed enzyme-linked immunoassay (R & D Systems, MN, USA).

FIG. 3. Selective Inhibition of iNOS Expression in RAW-264.7 Cells

The inflammatory stimulus, LPS, induces inducible nitric oxide synthase (iNOS) enzyme in this system and as a result nitric oxide (NO) is produced. Mouse macrophage cells, RAW-264.7 were incubated with the compound 9 for 1 h and then challenged with LPS for next 6 h. Total cell lysates were analyzed by western blot with anti-iNOS antibody (Transduction Laboratories, BD Pharmingen).

FIG. 4. Inhibition of LPS Induced NO in Mouse Peritoneal Macrophages

Mouse peritoneal macrophages were isolated by injecting warm PBS in the peritoneum and cells were tapped out with syringe and stored in a tube. After two washes with PBS, cells were plated in 96 well plates and incubated with compound 9 for 1 hour and then challenged with LPS (10 μg/mL) for 48 hrs. Supernatant was assayed for NO by ELISA kit (R&D Biosystems). In this test compound 9 doses dependently inhibited NO production in these cells after LPS challenge.

FIG. 5. Inhibition of PPARγ Agonist Induced Adipocytes Differentiation

Adipogenesis is defined as the production of fat laden adipocytes from fibroblast cells. All known PPARγ agonists induce adipogenesis after a long term of treatment. Rosiglitazone, a known agonist of this transcriptional factor PPARγ, strongly induces adipocyte differentiation in mouse fibroblasts cells call 3T3-L1 cells. In this test cells were treated with either rosiglitazone (1 μM) or compound 9 (10 μM) alone or they were mixed in the same well to see their combined effect. Cells were cultured for 11 days and every 48 h fresh drug was given while changing the media. The compound 9 is not adipogenic whereas rosiglitazone showed strong adipocyte differentiation after staining with Oil red O. It blocks the adipogenesis process induced by PPARγ agonist, showing that it can be used for the control of obesity.

FIG. 6. Compound 9 and Sibutramine Reduced Bodyweight Gain in High Fat Diet Induced Obesity (DIO) Model Six week old C57BL/6J male mice were fed with high fat (60%) diet for 14 days. From day 15 onwards animals were treated with compound 9 at a dose of 50 mg/kg body weight or sibutramine (5 mg/kg bw) for 60 days. All the animals were dosed once daily during morning hours up to day 15. From day 16 to end of the study animals were dosed during evening hours. The compound 9 lowered body weight without a significant change in food and water intake. It significantly lowered free fatty acid and triglyceride levels compare to control animals and improved oral glucose tolerance.

FIG. 7. Hypoglycemic Effect in Normal Lean Mice

C57BL/6J lean male mice were fed, ad libitum, with laboratory rodent diet and purified water. Animals were treated with compound 9 at a dose of 50 mg/kg body weight for 60 days. Blood glucose was measured with an ACCUCHECK® glucose meter every third day during morning hours. No change in blood glucose levels was observed.

The invention claimed is:

1. A compound of the formula (I)

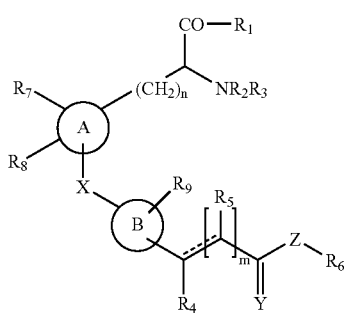

its stereoisomers, pharmaceutically acceptable salts and pharmaceutical compositions, wherein, represents a bond or no bond;

A is selected from the group consisting of substituted and unsubstituted 5 to 18-membered aryl;

B represents a ring system selected from the group consisting of substituted and unsubstituted 5 to 18-membered aryl;

$R_1$ represents —$OR^{10}$ or $NR^{11}R^{12}$;

$R_2$ and $R_3$ may be same or different and independently represent H, $COR^{13}$, substituted or unsubstituted groups selected from alkyl, alkenyl, aryl, alkylsufonyl, alkylsulfinyl, arylsulfonyl, arylsulfinyl, alkylthio or arylthio;

$R_4$ represents hydrogen, substituted or unsubstituted groups selected from the group consisting of alkyl, aryl, and araalkyl;

$R_5$ represents H, halogen, nitro, cyano, formyl, substituted or unsubstituted groups selected from the group consisting of alkyl, alkenyl, haloalkyl, alkoxy, aryl, alkanoyl and carboxylic acids and its derivatives;

$R_7$, $R_8$, and $R_9$ may be same or different and represent hydrogen, nitro, nitrile, hydroxy, formyl, azido, halo, or substituted or unsubstituted groups selected from the group consisting of alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl and carboxylic acid and its derivatives;

$R^{10}$ represents hydrogen, substituted or unsubstituted groups selected from the group consisting of alkyl, alkenyl, aryl, aralkyl, and a counter ion;

$R^{11}$ and $R^{12}$ may be same or different and independently represent H, substituted or unsubstituted groups selected from the group consisting of alkyl, alkenyl and aryl or $R^{11}$ and $R^{12}$ together with nitrogen may represent substituted or unsubstituted mono or bicyclic saturated or unsaturated ring system which may contain one or more heteroatoms selected from O, S or N provided that said ring system is piperazine or morpholine;

$R^{13}$ represents H, substituted or unsubstituted groups selected from the group consisting of alkyl, aryl, alkenyloxy, aryloxy, and alkoxy;

Z represents O, S or $NR^{14}$, $R^{14}$ represents hydrogen or alkyl; when Z represents O or S, $R_6$ represents hydrogen or substituted or unsubstituted groups select from the group consisting of alkyl, alkenyl, aryl, aralkyl, cycloalkyl; when Z represents $NR^{14}$, $R_6$ represents H, hydroxy, protected hydroxyl group, alkyloxy, aryloxy, amino, substituted or unsubstituted groups select from the group consisting of alkyl, haloalkyl, alkenyl, monoalkylamino, dialkylamino, aryl, aralkyl and cycloalkyl;

$R^{14}$ represents hydrogen or alkyl;

Y represents O, S or $NR^{14}$;

m is an integer from 0 to 8;

n is an integer from 0 to 4;

X represents a bond, O, S, SO or $SO_2$.

2. A compound according to claim 1 wherein A is phenyl.

3. A compound according to claim 1 wherein B is phenyl.

4. A compound according to claim 1 wherein $R_1$ is selected from the group consisting of dialkylamino, amino, i-propoxyl, hydroxyl, benzyloxyl, N-acetyl-perhydro-1,4-dithiaindinyl and perhydro-1,4-oxazaindinyl.

5. A compound according to claim 1 wherein $R_3$ is selected from the group consisting of hydrogen and p-toluenesulfonyl.

6. A compound according to claim 1 wherein $R_2$, $R_4$ and $R_5$ are hydrogen.

7. A compound according to claim 1 wherein $R_6$ is selected from the group consisting of hydroxyl, alkyl, hydrogen and dialkylmethyl.

8. A compound according to claim 1 wherein $R_7$, $R_8$ and $R_9$ are hydrogen.

9. A compound according to claim 1 wherein X is a bond or O.

10. A compound according to claim 1 wherein Y is O.

11. A compound according to claim 1 wherein Z is NH or O.

12. A compound according to claim 1 wherein m is 0 or 1.

13. A compound according to claim 1 wherein n is 0, 1 or 2.

14. A compound according to claim 1 selected from the group consisting of:

L-2-amino-3-{4-[4-(2-hydroxycarbamoylethyl)-phenoxy]-phenyl}-N,N-dimethylpropionamide hydrochloride;

3-{4-[4-(2-amino-2-dimethylcarbamoylethyl)-phenoxy]-phenyl}-propionic acid hydrochloride;

2-amino-3-{4-[4-(2-carbamoylethyl)-phenoxy]-phenyl}-N,N-dimethyl-propionamide hydochloride;

3-(4-{4-[2-dimethylcarbamoyl-2-(toluene-4-sulfonylamino)-ethyl]-phenoxy}-phenyl)-propionic acid;

3-{4-[4-(2-hydroxycarbamoylethyl)-phenoxy]-phenyl}-N,N-dimethyl-2-(toluene-4-sulfonylamino)-propionamide;

D-2-amino-3-{4-[4-(2-hydroxycarbamoyl-ethyl)-phenoxy]-phenyl}-N,N-dimethyl-propionamide hydrochloride;

3-{4-[4-(aminodimethylcarbamoylmethyl)-phenoxy]-phenyl}-N-hydroxy-propionamide hydrochloric acid salt;

3-{4-[4-(aminodimethylcarbamoylmethyl)-phenoxy]-phenyl}-propionic acid;

3-{4-[4-(aminodimethylcarbamoylmethyl)-phenoxy]-phenyl}-propionamide hydrochloric acid salt;

3-{4-[4-aminodimethylcarbamoylmethyl)-phenoxy]-phenyl}-N,N-dimethylpropionamide hydrochloric acid salt;

2-amino-3-[4'-(2-hydroxycarbamoylethyl)-biphenyl-4-yl]-N,N-dimethylpropionamide hydrochloric acid salt;

3-[4'-(2-amino-2-dimethylcarbamoylethyl)-biphenyl-4-yl]-propionic acid hydrochloride;

2-amino-3-[4'-(2-carbamoylethyl)-biphenyl-4-yl]-N,N-dimethylpropionamide hydrochloric acid salt;

3-{4'-[2-dimethylcarbamoyl-2-(toluene-4-sulfonylamino)-ethyl]-biphenyl-4-yl}-propionic acid;

3-[4'-(2-hydroxycarbamoylethyl)-biphenyl-4-yl]-N,N-dimethyl-2-(toluene-4-sulfonylamino)-propionamide; and L-2-amino-3-{4-[2-(2-hydroxycarbamoylethyl)-phenoxy]-phenyl}-N,N-dimethylpropionamide hydrochloric acid salt.

15. A pharmaceutical composition comprising a pharmaceutically effective amount of a compound of formula (I):

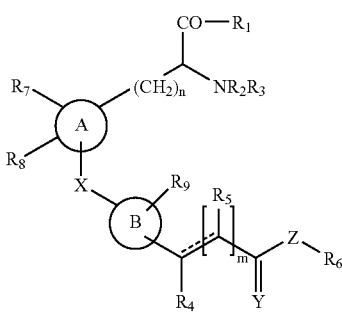

as defined in claim 1 and a pharmaceutically acceptable carrier, diluent, excipient or solvent.

16. A pharmaceutical composition according to claim 15 in the form of a tablet, capsule, powder, syrup, solution, aerosol or suspension.

17. A compound according to claim 1 wherein said pharmaceutically acceptable salt is selected from the group consisting of a hydrochloride, hydrobromide, potassium and magnesium salt.

18. A compound according to claim 14 selected from the group consisting of:

L-2-amino-3-{4-[4-(2-hydroxycarbamoylethyl)-phenoxy]-phenyl}-N,N-dimethylpropionamide hydrochloride;

D-2-amino-3-{4-[4-(2-hydroxycarbamoyl-ethyl)-phenoxy]-phenyl}-N,N-dimethyl-propionamide hydrochloride;

3-{4-[4-(aminodimethylcarbamoylmethyl)-phenoxy]-phenyl}-N-hydroxy-propionamide hydrochloric acid salt;

2-amino-3-[4'-(2-hydroxycarbamoylethyl)-biphenyl-4-yl]-N,N-dimethylpropionamide hydrochloric acid salt;

3-[4'-(2-hydroxycarbamoylethyl)-biphenyl-4-yl]-N,N-dimethyl-2-(toluene-4-sulfonylamino)-propionamide; and L-2-amino-3-{4-[2-(2-hydroxycarbamoylethyl)-phenoxy]-phenyl}-N,N-dimethylpropionamide hydrochloric acid salt.

19. The compound according to claim 18 L-2-amino-3-{4-[4-(2-hydroxycarbamoylethyl)-phenoxy]-phenyl}-N,N-dimethylpropionamide hydrochloride.

20. The compound according to claim 18 is D-2-amino-3-{4-[4-(2-hydroxycarbamoyl-ethyl)-phenoxy]-phenyl}-N,N-dimethyl-propionamide hydrochloride.

21. The compound according to claim 18 is 3-{4-[4-(aminodimethylcarbamoylmethyl)-phenoxy]-phenyl}-N-hydroxy-propionamide hydrochloric acid salt.

22. The compound according to claim 18 is 2-amino-3-[4'-(2-hydroxycarbamoylethyl)-biphenyl-4-yl]-N,N-dimethyl-propionamide hydrochloric acid salt.

23. The compound according to claim 18 is 3-[4'-(2-hydroxycarbamoylethyl)-biphenyl-4-yl]-N,N-dimethyl-2-(toluene-4-sulfonylamino)-propionamide.

24. The compound according to claim 18 is L-2-amino-3-{4-[2-(2-hydroxycarbamoylethyl)-phenoxy]-phenyl}-N,N-dimethylpropionamide hydrochloric acid salt.

* * * * *